US008183001B2

(12) United States Patent
Bamber et al.

(10) Patent No.: US 8,183,001 B2
(45) Date of Patent: May 22, 2012

(54) METHODS AND COMPOSITIONS RELATED TO GABA RECEPTOR SUBUNITS

(75) Inventors: Bruce A. Bamber, Toledo, OH (US); Bryan B. Wardell, Farmington, UT (US)

(73) Assignee: University of Research Foundation, Salt Lake City, UT (US)

( * ) Notice: Subject to any disclaimer, the term of this patent is extended or adjusted under 35 U.S.C. 154(b) by 0 days.

(21) Appl. No.: 12/301,565

(22) PCT Filed: May 21, 2007

(86) PCT No.: PCT/US2007/012089
§ 371 (c)(1),
(2), (4) Date: Nov. 19, 2008

(87) PCT Pub. No.: WO2007/136838
PCT Pub. Date: Nov. 29, 2007

(65) Prior Publication Data
US 2009/0312298 A1 Dec. 17, 2009

Related U.S. Application Data

(60) Provisional application No. 60/801,994, filed on May 19, 2006.

(51) Int. Cl.
*G01N 33/567* (2006.01)
*C07K 14/705* (2006.01)
(52) U.S. Cl. .......... 435/7.21; 435/7.1; 435/7.2; 436/501
(58) Field of Classification Search ........................ None
See application file for complete search history.

(56) References Cited

U.S. PATENT DOCUMENTS 5,585,277 A 12/1996 Bowie et al.
2003/0065144 A1 4/2003 Bamber et al.

OTHER PUBLICATIONS

Buhr et al., Point Mutations of the alpha1beta2gama2 gama-Aminobutyric AcidA Receptor Affecting Modulation of the Channel by Ligands of the Benzodiazepine Binding Site, Jun. 1, 1996, Molecular Pharmacology 49(6):1080-1084.*
Greenfield et al., Mutation of the GABAA Receptor M1 Transmembrane Proline Increases GABA Affinity and Reduces Barbiturate Enhancement, Mar. 2, 2002, Neuropharmacology 42(2):502-521.*
Chang et al., A Single M1 Residue in the beta2 Subunit Alters Channel Gating of GABAA Receptor in Anesthetic Modulation and Direct Activation, Oct. 31, 2003, Journal of Biological Chemistry 278(44):42821-42828.*
Akk, G., Bracamontes, J. & Steinbach, J.H. Pregnenolone sulfate block of GABA(A) receptors: mechanism and involvement of a residue in the M2 region of the alpha subunit. J. Physiol., 532:673-84 (2001).
Amin, J. and D.S. Weiss GABAA receptor needs two homologous domains of the β-subunit for activation by GABA but not by pentobarbital. Nature 366(6455): p. 565-569 (1993).Amin, J. and D.S. Weiss GABAA receptor needs two homologous domains of the β-subunit for activation by GABA but not by pentobarbital. Nature 366(6455): p. 565-569 (1993).
Bamber, B.A., Richmond, J.E., Otto, J.F. & Jorgensen, E.M. Composition of the GABA receptor at the *Caenorhabditis elegans* neuromuscular junction. Br. J. Pharmacol. 144:502-509 (2005).
Bamber, B.A., Twyman, R.E. & Jorgensen, E.M. Pharmacological characterization of the homomeric and heteromeric UNC-49 GABA receptors in *C. elegans*. Br. J. Pharmacol. 138: 883-93 (2003).
Bamber, B.A., Beg, A.A., Twyman, R.E. & Jorgensen, E.M. The *Caenorhabditis elegans* unc-49 Locus Encodes Multiple Subunits of a Heteromultimeric GABA Receptor. J. Neurosci. 19:5348-535 (1999).
Barnard, E.A., et al., International Union of Pharmacology. XV. Subtypes of gamma-aminobutyric acidA receptors: classification on the basis of subunit structure and receptor function. Pharmacol Rev 0(2): 291-313 (1998).
Baulac, S., et al., First genetic evidence of GABAA receptor dysfunction in epilepsy: a mutation in the gamma2-subunit gene. Nat Genet 28(1):46-8 (2001).
Belelli, D. & Lambert, J.J. Neurosteroids: endogenous regulators of the GABA(A) receptor. Nat. Rev. Neurosci. 6:565-75 (2005).
Belelli, D., Lambert, J.J., Peters, J.A., Wafford, K. & Whiting, P.J. The interaction of the general anesthetic etomidate with the gamma-aminobutyric acid type A receptor is influenced by a single amino acid. Proc. Natl. Acad. Sci. U.S.A. 94, 11031-6 (1997).
Beyenburg, S., et al., Neuroactive steroids and seizure susceptibility. Epilepsy Res. 44(2-3): p. 141-53 (2001).
Bianchi, M.T., Haas, K.F. & Macdonald, R.L. Structural determinants of fast desensitization and desensitization-deactivation coupling in GABAA receptors. J. Neurosci. 21, 1127-36 (2001).
Blum, D.E., New drugs for persons with epilepsy. Adv Neurol. 76:57-87 (1998).
Carlson, B.X., Engblom, A.C., Kristiansen, U., Schousboe, A. & Olsen, R.W. A single glycine residue at the entrance to the first membrane-spanning domain of the gamma-aminobutyric acid type A receptor beta(2) subunit affects allosteric sensitivity to GABA and anesthetics. Mol. Pharmacol. 57: 474-84 (2000).
Chen, C. And H. Okayama, High-efficiency transformation of mammalian cells by plasmid DNA. Mol Cell Biol. 7 (8):2745-52 (1987).
Colquhoun, D. Binding, gating, affinity and efficacy: the interpretation of structure-activity relationships for agonists and of the effects of mutating receptors. Br. J. Pharmacol. 125:924-47 (1998).
Dang, H., England, P.M., Farivar, S.S., Dougherty, D.A. & Lester, H.A. Probing the role of a conserved M1 proline residue in 5-hydroxytryptamine(3) receptor gating. Mol Pharmacol 57:1114-22 (2000).
Davis TiPS 13:35-41 (Jan. 1992).
Davis Behav. Neurosci. 100:814 (1986).
Davis Psychopharmacology 62:1 (1979).
Doyle, D.A., et al., The structure of the potassium channel: molecular basis of K+ conduction and selectivity. Science 280(5360):69-77 (1998).
England, P.M., Zhang, Y., Dougherty, D.A. & Lester, H.A. Backbone mutations in transmembrane domains of a ligand-gated ion channel: implications for the mechanism of gating. Cell 96:89-98 (1999).

(Continued)

*Primary Examiner* — John Ulm
(74) *Attorney, Agent, or Firm* — Ballard Spahr LLP

(57) ABSTRACT

Disclosed are compositions and methods related to GABA$_A$ receptors.

19 Claims, 37 Drawing Sheets

OTHER PUBLICATIONS

Etter, A., et al., Picrotoxin blockade of invertebrate glutamate-gated chloride channels: subunit dependence and evidence for binding within the pore. J Neurochem. 72(1):318-26 (1999).

French-Constant, R.H., Rocheleau, T.A., Steichen, J.C. & Chalmers, A.E. A point mutation in a Drosophila GABA receptor confers insecticide resistance. Nature 363:449-451 (1993).

Frye, C.A., The neurosteroid 3 alpha, 5 apha-THP has antiseizure and possible neuroprotective effects in an animal model of epilepsy. Brain Res 696(1-2):113-20 (1995).

Gasior, M., Carter, R.B. & Witkin, J.M. Neuroactive steroids: potential therapeutic use in neurological and psychiatric disorders. Trends Pharmacol. Sci. 20:107-112 (1999).

Gingrich, K.J., W.A. Roberts, And Kass, R.S. Dependence of the GABAA receptor gating kinetics on the alpha-subunit isoform: implications for structure-function relations and synaptic transmission. J Physiol (Lond). 489(Pt 2):529-43 (1995).

Gingrich, K.J. And P.M. Burkat, Zn2+ inhibition of recombinant GABAA receptors: an allosteric, state—dependent mechanism determined by the gamma-subunit. J Physiol 506(Pt 3):609-25 (1998).

Haas, K.F. And R.L. Macdonald, GABAA receptor subunit gamma2 and delta subtypes confer unique kinetic properties on recombinant GABAA receptor currents in mouse fibroblasts. J Physiol 514(Pt 1): p. 27-45 (1999).

Haefely, W. et al., Advances in Drug Research, Academic Press 14:165-322 (1985).

Hanner, M., et al., Binding of correolide to the K(v)1.3 potassium channel: characterization of the binding domain by site-directed mutagenesis. Biochemistry 40(39):11687-97 (2001).

Harrison, N.L., S. Vicini, And J.L. Barker, A steroid anesthetic prolongs inhibitory postsynaptic currents in cultured rat hippocampal neurons. J Neurosci 7(2):604-9 (1987).

Herzog, A.G., P. Klein, and B.J. Ransil, Three patterns of catamenial epilepsy. Epilepsia 8(10): p. 1082-1088 (1997).

Hosie et al. Nature 444:486 (2005).

Jones, M.V. And G.L. Westbrook, Desensitized states prolong GABAA channel responses to brief agonist pulses. Neuron 15(1):181-91 (1995).

Jones, M.V., Jonas, P., Sahara, Y. & Westbrook, G.L. Microscopic kinetics and energetics distinguish GABA(A) receptor agonists from antagonists. Biophys. J. 81, 2660-70 (2001).

Jones, M.V. And G.L. Westbrook, Shaping of IPSCs by endogenous calcineurin activity. J Neurosci 17(20):7626-33.

Jones, M.V., et al., Defining affinity with the GABAA receptor. J Neurosci. 18(21): 8590-604 (1998).

Kerrigan, J.F., Shields, W.D., Nelson, T.Y., Bluestone, D.L., Dodson, W.E., Bourgeois, B.F., Pellock, J.M., Morton, L.D. & Monaghan, E.P. Ganaxolone for treating intractable infantile spasms: a multicenter, open-label, add-on trial. Epilepsy Res. 42:133-9 (2000).

Kokate, T.G., et al., Convulsant actions of the neurosteroid pregnenolone sulfate in mice. Brain Res 831(1-2):119-24 (1999).

Lambert, J.J., et al., Neurosteroids and GABAA receptor function. Trends Pharmacol. Sci. 16(9): 295-303 (1995).

Laxer, K., Blum, D., Abou-Khalil, B.W., Morrell, M.J., Lee, D.A., Data, J.L. & Monaghan, E.P. Assessment of ganaxolone's anticonvulsant activity using a randomized, double-blind, presurgical trial design. Ganaxolone Presurgical Study Group. Epilepsia 41:1187-94 (2000).

Lester, H.A., Dibas, M.I., Dahan, D.S., Leite, J.F. & Dougherty, D.A. Cys-loop receptors: new twists and turns. Trends Neurosci., 27:329-36 (2004).

Lister Psychopharmacol. 92:180-185 (1987).

Howard, J. and Pollard, G. "Psychopharmacology of Anxiolytics and Antidepressants", edited by S. E. File, pp. 131-153, Raven Press, New York (1991).

Lynch, J.W., et al., Mutations affecting the glycine receptor agonist transduction mechanism convert the competitive antagonist, picrotoxin, into an allosteric potentiator. J Biol Chem 1270(23):13799-806 (1995).

Maconochie, D.J., J.M. Zempel, and J.H. Steinbach, How quickly can GABAA receptors open? Neuron 12(1):61-71 (1994).

Macdonald, R.L., C.J. Rogers, and R.E. Twyman, Kinetic properties of the GABAA receptor main conductance state of mouse spinal cord neurones in culture. J Physiol 410:479-99 (1989).

Macdonald, R.L. & Olsen, R.W. GABAA receptor channels. Ann. Rev. Neurosci. 17:569-602 (1994).

Maitra, R. And J.N. Reynolds, Modulation of GABAA receptor function by neuroactive steroids: evidence for heterogeneity of steroid sensitivity of recombinant GABAA receptor isoforms. Can J Physiol Pharmacol 76(9):909-20 (1998).

Majewska, M.D. Neurosteroids: Endogenous Bimodal Modulators of the GABAA Receptor. Mechanism of Action and Physiological Significance. Progress in Neuorobiology 38:379-395 (1992).

Mcclellan, A.M. And R.E. Twyman, Receptor system response kinetics reveal functional subtypes of native murine and recombinant human GABAA receptors. J Physiol 515(Pt 3):711-27 (1999).

McIntire, S.L., E. Jorgensen, And H.R. Horvitz, Genes required for GABA function in *Caenorhabditis elegans*. Nature 364(6435):334-337 (1993b).

Mellon, S.H. & Griffin, L.D. Neurosteroids: biochemistry and clinical significance. Trends. Endocrinol. Metab. 13:35-43 (2002)

Mienville, J.M. And S. Vicini, Pregnenolone sulfate antagonizes GABAA receptor-mediated currents via a reduction of channel opening frequency. Brain Res 489(1):190-4 (1989).

Mihic, S.J., Ye, Q., Wick, M.J., Koltchine, V.V., Krasowski, M.D., Finn, S.E., Mascia, M.P., Valenzuela, C.F., Hanson, K.K., Greenblatt, E.P., Harris, R.A. & Harrison, N. L. Sites of alcohol and volatile anaesthetic action on GABAA and glycine receptors. Nature 389:385-389 (1997).

Mistry, D.K. And G.A. Cottrell, Actions of steroids and bemegride on the GABAA receptor of mouse spinal neurones in culture. Exp Physiol 75(2):199-209 (1990).

Mitcheson, J.S.; et al., A structural basis for drug-induced long QT syndrome. Proc Natl Acad Sci U S A 97 (22):12329-33 (2000).

Miyazawa, A., Fujiyoshi, Y. & Unwin, N. Structure and gating mechanism of the acetylcholine receptor pore. Nature 423:949-55 9 (2003).

Mohler, H. Arzneim.-Forsch./Drug Res. 42 (2a):211 (1992).

Morris, K.D. & Amin, J. Insight into the mechanism of action of neuroactive steroids. Mol. Pharmacol. 66:56-69 (2004).

Morris, K.D., C.N. Moorelfield, And J. Amin, Differential modulation of the gamma-aminobutyric acid type C receptor by neuroactive steroids, Mol Pharmacol 56(4): p. 752-759 (1999).

Morrow, A.L., Khisti, R., Tokunaga, S., McDaniel, J.R. & Matthews, D.B. GABAergic neuroactive steroids modulate selective ethanol actions: mechanisms and significance. In Neurosteroid effects in the central nervous system. ed Smith, S.S. pp. 219-245. Boca Raton, FL: CRC Press (2004).

Mozrzymas, J.W., et al., Chlorpromazine inhibits miniature GABAergic currents by reducing the binding and by increasing the unbinding rate of GABAA receptors. J Neurosci. 19(7):2474-88 (1999).

Nilsson, K.R., Zorumski, C.F. & Covey, D.F. Neurosteroid analogues. 6. The synthesis and GABAA receptor pharmacology of enantiomers of dehydroepiandrosterone sulfate, pregnenolone sulfate, and (3a,5b)-3-hydroxypregnan-20-one sulfate. J. Med. Chem. 41:2604-2613 (1998).

Olsen, R.W. & Tobin, A.J. Molecular biology of GABAA receptors. FASEB J. 4:1469-1480 (1990).

Park-Chung, M., Malayev, a., Purdy, R.H., Gibbs, T.T. & Farb, D.H. Sulfated and unsulfated steroids modulate gamma-aminobutyric acidA receptor function through distinct sites. Brain Res. 830:72-87 (1999).

Paul, S.M. & Purdy, R.H. Neuroactive steroids. FASEB J., 6, 2311-22 (1992).

Pistis, M., et al., Complementary regulation of anaesthetic activation of human ($\alpha 6\beta 3$ y2L) and Drosophila (RDL) GABA receptors by a single amino acid residue. J Physiol (Lond) 515(Pt 1):3-18 (1999).

Pribilla, I., et al., The atypical M2 segment of the beta subunit confers picrotoxinin resistance to inhibitory glycine receptor channels [published erratum appears in EMBO J Mar. 15, 1994; 13(6):1493]. Embo J. 11(12):4305-11 (1992).

Puia, G. et al. Molecular Pharm. 39:691 (1991).

Puia, G., et al., Neurosteroids act on recombinant human GABAA receptors. Neuron. 4(5):759-65 (1990).

Rajendra, S., Lynch, J.W., Pierce, K.D., French, C.R., Barry, P.H. & Schofield, P.R. Mutation of an arginine residue in the human glycine receptor transforms beta-alanine and taurine from agonists into competitive antagonists. Neuron 14:169-175 (1995).

Reddy, D.S. And M.A. Rogawski, Enhanced anticonvulsant activity of ganaxolone after neurosteroid withdrawal in a rat model of catamenial epilepsy. J Pharmacol Exp Ther 294(3):909-15 (2000).

Rick, C.E., et al., Neurosteroids act on the GABAA receptor at sites on the N-terminal side of the middle of TM2. Neuroreport 9(3):379-383 (1998).

Rupprecht, R. Neuroactive steroids: mechanisms of action and neuropsychopharmacological properties. Psychoneuroendocrinology 28:139-68 (2003).

Sali, A. & Blundell, T.L. Comparative protein modelling by satisfaction of spatial restraints. J. Mol. Biol. 234:779-815 (1993).

Shen, W., Mennerick, S., Zorumski, E.C., Covey, D.F. & Zorumski, C.F. Pregnenolone sulfate and dehydroepiandrosterone sulfate inhibit GABA-gated chloride currents in *Xenopus oocytes* expressing picrotoxin-insensitive GABAA receptors. Neuropharmacology 38:267-271 (1999).

Shen, W., et al., Pregnenolone sulfate modulates inhibitory synaptic transmission by enhancing GABAA receptor desensitization. J Neurosci 20(10):p. 3571-9 (2000).

Takada, S. et al. J. Med. Chem. 31:1738 (1988).

Skolnick, P. et al., GABA and Benzodiazepine Receptors, Squires, R., Ed., pp. 99-102 (1987).

Thompson, J.D., Higgins, D.G. & Gibson, T.J. CLUSTAL W: improving the sensitivity of progressive multiple sequence alignment through sequence weighting, position-specific gap penalties and weight matrix choice. Nucleic Acids Res. 22:4673-4680 (1994).

Twyman, R.E. and R.L. Macdonald, Neurosteroid regulation of GABAA receptor single-channel kinetic properties of mouse spinal cord neurons in culture. J Physiol. 456:215-45 (1992.).

Twyman, R.E., C.J. Rogers, And R.L. Macdonald, Intraburst kinetic properties of the GABAA receptor main conductance state of mouse spinal cord neurones in culture. J. Physiol. 423:193-220 (1990).

Ueno, S., et al., Bicuculline and gabazine are allosteric inhibitors of channel opening of the GABAA receptor. J. Neurosci. 17(2): p. 625-634 (1997).

Vallee, M., Mayo, W., Damaudery, M., Corpechot, C., Young, J., Koehl, M., Le Moal, M., Baulieu, E.E., Robel, P. & Simon, H. Neurosteroids: deficient cognitive performance in aged rats depends on low pregnenolone sulfate levels in the hippocampus. Proc. Natl. Acad. Sci. U.S.A. 94:14865-14870 (1997).

Walker, M.C. and J.W. Sander, New anti-epileptic drugs. Expert Opin Investig Drugs 8(10): p. 1497-1510 (1999).

Wallace, R.H., et al., Mutant GABAA receptor gamma2-subunit in childhood absence epilepsy and febrile seizures. Nat Genet 28(1):49-52 (2001).

Wardell, B. et al. "Residues in the first transmembrane domain of the *Caenorhabditis elegans* GABAA receptor confer sensitivity to to neurosteroid pregnenolone sulfate." Br. J. Pharmacol. 148:162-172 (2006).

VVieboldt et al., Anal. Chem., 69:1683-1691 (1997).

Wooltorton, J.R., S.J. Moss, and T.G. Smart, Pharmacological and physiological characterization of murine homomeric Beta GABAA receptors. Eur J Neurosci. 9(11):2225-2235 (1997).

Wu, F.S., Gibbs, T.T. & Farb, D.H. Pregnenolone sulfate: a positive allosteric modulator at the N-methyl-D-aspartate receptor. Mol. Pharmacol. 40:333-6 (1991).

Zaman, S.H., Shingai, R., Harvey, R.J., Darlison, M.G. & Barnard, E.A. Effects of subunit types of the recombinant GABAA receptor on the response to a neurosteroid. Eur. J. Pharmacol. 225:321-30 (1992).

Zhu, W.J. and S. Vicini, Neurosteroid prolongs GABAA channel deactivation by altering kinetics of desensitized states. J. Neurosci. 17:4022-4031 (1997).

Zhu, W.J., et al., Delta subunit inhibits neurosteroid modulation of GABAA receptors. J Neurosci. 16(21):6648-56 (1996).

International Search Report and Written Opinion mailed Mar. 25, 2008 re International Application No. PCT/US07/12089.

* cited by examiner

|  |  | M1 |  | M2 |  |
|---|---|---|---|---|---|
| UNC-49B | 255 | FYTMN—VIPS—LIVT—ISWVSFWLNREASPARVGLGVTTVLTMTT | 298 |
| UNC-49C | 256 | FYFLQ—IFFPASLVVVLSW—ISFWINRDSAPSRTLIGTMTVLTETH | 299 |
| rat GABA$_A$ α1 | 251 | YFVI—QTYLPC—IMTV—LSQVSFWLNRESVPARTVFGVTTVLTMTT | 294 |
| rat GABA$_A$ β1 | 244 | YFILQTYMPSTL—ITT—VLSWVSFWINYDASAARVALGITTVLTMTT | 287 |
| rat GABA$_A$ γ1 | 273 | YFTIQTY—PCILTVVLSWVSFWINKDAVPARTSLGITTVLTMTT | 317 |

|  |  | M3 |  |
|---|---|---|---|
| UNC-49B | 299 | LITTTNSMPKVSYVKGLDVFLNFCFVMVFASLLEYAIVSY | 339 |
| UNC-49C | 300 | LMTGTNRRLPPVAYKAVDVFLGFCYLLV—LALIEYACVAY | 340 |
| rat GABA$_A$ α1 | 306 | LSISARNSLPKVAYATAMDWFIAVCYAFVFSALIEFATVNY | 335 |
| rat GABA$_A$ β1 | 289 | ISTHLRETLPKIPYVKAIDIYLMGCCFVFVFLALLEYAFVNY | 328 |
| rat GABA$_A$ γ1 | 318 | LSTIARKSLPKVSYVTAMDLFVSVCFIFVFAALMEYGTLHY | 357 |

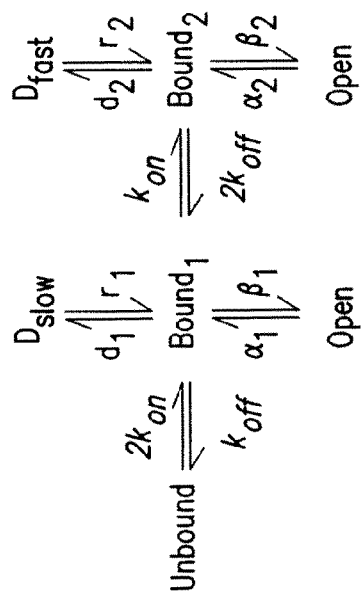
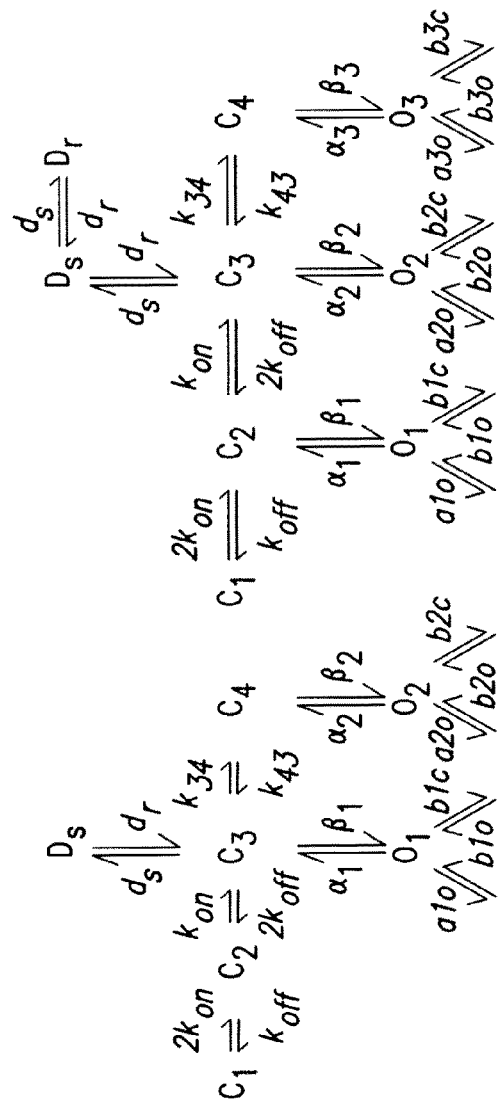
FIG.11C
FIG.11D

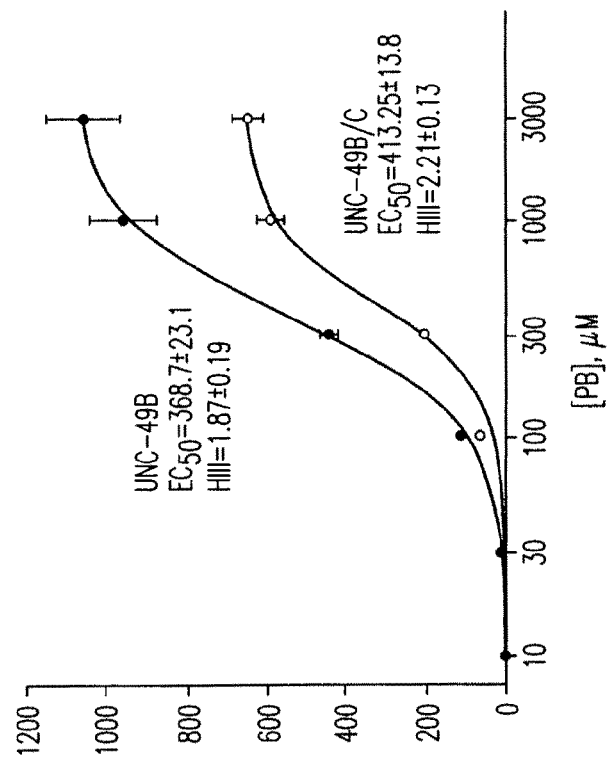
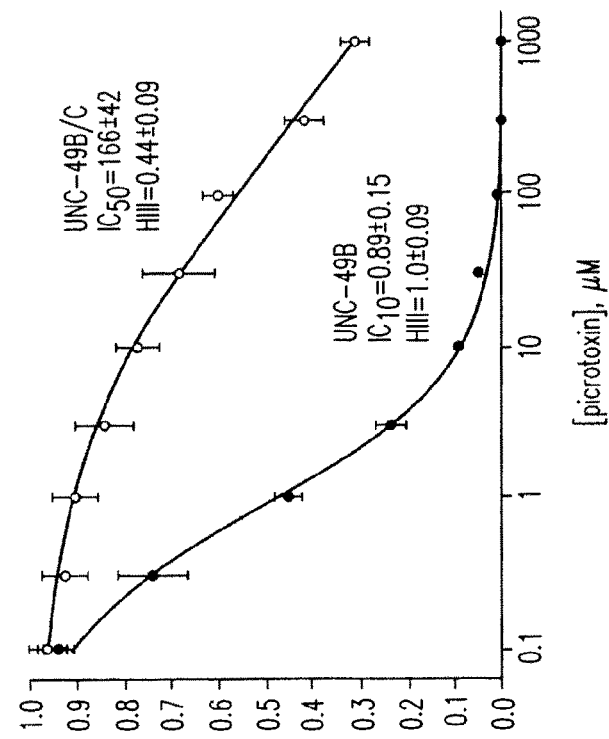
FIG. 14A
FIG. 14B

|         |     | M1                              |                                 | M2                              |     |
|---------|-----|---------------------------------|---------------------------------|---------------------------------|-----|
| UNC-49B | 255 | F Y T M N I V I P S I L I V T I | S W V S F W L N R E A S P A R V G L G V T T V L T M T T | 298 |
| UNC-49C | 256 | F Y F L Q F F P A S L V V V L S | S W I S F W L N R D S A P S R T L I G T M T V L T M T T | 299 |
| rat GABA_A α1 | 251 | Y F V I Q T Y L P C I M T V I L S | Q V S F W L N R E S V P A R T V F G V T T V L T M T T | 294 |
| rat GABA_A β1 | 244 | Y F I L Q T Y M P S T L I T I L T | V V L S W V S F W I N Y D A S A A R V A L G I T T V L T M T T | 287 |
| rat GABA_A γ1 | 273 | Y F T I Q T Y I P C I L T V V L S | W V S F W I N K D A V P A R T S L G I T T V L T M T T | 317 |

|         |     |                                 | M3                              |                                 |     |
|---------|-----|---------------------------------|---------------------------------|---------------------------------|-----|
| UNC-49B | 299 | L I T T T N N S M P K V S Y V K G L D | V F L N F C F V M V F A S L L E Y A I V S Y | 339 |
| UNC-49C | 300 | L M T G T N N R R L P P V A Y Y K A V | D V F L G F C Y L L V I L A L I E Y A C V A Y | 340 |
| rat GABA_A α1 | 306 | L S I S A R N S L P K V A Y A T A M D W | F I A V C Y A F V F S A L I E F A T V N Y | 335 |
| rat GABA_A β1 | 289 | I S T H L R E T L P K I P Y V K A I D I | Y L M G C F V F V F L A L L E Y A F V N Y | 328 |
| rat GABA_A γ1 | 318 | L S T I A R K S L P K V S Y V T A M D L | F V S V C F I F V F A A L M E Y G T L H Y | 357 |

FIG.17A (block a)
```
MWGLAGGRLFGIFSAPVLVAVVC----CAQSVN
M-----ARPFTLIV--LLSAHLCLHVVVTQDED DPGNMSFVKETVDKLLK--GYDIRLRPDFGGPP
SHINTQLLSSVLDRLTNRTTYDKRLRPRYGEKP
                              GBD    (b)
VCVGMNIDIASIDMVSEVNMDYTLTMYFQQYWR
VDVGITIHVSSISAVSEVDMDFTLDFYMRQTWQ
          (block c)
DKRLAYSGIPL-------NLTLDNRVADQLWVP
DPRLAFGSLDLGLSKEIDSLTVGVDYLDRLWKP DTYFLNDKKSFVHGVTVKNRMIRLHPDGTVLYG
DTFFPNEKKSFFHLATTHNSFLRIEGDGTVYTS
(block d)    c-c loop    (block e)  BDI
LRITTTAACMMDLRRYPLDEQNCTLEIESYGYT
QRLTVTATCPMDLKLFPMDSQHCKLEIESYGYE
            (block f)
TDDIEFYW--RGGDKAVTGV--ERIELPQFSIV
TKDIDYYWGKKRTDLEITAVKFDTFQLPQFQPT
                BDII         (block g)
EHRLVSRNVVFATGAYPRLSLSFRLKRNIGYFI
LYFVNTTKAETSSGKYVRLALEVILVRNMGFYT
(block I)    M1                    (block II) M2
LQTYMPSILITILSWVSFWINYDASAARVALGI
MNIVIPSILIVTISWVSFWLNREASPARVGLGV
                    (block III)
TTVLTMTTINTHLRETLPKIPYVKAIDMYLMGC
TTVLTMTTLITTTNNSMPKVSYVKGLDVFLNFC
(block IV)    M3            (block V)
FVFVFLALLEYAFVNYIFFGRGPQRQKKLAEKT
FVMVFASLLEYAIVSYM--------NKRLVLRR
        (block VI)    M4
NAIDRWSRIVFPFTFSLFNLVYWLY--Y-----
K-IDKLSRYGFPLSFSIFNIVYWLYMKYLSLNS
```

FIG.26

GABA and neurosteroid sensities of wild-type and mutated GABA$_A$ receptors from *C. elegans*, expressed in mammalian HEK fibroblast cells.

SEQUENCE LISTING

<160> NUMBER OF SEQ ID NOS: 50

<210> SEQ ID NO 1
<211> LENGTH: 506
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 1

```
Met Ala Arg Pro Phe Thr Leu Ile Val Leu Leu Ser Ala His Leu Cys
1               5                   10                  15

Leu His Val Val Thr Gln Asp Glu Asp Ser His Ile Asn Thr Gln
            20                  25                  30

Leu Leu Ser Ser Val Leu Asp Arg Leu Thr Asn Arg Thr Tyr Asp
        35                  40                  45

Lys Arg Leu Arg Pro Arg Tyr Gly Glu Lys Pro Val Asp Val Gly Ile
50                  55                  60

Thr Ile His Val Ser Ser Ile Ser Ala Val Ser Glu Val Asp Met Asp
65                  70                  75                  80

Phe Thr Leu Asp Phe Tyr Met Arg Gln Thr Trp Gln Asp Pro Arg Leu
                85                  90                  95

Ala Phe Gly Ser Leu Asp Leu Gly Leu Ser Lys Glu Ile Asp Ser Leu
            100                 105                 110

Thr Val Gly Val Asp Tyr Leu Asp Arg Leu Trp Lys Pro Asp Thr Phe
        115                 120                 125

Phe Pro Asn Glu Lys Lys Ser Phe Phe His Leu Ala Thr Thr His Asn
130                 135                 140

Ser Phe Leu Arg Ile Glu Gly Asp Gly Thr Val Tyr Thr Ser Gln Arg
145                 150                 155                 160

Leu Thr Val Thr Ala Thr Cys Pro Met Asp Leu Lys Leu Phe Pro Met
                165                 170                 175

Asp Ser Gln His Cys Lys Leu Glu Ile Glu Ser Tyr Gly Tyr Glu Thr
            180                 185                 190

Lys Asp Ile Asp Tyr Tyr Trp Gly Lys Lys Arg Thr Asp Leu Glu Ile
        195                 200                 205

Thr Ala Val Lys Phe Asp Thr Phe Gln Leu Pro Gln Phe Gln Pro Thr
    210                 215                 220

Leu Tyr Phe Val Asn Thr Thr Lys Ala Glu Thr Ser Ser Gly Lys Tyr
225                 230                 235                 240

Val Arg Leu Ala Leu Glu Val Ile Leu Val Arg Asn Met Gly Phe Tyr
                245                 250                 255

Thr Met Asn Ile Val Ile Pro Ser Ile Leu Ile Val Thr Ile Ser Trp
            260                 265                 270

Val Ser Phe Trp Leu Asn Arg Glu Ala Ser Pro Ala Arg Val Gly Leu
        275                 280                 285
```

```
Gly Val Thr Val Leu Thr Met Thr Thr Leu Ile Thr Thr Thr Asn
            290                 295                 300

Asn Ser Met Pro Lys Val Ser Tyr Val Lys Gly Leu Asp Val Phe Leu
305                 310                 315                 320

Asn Phe Cys Phe Val Met Val Phe Ala Ser Leu Leu Glu Tyr Ala Ile
                325                 330                 335

Val Ser Tyr Met Asn Lys Arg Leu Val Leu Arg Arg Glu Lys Arg Arg
            340                 345                 350

Lys Ala Ala Glu Gln Gln Arg Asn Glu Met Pro Met Phe Asn Ala
                355                 360                 365

Ser Pro Lys Ala Ala Asn Asn Ser Tyr Glu Met Thr Leu Met Ser
370                 375                 380

Gln Asn Ser Thr Pro Ala Lys Ser Tyr Val Gln Ala Asp Leu Tyr Phe
385                 390                 395                 400

Ala Gly His Asn Ser Ser Met Asn Pro Leu Met Glu Ile Pro Glu Asn
                405                 410                 415

Cys Asp Cys Arg Thr Ile Pro Met Met Gln His Pro Arg Leu Val Thr
                420                 425                 430

Asp Gly Ala His Thr Leu Trp Pro Ala Pro Phe Ala Arg Pro Lys Lys
            435                 440                 445

Ala Ser Lys Thr Cys Cys Gln Arg Trp Thr Pro Ala Lys Ile Asp Lys
450                 455                 460

Leu Ser Arg Tyr Gly Phe Pro Leu Ser Phe Ser Ile Phe Asn Ile Val
465                 470                 475                 480

Tyr Trp Leu Tyr Met Lys Tyr Leu Ser Leu Asn Ser Ser Asp Lys Ile
                485                 490                 495

Gln Glu Asn Asp Lys Trp Gln Gln Ile His
            500                 505

<210> SEQ ID NO 2
<211> LENGTH: 2601
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 2
aagtttgaga gtgatatagg agaaaaacct ccccaacatt ggctcacacc cggattatga      60
tcttctgctg ctcctgctgc tccttctgct gtagttgaga cgaagaagaa gaagaagctc     120
cattctcgag aaatggctcg tccattcaca cttatcgtac tcctctccgc acatctgtgt     180
ctacatgtgg ttgtgacaca ggatgaggac tcacatatca acactcaact cctctcatca     240
gttctcgata gactcacgaa tcgcactact tatgataaaa gattacggcc caggtatggt     300
gaaaagccag tcgacgttgg aattacgata cacgtttctt caatctctgc agtttcagaa     360
gttgatatgg acttcacatt agacttctac atgcgtcaaa cgtggcaaga ccctcgacta     420
gccttcggaa gtcttgattt gggactttcc aaagaaatcg actcacttac cgtcggagta     480
gactacctga tagactgtg aaacccgac acgttcttcc caaatgaaaa gaaatcattc     540
ttccacttgg caaccacaca taactcgttc cttcgtatcg agggtgatgg aacggtttat     600
actagtcaaa gattaacagt cactgcaacg tgtccaatgg acctgaagct gttcccaatg     660
gactctcaac actgtaaact ggaaattgaa agctacgggt acgagacgaa agatatcgac     720
tactattggg gaagaagcg gactgatttg gagataacgg ctgtcaagtt tgataccttc     780
cagttgccgc agtttcagcc aacgctgtat tttgtgaata caactaaagc cgagacctca     840
```

```
tcaggaaaat acgtacgcct ggcgctggaa gtaatattgg ttcgaaatat gggcttctac    900
actatgaaca tcgtcatccc atccatcctg atcgtcacca tatcttgggt atcattttgg    960
ttgaatcgag aagcttcgcc ggctcgagtt ggattgggtg tgactactgt gctcacaatg   1020
acaactctga tcactacaac caataattcg atgccaaaag tgtcttatgt caagggtctg   1080
gatgtgtttc ttaattttg tttcgtaatg gtattcgcct cgttgctcga gtacgccata   1140
gtatcctaca tgaataaacg actggtcctc cgacgggaaa acgaagaaa agccgccgaa    1200 caacagcagc gaaacgagat gccaatgttc aacgcgagcc cgaaggccgc caataataat   1260
tcatacgaaa tgcacttat gtcgcaaaat tcgacgcctg ccaaaagcta tgtacaggct    1320
gacttgtact ttgccggaca caattcctct atgaatccat tgatggagat cccagaaaat   1380
tgtgattgcc ggacgattcc aatgatgcaa catccacgtc ttgtcacaga cggcgcacat   1440
acgctatggc cggctccatt cgcgcggccg aaaaaggctt ccaagacatg ctgccaacga   1500
tggacgcctg caaaaatcga taagcttagc cgatacggtt tcccattgtc tttctctatc   1560
ttcaatatag tctactggtt gtatatgaaa tatctaagct taaactcgtc ggacaagatc   1620
caggagaacg acaagtggca gcagatccac tgatgcgtat tcgacggccg aaatcgagta   1680
caaatggtgt acgtcgaagg agccgaattg ttcgacagcg gtcaaggccg acgcgaacat   1740
cgaactgtcg agttataaat tcactaaaat ctgccaaaaa cggacacttg ccagcacttc   1800
atcggggacc tactctcgtc tacgggttag tttcatattt gatcgcgaca gcggcttcta   1860 cttcttcaa atattttcc ctgccagcct cgtcgtagtt ttatcatgga tctcattctg    1920
gatcaatcgt gactcggcgc cttcgcgaac cctaatcggt acgatgacgg tgctcactga   1980
gactcatctt atgaccggaa ccaatcgacg tcttccacca gttgcctatg taaaagccgt   2040
tgatgtattc ctcggttct gctatcttct ggttatactg gcgttgatcg agtacgcctg    2100
tgttgcctac tcaaaaaaga agaacgagga tcgtcggaga agagagaaga agacggagca   2160
taaacctgct ccgccgacac ctgatattct tcacgacgtc cgccttgccg aatgcacatg   2220
caacgcggct ccaacctcga tcatcgccgt catcaagcag tcgaatcgat tctgtgtcag   2280
tcacagtcac attgacatcg tcagccgtgc cgcgtttcct cttgttttca tcttgttcaa   2340
cactctcttc tggctgattc tactgtacaa atccaagcgt ctgccgtata ttagtgaaca   2400
cgagggtgac cgttgcgatg ctccagacct tcattaatct caatccaact tcctcatcat   2460
tttccatttc gaatatctct tttttcttgca cagaagcctt ttttcgtttt tttttattga   2520
tttattttta cggattttta gataatgcac agatgcctca ttgctcaaat aaatttattt   2580
taattaaaaa aaaaaaaaaa a                                             2601
```

<210> SEQ ID NO 3
<211> LENGTH: 448
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 3

Met Ala Arg Pro Phe Thr Leu Ile Val Leu Leu Ser Ala His Leu Cys
1               5                   10                  15

Leu His Val Val Val Thr Gln Asp Glu Asp Ser His Ile Asn Thr Gln
            20                  25                  30

Leu Leu Ser Ser Val Leu Asp Arg Leu Thr Asn Arg Thr Thr Tyr Asp
        35                  40                  45

```
Lys Arg Leu Arg Pro Arg Tyr Gly Glu Lys Pro Val Asp Gly Ile
 50                  55                  60
Thr Ile His Val Ser Ser Ile Ser Ala Val Ser Glu Val Asp Met Asp
 65                  70                  75                  80
Phe Thr Leu Asp Phe Tyr Met Arg Gln Thr Trp Gln Asp Pro Arg Leu
                 85                  90                  95
Ala Phe Gly Ser Leu Asp Leu Gly Leu Ser Lys Glu Ile Asp Ser Leu
            100                 105                 110
Thr Val Gly Val Asp Tyr Leu Asp Arg Leu Trp Lys Pro Asp Thr Phe
        115                 120                 125
Phe Pro Asn Glu Lys Lys Ser Phe Phe His Leu Ala Thr Thr His Asn
    130                 135                 140
Ser Phe Leu Arg Ile Glu Gly Asp Gly Thr Val Tyr Thr Ser Gln Arg
145                 150                 155                 160
Leu Thr Val Thr Ala Thr Cys Pro Met Asp Leu Lys Leu Phe Pro Met
                165                 170                 175
Asp Ser Gln His Cys Lys Leu Glu Ile Glu Ser Tyr Ala Tyr Ser Thr
            180                 185                 190
Ala Glu Ile Glu Tyr Lys Trp Cys Thr Ser Lys Glu Pro Asn Cys Ser
        195                 200                 205
Thr Ala Val Lys Ala Asp Ala Asn Ile Glu Leu Ser Ser Tyr Lys Phe
    210                 215                 220
Thr Lys Ile Cys Gln Lys Arg Thr Leu Ala Ser Thr Ser Ser Gly Thr
225                 230                 235                 240
Tyr Ser Arg Leu Arg Val Ser Phe Ile Phe Asp Arg Asp Ser Gly Phe
                245                 250                 255
Tyr Phe Leu Gln Ile Phe Phe Pro Ala Ser Leu Val Val Val Leu Ser
            260                 265                 270
Trp Ile Ser Phe Trp Ile Asn Arg Asp Ser Ala Pro Ser Arg Thr Leu
        275                 280                 285
Ile Gly Thr Met Thr Val Leu Thr Glu Thr His Leu Met Thr Gly Thr
    290                 295                 300
Asn Arg Arg Leu Pro Pro Val Ala Tyr Val Lys Ala Val Asp Val Phe
305                 310                 315                 320
Leu Gly Phe Cys Tyr Leu Leu Val Ile Leu Ala Leu Ile Glu Tyr Ala
                325                 330                 335
Cys Val Ala Tyr Ser Lys Lys Asn Glu Asp Arg Arg Arg Glu
            340                 345                 350
Lys Lys Thr Glu His Lys Pro Ala Pro Thr Pro Asp Ile Leu His
            355                 360                 365
Asp Val Arg Leu Ala Glu Cys Thr Cys Asn Ala Ala Pro Thr Ser Ile
    370                 375                 380
Ile Ala Val Ile Lys Gln Ser Asn Arg Phe Cys Val Ser His Ser His
385                 390                 395                 400
Ile Asp Ile Val Ser Arg Ala Ala Phe Pro Leu Val Phe Ile Leu Phe
                405                 410                 415
Asn Thr Leu Phe Trp Leu Ile Leu Leu Tyr Lys Ser Lys Arg Leu Pro
            420                 425                 430
Tyr Ile Ser Glu His Glu Gly Asp Arg Cys Asp Ala Pro Asp Leu His
        435                 440                 445

<210> SEQ ID NO 4
<211> LENGTH: 1652
<212> TYPE: DNA
<213> ORGANISM: Artificial Sequence
```

<220> FEATURE:
<223> OTHER INFORMATION: Description of Artificial Sequence: Note = Synthetic Construct

<400> SEQUENCE: 4

```
cggaaaaacc tccccaacat tggctcacac ccggattatg atcttctgct gctcctgctg      60
ctccttctgc tgtagttgag acgaagaaga agaagaagct ccattctcga gaaatggctc     120
gtccattcac acttatcgta ctcctctccg cacatctgtg tctacatgtg ttgtgacac      180
aggatgagga ctcacatatc aacactcaac tcctctcatc agttctcgat agactcacga     240
atcgcactac ttatgataaa agattacggc caggtatgg tgaaaagcca gtcgacgttg      300
gaattacgat acacgtttct tcaatctctg cagtttcaga agttgatatg gacttcacat     360
tagacttcta catgcgtcaa acgtggcaag accctcgact agccttcgga agtcttgatt     420
tgggactttc caaagaaatc gactcactta ccgtcggagt agactacctg atagactgt      480
ggaaacccga cacgttcttc ccaaatgaaa agaaatcatt cttccacttg caaccacac     540
ataactcgtt ccttcgtatc gagggtgatg aacggttta ctagtcaa agattaacag        600
tcactgcaac gtgtccaatg gacctgaagc tgttcccaat ggactctcaa cactgtaaac      660
tggaaattga aagctatgcg tattcgacgg ccgaaatcga gtacaaatgg tgtacgtcga     720
aggagccgaa ttgttcgaca gcggtcaagg ccgacgcgaa catcgaactg tcgagttata     780
aattcactaa aatctgccaa aaacggacac ttgccagcac ttcatcgggg acctactctc     840
gtctacgggt tagtttcata tttgatcgcg acagcggctt ctactttctt caaatatttt     900
tccctgccag cctcgtcgta gttttatcat ggatctcatt ctggatcaat cgtgactcgg     960
cgccttcgcg aaccctaatc ggtacgatga cggtgctcac tgagactcat cttatgaccg    1020
gaaccaatcg acgtcttcca ccagttgcct atgtaaaagc cgttgatgta ttcctcggtt    1080
tctgctatct tctggttata ctggcgttga tcgagtacgc ctgtgttgcc tactcaaaaa    1140
agaagaacga ggatcgtcgg agaagagaga agaagacgga gcataaacct gctccgccga    1200
cacctgatat tcttcacgac gtccgccttg ccgaatgcac atgcaacgcg gctccaacct    1260
cgatcatcgc cgtcatcaag cagtcgaatc gattctgtgt cagtcacagt cacattgaca    1320
tcgtcagccg tgccgcgttt cctcttgttt tcatcttgtt caacactctc ttctggctga    1380
ttctactgta caaatccaag cgtctgccgt atattagtga acacgagggt gaccgttgcg    1440
atgctccaga ccttcattaa tctcaatcca acttcctcat catttccat ttcgaatatc      1500
tcttttttctt gcacagaagc cttttttcgt tttttttttat tgatttattt ttacggattt    1560
ttagataatg cacagatgcc tcattgctca aataaattta ttttaattgt cgaaaaaaaa    1620
aaaaaaaaa aaaaaaaaa aaaaaaaaaa aa                                     1652
```

<210> SEQ ID NO 5
<211> LENGTH: 85
<212> TYPE: PRT
<213> ORGANISM: Artificial Sequence
<220> FEATURE:
<223> OTHER INFORMATION: Description of Artificial Sequence : Note = Synthetic Construct

<400> SEQUENCE: 5

```
Phe Tyr Thr Met Asn Ile Val Ile Pro Ser Ile Leu Ile Val Thr Ile
1               5                   10                  15

Ser Trp Val Ser Phe Trp Leu Asn Arg Glu Ala Ser Pro Ala Arg Val
            20                  25                  30
```

Gly Leu Gly Val Thr Thr Val Leu Thr Met Thr Thr Leu Ile Thr Thr
            35                  40                  45

Thr Asn Ser Met Pro Lys Val Ser Tyr Val Lys Gly Leu Asp Val
 50                  55                  60

Phe Leu Asn Phe Cys Phe Val Met Val Phe Ala Ser Leu Leu Glu Tyr
 65                  70                  75                  80

Ala Ile Val Ser Tyr
                85

<210> SEQ ID NO 6
<211> LENGTH: 83
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 6

Phe Tyr Phe Leu Gln Ile Phe Phe Pro Ala Ser Leu Val Val Val Leu
 1               5                  10                  15

Ser Trp Ile Ser Phe Trp Ile Asn Arg Asp Ser Ala Pro Ser Arg Thr
                20                  25                  30

Leu Ile Gly Thr Met Thr Val Leu Thr Glu Thr His Leu Met Thr Gly
            35                  40                  45

Thr Asn Arg Arg Leu Pro Pro Val Ala Tyr Val Lys Asp Val Phe Leu
 50                  55                  60

Gly Phe Cys Tyr Leu Leu Val Ile Leu Ala Leu Ile Glu Tyr Ala Cys
 65                  70                  75                  80

Val Ala Tyr

<210> SEQ ID NO 7
<211> LENGTH: 85
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 7

Tyr Phe Val Ile Gln Thr Tyr Leu Pro Cys Ile Met Thr Val Ile Leu
 1               5                  10                  15

Ser Gln Val Ser Phe Trp Leu Asn Arg Glu Ser Val Pro Ala Arg Thr
                20                  25                  30

Val Phe Gly Val Thr Thr Val Leu Thr Met Thr Thr Leu Ser Ile Ser
            35                  40                  45

Ala Arg Asn Ser Leu Pro Lys Val Ala Tyr Ala Thr Ala Met Asp Trp
 50                  55                  60

Phe Ile Ala Val Cys Tyr Ala Phe Val Phe Ser Ala Leu Ile Glu Phe
 65                  70                  75                  80

Ala Thr Val Asn Tyr
                85

<210> SEQ ID NO 8
<211> LENGTH: 85
<212> TYPE: PRT
<213> ORGANISM: Artificial Sequence
<220> FEATURE:
<223> OTHER INFORMATION: Description of Artificial Sequence: Note =
      Synthetic Construct

```
<400> SEQUENCE: 8

Tyr Phe Ile Leu Gln Thr Tyr Met Pro Ser Thr Leu Ile Thr Ile Leu
1               5                   10                  15

Ser Trp Val Ser Phe Trp Ile Asn Tyr Asp Ala Ser Ala Ala Arg Val
            20                  25                  30

Ala Leu Gly Ile Thr Thr Val Leu Thr Met Thr Thr Ile Ser Thr His
        35                  40                  45

Leu Arg Glu Thr Leu Pro Lys Ile Pro Tyr Val Lys Ala Ile Asp Ile
    50                  55                  60

Tyr Leu Met Gly Cys Phe Val Phe Val Phe Leu Ala Leu Leu Glu Tyr
65                  70                  75                  80

Ala Phe Val Asn Tyr
                85

<210> SEQ ID NO 9
<211> LENGTH: 87
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 9

Tyr Phe Thr Ile Gln Thr Tyr Ile Pro Cys Ile Leu Thr Val Val Leu
1               5                   10                  15

Ser Trp Val Ser Phe Trp Ile Asn Lys Asp Ala Val Pro Ala Arg Thr
            20                  25                  30

Ser Leu Gly Ile Thr Thr Val Leu Thr Met Thr Thr Leu Ser Thr Ile
        35                  40                  45

Ala Arg Lys Ser Leu Pro Lys Val Ser Tyr Val Thr Ala Met Asp Leu
    50                  55                  60

Asp Leu Phe Val Ser Val Cys Phe Ile Leu Val Phe Ala Ala Leu Met
65                  70                  75                  80

Glu Tyr Gly Thr Leu His Tyr
                85

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 10

Phe Tyr Thr Met Asn Ile Val Ile Pro Ser Ile Leu Ile Val Thr Ile
1               5                   10                  15

Ser Trp Val Ser Phe Trp Leu Asn Arg Glu Ala Ser
            20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Note =
      Synthetic Construct
```

```
<400> SEQUENCE: 11

Phe Tyr Phe Leu Gln Ile Phe Phe Pro Ala Ser Leu Val Val Val Leu
1               5                   10                  15

Ser Trp Ile Ser Phe Trp Ile Asn Arg Asp Ser Ala
            20                  25

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 12

Ile Ile Thr Ile Val
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 13

Ser Val Val Leu Ile
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 14

Ser Ile Thr Ile Val
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 15

Ile Val Thr Ile Val
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 16

Ile Ile Val Ile Val
1               5
```

```
<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 17

Ile Ile Thr Leu Val
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 18

Ile Ile Thr Ile Ile
1               5

<210> SEQ ID NO 19
<211> LENGTH: 25
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 19

Phe Tyr Phe Leu Gln Ile Phe Phe Pro Ala Ser Leu Ile Val Thr Ile
1               5                   10                  15

Ser Trp Leu Asn Arg Glu Ala Ser Arg
            20                  25

<210> SEQ ID NO 20
<211> LENGTH: 25
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 20

Phe Tyr Phe Leu Asn Ile Phe Phe Pro Ala Ser Leu Ile Val Thr Ile
1               5                   10                  15

Ser Trp Leu Asn Arg Glu Ala Ser Arg
            20                  25

<210> SEQ ID NO 21
<211> LENGTH: 25
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 21

Phe Tyr Phe Leu Gln Ile Val Phe Pro Ala Ser Leu Ile Val Thr Ile
1               5                   10                  15

Ser Trp Leu Asn Arg Glu Ala Ser Arg
            20                  25
```

```
<210> SEQ ID NO 22
<211> LENGTH: 198
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 22
```

Cys Pro Met Asp Leu Lys Leu Phe Pro Met Asp Ser Gln His Cys Lys
1               5                   10                  15

Leu Glu Ile Glu Ser Tyr Gly Tyr Glu Thr Lys Asp Ile Asp Tyr Tyr
            20                  25                  30

Trp Gly Lys Lys Arg Thr Asp Leu Glu Ile Thr Ala Val Lys Phe Asp
        35                  40                  45

Thr Phe Gln Leu Pro Gln Phe Gln Pro Thr Leu Tyr Phe Val Asn Thr
50                  55                  60

Thr Lys Ala Glu Thr Ser Ser Gly Lys Tyr Val Arg Leu Ala Leu Glu
65                  70                  75                  80

Val Ile Leu Val Arg Asn Met Gly Phe Tyr Thr Met Asn Ile Val Ile
                85                  90                  95

Pro Ser Ile Leu Ile Val Thr Ile Ser Trp Val Ser Phe Trp Leu Asn
            100                 105                 110

Arg Glu Ala Ser Pro Ala Arg Val Gly Leu Gly Val Thr Thr Val Leu
        115                 120                 125

Thr Met Thr Thr Leu Ile Thr Thr Thr Asn Asn Ser Met Pro Lys Val
130                 135                 140

Ser Tyr Val Lys Gly Leu Asp Val Phe Leu Asn Phe Cys Phe Val Met
145                 150                 155                 160

Val Phe Ala Ser Leu Leu Glu Tyr Ala Ile Val Ser Asp Lys Leu Ser
                165                 170                 175

Arg Tyr Gly Phe Pro Leu Ser Phe Ser Ile Phe Asn Ile Val Tyr Trp
            180                 185                 190

Leu Tyr Met Lys Tyr Leu
        195

```
<210> SEQ ID NO 23
<211> LENGTH: 194
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 23
```

Cys Pro Met His Leu Glu Asp Phe Pro Met Asp Ala His Ala Cys Pro
1               5                   10                  15

Leu Lys Phe Gly Ser Tyr Ala Tyr Thr Arg Ala Glu Val Val Tyr Glu
            20                  25                  30

Trp Thr Arg Glu Pro Ala Arg Ser Val Val Val Ala Glu Asp Gly Ser
        35                  40                  45

Arg Leu Asn Gln Tyr Asp Leu Leu Gly Gln Thr Val Asp Ser Gly Ile
50                  55                  60

Val Gln Ser Ser Thr Gly Glu Tyr Val Val Met Thr Thr His Phe His
65                  70                  75                  80

Leu Lys Arg Lys Ile Gly Tyr Phe Val Ile Gln Thr Tyr Leu Pro Cys
                85                  90                  95

Ile Met Thr Val Ile Leu Ser Gln Val Ser Phe Trp Leu Asn Arg Glu
            100                 105                 110

```
Ser Val Pro Ala Arg Thr Val Phe Gly Val Thr Thr Val Leu Thr Met
        115                 120                 125

Thr Thr Leu Ser Ile Ser Ala Arg Asn Ser Leu Pro Lys Val Ala Tyr
        130                 135                 140

Ala Thr Ala Met Asp Trp Phe Ile Ala Val Cys Tyr Ala Phe Val Phe
145                 150                 155                 160

Ser Ala Leu Ile Glu Phe Ala Thr Val Asn Asp Arg Leu Ser Arg Ile
                165                 170                 175

Ala Phe Pro Leu Leu Phe Gly Ile Phe Asn Leu Val Tyr Trp Ala Thr
            180                 185                 190

Tyr Leu

<210> SEQ ID NO 24
<211> LENGTH: 191
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 24

Cys Met Met Asp Leu Arg Arg Tyr Pro Leu Asp Glu Gln Asn Cys Thr
1               5                   10                  15

Leu Glu Ile Glu Ser Tyr Gly Tyr Thr Thr Asp Asp Ile Glu Phe Tyr
            20                  25                  30

Trp Asn Gly Gly Glu Gly Ala Val Thr Gly Val Asn Lys Ile Glu Leu
        35                  40                  45

Pro Gln Phe Ser Ile Val Asp Tyr Lys Met Val Ser Lys Lys Val Glu
    50                  55                  60

Phe Thr Thr Gly Ala Tyr Pro Arg Leu Ser Leu Ser Phe Arg Leu Lys
65                  70                  75                  80

Arg Asn Ile Gly Tyr Phe Ile Leu Gln Thr Tyr Met Pro Ser Thr Leu
                85                  90                  95

Ile Thr Ile Leu Ser Trp Val Ser Phe Trp Ile Asn Tyr Asp Ala Ser
            100                 105                 110

Ala Ala Arg Val Ala Leu Gly Ile Thr Thr Val Leu Thr Met Thr Thr
        115                 120                 125

Ile Ser Thr His Leu Arg Glu Thr Leu Pro Lys Ile Pro Tyr Val Lys
    130                 135                 140

Ala Ile Asp Ile Tyr Leu Met Gly Cys Phe Val Phe Val Phe Leu Ala
145                 150                 155                 160

Leu Leu Glu Tyr Ala Phe Val Asn Asp Lys Trp Ser Arg Met Phe Phe
                165                 170                 175

Pro Ile Thr Phe Ser Leu Phe Asn Val Val Tyr Trp Leu Tyr Tyr
            180                 185                 190

<210> SEQ ID NO 25
<211> LENGTH: 191
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 25

Cys Gln Leu Gln Leu His Asn Phe Pro Met Asp Glu His Ser Cys Pro
1               5                   10                  15

Leu Glu Phe Ser Ser Tyr Gly Tyr Pro Arg Glu Glu Ile Val Tyr Gln
            20                  25                  30
```

Trp Lys Arg Ser Ser Val Glu Val Gly Asp Thr Arg Ser Trp Arg Leu
                35                  40                  45

Tyr Gln Phe Ser Phe Val Gly Leu Arg Asn Thr Thr Glu Val Val Lys
        50                  55                  60

Thr Thr Ser Gly Asp Tyr Val Val Met Ser Val Tyr Phe Asp Leu Ser
65                  70                  75                  80

Arg Arg Met Gly Tyr Phe Thr Ile Gln Thr Tyr Ile Pro Cys Thr Leu
                85                  90                  95

Ile Val Val Leu Ser Trp Val Ser Phe Trp Ile Asn Lys Asp Ala Val
            100                 105                 110

Pro Ala Arg Thr Ser Leu Gly Ile Thr Thr Val Leu Thr Met Thr Thr
        115                 120                 125

Leu Ser Thr Ile Ala Arg Lys Ser Leu Pro Lys Val Ser Tyr Val Thr
130                 135                 140

Ala Met Asp Leu Phe Val Ser Val Cys Phe Ile Phe Val Phe Ser Ala
                145                 150                 155                 160

Leu Val Glu Tyr Gly Thr Leu His Ser Tyr Ala Arg Ile Phe Phe Pro
                165                 170                 175

Thr Ala Phe Cys Leu Phe Asn Leu Val Tyr Trp Val Ser Tyr Leu
            180                 185                 190

<210> SEQ ID NO 26
<211> LENGTH: 85
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 26

Phe Tyr Thr Met Asn Ile Val Ile Pro Ser Ile Met Ile Val Thr Ile
1               5                   10                  15

Ser Trp Val Ser Phe Trp Leu Asn Arg Glu Ala Ser Pro Ala Arg Val
            20                  25                  30

Gly Leu Gly Val Thr Thr Val Leu Thr Met Thr Thr Leu Ile Thr Thr
        35                  40                  45

Thr Asn Asn Ser Met Pro Lys Val Ser Tyr Val Lys Gly Leu Asp Val
    50                  55                  60

Phe Leu Asn Phe Cys Phe Val Met Val Phe Ala Ser Leu Leu Glu Tyr
65                  70                  75                  80

Ala Ile Val Ser Tyr
                85

<210> SEQ ID NO 27
<211> LENGTH: 85
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 27

Phe Tyr Phe Leu Gln Ile Phe Phe Pro Ala Ser Leu Val Val Val Leu
1               5                   10                  15

Ser Trp Ile Ser Phe Trp Ile Asn Arg Asp Ser Ala Pro Ser Arg Thr
            20                  25                  30

Leu Ile Gly Thr Met Thr Val Leu Thr Glu Thr His Leu Met Thr Gly
        35                  40                  45

```
Thr Asn Arg Arg Leu Pro Pro Val Ala Tyr Val Lys Ala Val Asp Val
 50                  55                  60

Phe Leu Gly Phe Cys Tyr Leu Val Ile Leu Ala Leu Ile Glu Tyr
 65                  70                  75                  80

Ala Cys Val Ala Tyr
                 85

<210> SEQ ID NO 28
<211> LENGTH: 85
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 28

Tyr Phe Val Ile Gln Thr Tyr Leu Pro Cys Ile Met Thr Val Ile Leu
 1               5                  10                  15

Ser Gln Val Ser Phe Trp Leu Asn Arg Glu Ser Val Pro Ala Arg Thr
                20                  25                  30

Val Phe Gly Val Thr Thr Val Leu Thr Met Thr Thr Leu Ser Ile Ser
             35                  40                  45

Ala Arg Asn Ser Leu Pro Lys Val Ala Tyr Ala Thr Ala Met Asp Trp
 50                  55                  60

Phe Ile Ala Val Cys Tyr Ala Phe Val Phe Ser Ala Leu Ile Glu Phe
 65                  70                  75                  80

Ala Thr Val Asn Tyr
                 85

<210> SEQ ID NO 29
<211> LENGTH: 85
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 29

Tyr Phe Ile Leu Gln Thr Tyr Met Pro Ser Thr Leu Ile Thr Ile Leu
 1               5                  10                  15

Ser Trp Val Ser Phe Trp Ile Asn Tyr Asp Ala Ser Ala Ala Arg Val
                20                  25                  30

Ala Leu Gly Ile Thr Thr Val Leu Thr Met Thr Thr Ile Ser Thr His
             35                  40                  45

Leu Arg Glu Thr Leu Pro Lys Ile Pro Tyr Val Lys Ala Ile Asp Ile
 50                  55                  60

Tyr Leu Met Gly Cys Phe Val Phe Val Phe Leu Ala Leu Leu Glu Tyr
 65                  70                  75                  80

Ala Phe Val Asn Tyr
                 85

<210> SEQ ID NO 30
<211> LENGTH: 85
<212> TYPE: PRT
<213> ORGANISM: Artificial Sequence
<220> FEATURE:
<223> OTHER INFORMATION: Description of Artificial Sequence: Note =
      Synthetic Construct
```

-continued

```
<400> SEQUENCE: 30

Tyr Phe Thr Ile Gln Thr Tyr Ile Pro Cys Ile Leu Thr Val Val Leu
1               5                   10                  15

Ser Trp Val Ser Phe Trp Ile Asn Lys Asp Ala Val Pro Ala Arg Thr
            20                  25                  30

Ser Leu Gly Ile Thr Thr Val Leu Thr Met Thr Thr Leu Ser Thr Ile
        35                  40                  45

Ala Arg Lys Ser Leu Pro Lys Val Ser Tyr Val Thr Ala Met Asp Leu
    50                  55                  60

Phe Val Ser Val Cys Phe Ile Phe Val Phe Ala Ala Leu Met Glu Tyr
65                  70                  75                  80

Gly Thr Leu His Tyr
                85

<210> SEQ ID NO 31
<211> LENGTH: 53
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 31

Phe Tyr Thr Met Asn Ile Val Ile Pro Ser Ile Leu Ile Val Thr Ile
1               5                   10                  15

Ser Trp Val Ser Phe Trp Leu Asn Arg Glu Ala Ser Pro Ala Leu Ile
            20                  25                  30

Thr Thr Thr Asn Asn Ser Met Pro Lys Val Ser Tyr Val Lys Gly Leu
        35                  40                  45

Asp Val Phe Leu Asn
    50

<210> SEQ ID NO 32
<211> LENGTH: 53
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 32

Phe Tyr Phe Leu Gln Ile Phe Phe Pro Ala Ser Leu Val Val Val Leu
1               5                   10                  15

Ser Trp Ile Ser Phe Trp Ile Asn Arg Asp Ser Ala Pro Ser Leu Met
            20                  25                  30

Thr Gly Thr Asn Arg Arg Leu Pro Pro Val Ala Tyr Val Lys Ala Val
        35                  40                  45

Asp Val Phe Leu Gly
    50

<210> SEQ ID NO 33
<211> LENGTH: 339
<212> TYPE: PRT
<213> ORGANISM: Artificial Sequence
<220> FEATURE:
<223> OTHER INFORMATION: Description of Artificial Sequence: Note =
      Synthetic Construct
```

```
<400> SEQUENCE: 33

Met Trp Gly Leu Ala Gly Gly Arg Leu Phe Gly Ile Phe Ser Ala Pro
1               5                   10                  15

Val Leu Val Ala Val Val Cys Cys Ala Gln Ser Val Asn Asp Pro Gly
            20                  25                  30

Asn Met Ser Phe Val Lys Glu Thr Val Asp Lys Leu Leu Lys Gly Tyr
        35                  40                  45

Asp Ile Arg Leu Arg Pro Asp Phe Gly Gly Pro Pro Val Cys Val Gly
    50                  55                  60

Met Asn Ile Asp Ile Ala Ser Ile Asp Met Val Ser Glu Val Asn Met
65                  70                  75                  80

Asp Tyr Thr Leu Thr Met Tyr Phe Gln Gln Tyr Trp Arg Asp Lys Arg
                85                  90                  95

Leu Ala Tyr Ser Gly Ile Pro Leu Asn Leu Thr Leu Asp Asn Arg Val
            100                 105                 110

Ala Asp Gln Leu Trp Val Pro Leu Arg Ile Thr Thr Thr Ala Ala Cys
        115                 120                 125

Met Met Asp Leu Arg Arg Tyr Pro Leu Asp Glu Gln Asn Cys Thr Leu
130                 135                 140

Glu Ile Glu Ser Tyr Gly Tyr Thr Thr Asp Asp Ile Glu Phe Tyr Trp
145                 150                 155                 160

Arg Gly Gly Asp Lys Ala Val Thr Gly Asx Glu Arg Ile Glu Leu Pro
                165                 170                 175

Gln Phe Ser Ile Val Glu His Arg Leu Val Ser Arg Asn Val Val Phe
            180                 185                 190

Ala Thr Gly Ala Tyr Pro Arg Leu Ser Leu Ser Phe Arg Leu Lys Arg
        195                 200                 205

Asn Ile Gly Tyr Phe Ile Leu Gln Thr Tyr Met Pro Ser Ile Leu Ile
    210                 215                 220

Thr Ile Leu Ser Trp Val Ser Phe Trp Ile Asn Tyr Asp Ala Ser Ala
225                 230                 235                 240

Ala Arg Val Ala Leu Gly Ile Thr Thr Val Leu Thr Met Thr Thr Ile
                245                 250                 255

Asn Thr His Leu Arg Glu Thr Leu Pro Lys Ile Pro Tyr Val Lys Ala
            260                 265                 270

Ile Asp Met Tyr Leu Met Gly Cys Phe Val Phe Val Phe Leu Ala Leu
        275                 280                 285

Leu Glu Tyr Ala Phe Val Asn Tyr Ile Phe Phe Gly Arg Gly Pro Gln
    290                 295                 300

Arg Gln Lys Lys Leu Ala Glu Lys Thr Asn Ala Ile Asp Arg Trp Ser
305                 310                 315                 320

Arg Ile Val Phe Pro Phe Thr Phe Ser Leu Phe Asn Leu Val Tyr Trp
                325                 330                 335

Leu Tyr Tyr

<210> SEQ ID NO 34
<211> LENGTH: 380
<212> TYPE: PRT
<213> ORGANISM: Artificial Sequence
<220> FEATURE:
<223> OTHER INFORMATION: Description of Artificial Sequence: Note =
      Synthetic Construct
```

<400> SEQUENCE: 34

```
Met Ala Arg Pro Phe Thr Leu Ile Val Leu Leu Ser Ala His Leu Cys
1               5                   10                  15
Leu His Val Val Val Thr Gln Asp Glu Asp Ser His Ile Asn Thr Gln
            20                  25                  30
Leu Leu Ser Ser Val Leu Asp Arg Leu Thr Asn Arg Thr Thr Tyr Asp
        35                  40                  45
Lys Arg Leu Arg Pro Arg Tyr Gly Glu Lys Pro Asx Asp Val Gly Ile
50                  55                  60
Thr Ile His Val Ser Ser Ile Ser Ala Val Ser Glu Val Asp Asn Asp
65                  70                  75                  80
Phe Thr Leu Asp Phe Tyr Met Arg Gln Thr Trp Gln Asp Pro Arg Leu
                85                  90                  95
Ala Phe Gly Ser Leu Asp Leu Gly Leu Ser Lys Glu Ile Asp Ser Leu
            100                 105                 110
Thr Val Gly Val Asp Tyr Leu Asp Arg Leu Trp Lys Pro Asp Thr Phe
        115                 120                 125
Phe Pro Asn Glu Lys Lys Ser Phe Phe His Leu Ala Thr Thr His Asn
130                 135                 140
Ser Phe Leu Arg Ile Glu Gly Asp Gly Thr Val Tyr Thr Ser Gln Arg
145                 150                 155                 160
Leu Thr Val Thr Ala Thr Cys Pro Met Asp Leu Lys Leu Phe Pro Met
                165                 170                 175
Asp Ser Gln His Cys Lys Leu Glu Ile Glu Ser Tyr Gly Tyr Glu Thr
            180                 185                 190
Lys Asp Ile Asp Tyr Tyr Trp Gly Lys Lys Arg Thr Asp Leu Glu Ile
        195                 200                 205
Thr Ala Val Lys Phe Asp Thr Phe Gln Leu Pro Gln Phe Gln Pro Thr
210                 215                 220
Leu Tyr Phe Val Asn Thr Thr Lys Ala Glu Thr Ser Ser Gly Lys Tyr
225                 230                 235                 240
Val Arg Leu Ala Leu Glu Val Ile Leu Val Arg Asn Met Gly Phe Tyr
                245                 250                 255
Thr Met Asn Ile Val Ile Pro Ser Ile Leu Ile Val Thr Ile Ser Trp
            260                 265                 270
Val Ser Phe Trp Leu Asn Arg Glu Ala Ser Pro Ala Arg Val Gly Leu
        275                 280                 285
Gly Val Thr Thr Val Leu Thr Met Thr Thr Leu Ile Thr Thr Thr Asn
290                 295                 300
Asn Ser Met Pro Lys Val Ser Tyr Val Lys Gly Leu Asp Val Phe Leu
305                 310                 315                 320
Asn Phe Cys Phe Val Asn Val Phe Ala Ser Leu Leu Glu Tyr Ala Ile
                325                 330                 335
Val Ser Tyr Met Asn Lys Arg Leu Val Leu Arg Arg Lys Ile Asp Lys
            340                 345                 350
Leu Ser Arg Tyr Gly Phe Pro Leu Ser Phe Ser Ile Phe Asn Ile Val
        355                 360                 365
Tyr Trp Leu Tyr Met Lys Tyr Leu Ser Leu Asn Ser
370                 375                 380
```

<210> SEQ ID NO 35
<211> LENGTH: 6
<212> TYPE: PRT
<213> ORGANISM: Artificial Sequence

```
<220> FEATURE:
<223> OTHER INFORMATION: Description of Artificial Sequence: Note =
      Synthetic Construct

<400> SEQUENCE: 35

Thr Met Gln Phe Ile Ser
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 36

Phe Leu Gln Phe Phe Ala
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 37

Phe Met Gln Phe Ile Ser
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 38

Thr Leu Gln Phe Ile Ser
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 39

Thr Met Gln Phe Phe Ser
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 40

Thr Met Gln Phe Ile Ala
1               5
```

```
<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 41

Phe Leu Gln Phe Ile Ser
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 42

Phe Met Gln Phe Phe Ser
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 43

Phe Met Gln Phe Ile Ala
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 44

Thr Leu Gln Phe Phe Ser
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 45

Thr Leu Gln Phe Ile Ala
1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct
```

```
<400> SEQUENCE: 46

Thr Met Gln Phe Phe Ala
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 47

Thr Leu Gln Phe Phe Ala
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 48

Phe Met Gln Phe Phe Ala
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 49

Phe Leu Gln Phe Ile Ala
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 50

Phe Leu Gln Phe Phe Ser
1               5
```

METHODS AND COMPOSITIONS RELATED TO GABA RECEPTOR SUBUNITS

I. CROSS REFERENCE TO RELATED APPLICATIONS

The present application is a National Phase Application of International Application No. PCT/US2007/012089 filed May 21, 2007, which claims priority to U.S. Pat. application No. 60/801,994, filed May 8, 2006, which applications are incorporated herein fully 19by this reference.

II. ACKNOWLEDGEMENTS

This invention was made with government support under grant NS 43345-01 from the National Institutes of Health. The government has certain rights in this invention.

III. BACKGROUND

The gamma-aminobutyric acid receptors (GABA receptors) are the most abundant inhibitory receptor in the mammalian brain. They are comprised of a heteropolymeric structure that form a chloride ion channel, and contain multiple recognition sites for the binding of molecules. The binding of GABA to its specific recognition site on the GABA receptor opens the ion channel and allows chloride ions to flow into the nerve cell. This action hyperpolarizes the cell membrane of that neuron and thereby makes the cell less reactive to excitatory stimuli. The chloride ion current may also be regulated by various drugs that serve as positive or negative modulators of the GABA receptor (Puia, G. et al. Molecular Pharm. 1991, 39, 691).

Many clinical conditions are thought to arise, in part, from the imbalance between neurotransmission of GABA and those of other neurotransmitters. These conditions include Huntington's chorea, Parkinson's disease, spasticity, epilepsy, schizophrenia and tardive dyskinesia. Decreased GABA activity appears to contribute to the pathogenesis of these diseases. In addition, analgesia and satiety are thought to be regulated by GABA activity. Methods of modifying GABAergic neurotransmission are therefore desirable in order to modify these conditions.

The so-called benzodiazepine (BZD) receptor is a site for such allosteric modulators on one class of the GABA receptor, the GABA-A receptor. This site mediates two opposing effects, one that amplifies the action of GABA ("positive" efficacy) and the other that reduces the action of GABA ("negative" efficacy). Agents facilitating GABA-receptor/chloride ion-channel functions via the BZD site are referred to as agonists, while agents reducing such function are referred to as inverse agonists. Antagonists at this site block the effects of agonists or inverse agonists by competitively inhibiting their binding. It is thus possible to have a series of compounds in which members equally bind to the BZD site but have equal and opposite regulatory effects on the $GABA_A$ receptor/chloride ion channel. Also, within the series a continuum of activity is possible (Takada, S. et al. J. Med. Chem. 1988, 31, 1738). Thus, BZD receptor ligands can induce a wide spectrum of pharmacological effects ranging from muscle relaxant, hypnotic, sedative, anxiolytic, and anticonvulsant activities, produced by full or partial agonists ("positive"), to the proconvulsant, anti-inebriant, and anxiogenic activities, produced by inverse agonists ("negative"). (A further understanding of this area can be gleaned from: Mohler, H. Arzneim.-Forsch./Drug Res. 1992, 42 (2a), 211; Haefely, W. et al., Advances in Drug Research, Academic Press, vol. 14, 1985, pp. 165-322; Skolnick, P. et al., GABA and Benzodiazepine Receptors, Squires, R., Ed., 1987, pp. 99-102 and references cited therein, all herein incorporated by reference in their entirety.)

The fourth edition of the Diagnostic and Statistical Manual of Mental Disorders (DSM-IV™), published in 1994 by the American Psychiatric Association, Washington, D.C., defines anxiety and related disorders (herein incorporated by reference in its entirety). These are panic disorder without agoraphobia, panic disorder with agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

Anxiety disorders are generally treated by counseling or with drugs. Classes of drugs which are widely prescribed for the treatment of anxiety disorders include the benzodiazepines (such as diazepam) and buspirone hydrochloride.

Several animal models have been developed which are recognized in the art as being predictive of anxiolytic activity. These include the fear-potentiated startle model, described by Davis in Psychopharmacology 62:1; 1979, Behav. Neurosci. 100:814;1986 and TiPS, January 1992 Vol. 13, 35-41, the elevated plus model described by Lister in Psychopharmacol. 92:180-185; 1987, and the well-known punished-responding (conflict) model, described, for example, in "Psychopharmacology of Anxiolytics and Antidepressants", edited by S. E. File, pp. 131-153, Raven Press, New York, 1991, all herein incorporated by reference in their entirety.

Drugs targeting $GABA_A$ receptors produce undesirable results because they indiscriminately target most of the $GABA_A$ receptors in the brain. What is needed in the art are drugs that target subsets of those receptors for greater specificity.

IV. SUMMARY

Disclosed herein is a $GABA_A$ receptor with a mutation in the transmembrane region, wherein the mutation confers altered drug specificity to the receptor.

Also disclosed herein is a method of modulating $GABA_A$ receptor function, comprising contacting the transmembrane domain with a ligand thereof. Disclosed is a method of modulating $GABA_A$ receptor function, comprising contacting the M1 domain with a ligand thereof The mutation in the M1 domain of M1 can comprise a mutation in residue 258, 259, 261, 257, 262 or 265. Disclosed is a method of modulating $GABA_A$ receptor function, comprising contacting the M2-M3 linker domain with a ligand thereof. Disclosed is a method of modulating $GABA_A$ receptor function, comprising contacting the M1 and M2-M3 linker domain with a ligand thereof.

Further disclosed is a method of modulating $GABA_A$ receptor function in a subject in need thereof, comprising: a) identifying a subject in need of neurosteroid treatment; b) administering to the subject an effective amount of a ligand that modulates $GABA_A$ receptor function, thereby modulating $GABA_A$ receptor function in a subject in need thereof.

Disclosed is a method of increasing neurosteroid sensitivity in $GABA_A$ receptors, comprising mutating the residue at position 258, 259, 261, 257, 262 or 265 of M1. Also disclosed is an assay comprising a $GABA_A$ receptor, wherein the $GABA_A$ receptor comprises a mutation at position 258, 259, 261, 257, 262 or 265 of M1.

Disclosed is a polypeptide comprising SEQ ID NO: 3, wherein the asparagine residue has been mutated to arginine at position 305.

Also disclosed is a method for treating neurological disorders comprising administering to a subject in need thereof a composition that targets the transmembrane domain of the $GABA_A$ receptor.

Disclosed herein is a method of screening a test compound that modulates a $GABA_A$ receptor at a location of interest on the receptor comprising the following steps: a) measuring the response of the test compound to a cell expressing the wild-type $GABA_A$ receptor; b) measuring the response of the test compound to a cell expressing a mutated $GABA_A$ receptor, wherein the mutation is in the location of interest; c) comparing the response of the test compound in steps a) and b); d) determining if the test compound modulates the $GABA_A$ receptor at the location of interest based on the results of step c).

Further disclosed is a method of screening for a compound that modulates GABA comprising: a) measuring the response of cells expressing wild-type $GABA_A$ receptor to GABA; b) measuring the response of cells expressing a mutant $GABA_A$ receptor to GABA, wherein the mutation is in the location of interest; c) comparing the measurements of step a) and b); d) measuring the response of cells expressing the wild-type $GABA_A$ receptor to GABA plus the test compound; e) measuring the response of cells expressing the mutant $GABA_A$ receptor, wherein the mutation is in the location of interest, to GABA plus the test compound; f) comparing the measurements of d) and e); g) comparing the results of steps c and f); wherein a difference in response of a cell in the presence of a test compound versus not in the presence of a test compound indicates a compound that modulates GABA.

V. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows the UNC-49B/C heteromer is more sensitive to PS inhibition than the UNC-49B homomer. PS (10 µM) inhibition of GABA-evoked currents from *Xenopus* oocytes expressing UNC-49B homomeric GABA receptors (a) or UNC-49B/C heteromeric receptors (b). PS was pre-applied for 20 seconds prior to co-application of PS and GABA (at $EC_{50}$). c) PS dose-response curves for UNC-49B homomers and UNC-49B/C heteromers. Peak currents evoked by $EC_{50}$ GABA plus PS, normalized to currents evoked by GABA alone, are plotted against PS concentration. Error bars represent SEM (n=4 oocytes for each receptor).

FIG. 2 shows M1, and the M2-M3 extracellular linker contains determinants of PS sensitivity. a) UNC-49B and UNC-49C contain 188 identical N-terminal amino acids (gray), but different C-terminal regions (white for UNC-49B, black for UNC-49C). 'c-c' indicates the conserved cysteine loop, M1-M4 indicates transmembrane domains, and numbers above UNC-49B indicate chimera junctions shown in (b). Note that the M1 chimera contains the M1-M2 linker from UNC-49C. b) Chimeric subunits comprising UNC-49B (white) and UNC-49C (black) sequences are differentially-sensitive to PS inhibition. The UNC-49C M1 and M2-M3 linker domains are necessary for high PS sensitivity (n≧3 oocytes for each molecule). Asterisks are placed between each pair of adjacent columns that differ significantly (* P<0.01, ** P<0.001, One-way ANOVA with Tukey's multiple comparison test; n≧3 for each chimera). c) PS dose response curve for the linker, M1, and double chimeras. PS inhibition was measured at the GABA $EC_{50}$ for each subunit (n=4 oocytes). Representative traces showing the inhibition of the double chimera (M1+linker) by 10 µM PS are shown below the PS dose-response curves.

FIG. 3 shows conserved amino acids in M1 and the M2-M3 linker mediate PS sensitivity. a) Alignment of UNC-49B (SEQ ID NO: 5), UNC-49C (SEQ ID NO: 6) and the $GABA_A$ receptor α1 (SEQ ID NO: 7), (β1(SEQ ID NO: 8) and γ1 (SEQ ID NO: 9) subunits. Bars indicate the positions of transmembrane domains. Boxed residues are conserved in UNC-49C and the vertebrate receptors, but differ in UNC-49B. Alignment is shown with a subset of receptors which were compared to illustrate conserved and divergent residues (see Materials and Methods). b) PS dose-response curves comparing the M1 chimera (open triangles) and M1-R subunit (closed triangles; n=4 oocytes for each receptor). c) PS dose-response curves for the N305R subunit (open diamonds), and the QF-R subunit (closed diamonds; n=4 oocytes for each receptor). Dashed line is the M 1-R PS dose-response curve, re-plotted from panel b. Representative traces showing the inhibition of the M1-R and QF-R receptors by 10µM PS are shown next to the PS dose-response curves in (b) and (c), respectively. PS responses were measured at the $EC_{50}$ GABA concentration for each subunit.

FIG. 4 shows localization of residues important for PS inhibition within M1. a) Subdivision of the M1 domain, including the M1-2 linker, into three segments, designated X, Y, and Z. Asterisks indicate conserved residues at positions 259 and 261, arrows represent boundaries of the X segment (residues 255-264), Y segment (residues 265-273), and Z segment (residues 274-282) for UNC-49B (SEQ ID NO: 10) and for UNC-49C (SEQ ID NO: 11). b) PS sensitivity of chimeric receptors in which UNC-49C sequences corresponding to the X, Y, and Z segments have been swapped into the QF-R subunit in different combinations. Bars at the left represent the M1 plus M1-2 linker region in (a). Closed portions are UNC-49C, open are UNC-49B. Black dots represent UNC-49B to UNC-49C mutations at positions 259, 261, and 305. PS $IC_{50}$ values were determined by generating PS dose-response curves at $EC_{50}$ GABA (n ≧3 ooctye for each molecule; Table 2).

FIG. 5 shows identification of M1 residues important for PS inhibition. a) PS sensitivity of Y segment mutants in the X chimera background. Chimeric M1 domain depicted as in FIG. 4. Grid indicates the residue present at each position that is divergent between UNC-49B and UNC-49C. Closed boxes and white letters are UNC-49C, open boxes and black letters are UNC-49B. The X chimera corresponds to SEQ ID NO: 12 and the XY chimera corresponds to SEQ ID NO: 13. From top to bottom, the single B→C substitutions correspond to SEQ ID NO: 14, SEQ ID NO: 15, SEQ ID NO: 16, SEQ ID NO: 17, and SEQ ID NO: 18, respectively. b) PS sensitivity of X segment mutants in the Y chimera background. The X chimera corresponds to SEQ ID NO: 35 and the XY chimera corresponds to SEQ ID NO: 36. From top to bottom, the single BC substitutions correspond to SEQ ID NO: 37, SEQ ID NO: 38, SEQ ID NO: 39, and SEQ ID NO: 40, respectively. From top to bottom, the double B→C substitutions correspond to SEQ ID NO: 41, SEQ ID NO: 42, SEQ ID NO: 43, SEQ ID NO: 44, SEQ ID NO: 45, and SEQ ID NO: 46, respectively. From top to bottom, the triple B→C substitutions correspond to SEQ ID NO: 47, SEQ ID NO: 48, SEQ ID NO: 49, and SEQ ID NO: 50, respectively. Grid indicates residues at divergent positions between UNC-49B and UNC-49C as in (a). 'n/f' indicates non functional. Open bars on bar graph represent biphasic PS dose responses. Black dots on subunit diagrams in (a) and (b) represent UNC-49B to UNC-49C mutations at positions 259, 261, and 305. Biphasic PS dose-response of mutants containing the M258L mutation, compared to the Y chimera. All PS $IC_{50}$ values and dose-response curves generated at $EC_{50}$ GABA (n >3 ooctye for each molecule; Table 3).

FIG. 6 shows the importance of conserved residues 259 and 261 in M 1. The molecule X(12655) (SEQ ID NO: 19) contains a stretch of UNC-49C residues in M1 and an UNC-49B to C substitution in the M2-3 linker (black letters on white background are UNC-49B residues, white letters on a black background are UNC-49C residues, black letters on a grey background are the same in both subunits). Conserved residues Q259 and F261 were reverted to their UNC-49B amino acids (asparagine and valine, respectively). The Q259N reversion (SEQ ID NO: 20) reduced PS sensitivity, but the F261V reversion did not. Therefore, the F261V reversion of X(I265S) contains the minimum number of UNC-49C residues (seven) required to produce high PS sensitivity, and is designated UNC-49B-PS7 (SEQ ID NO: 21). PS $IC_{50}$ values were measured at $EC_{50}$ GABA for each subunit (n=4 oocytes for each molecule, Table 3). Representative traces showing the inhibition of UNC-49B-PS7 by 10µM PS are shown in the lower panel.

FIG. 7 shows the effects of mutations on picrotoxin sensitivity. Picrotoxin dose-response curves for mutants with varying PS sensitivity. Picrotoxin inhibition is measured at $EC_{50}$ GABA (n=4 oocytes for each mutant). Picrotoxin dose-response curves for UNC-49B and UNC-49B/C from Bamber et al. (2003).

FIG. 8 shows homology model of UNC-49B, showing residues important for PS inhibition. Model of the UNC-49B homopentamer, with PS-sensitive substitutions in M1, threaded onto the 4A structure of the nicotinic acetylcholine receptor (Miyazawa et al., 2003). a) View into the receptor from the outside of the cell. Transmembrane helices are shown as ribbons, residues identified as important for PS inhibition are shown as ball-and-stick representations. Helices in green belong to a single subunit; two of the four helices of the adjacent subunit shown in blue, M2 helices only of the three remaining subunits shown in red. b) View in the plane of the membrane showing surface representation of UNC-49B. Residues important for PS inhibition are indicated and colored (ILE, cyan; THR, orange; MET, yellow; ASN, purple). Color scheme corresponds to subunit colors in (a).

Figure 11A:
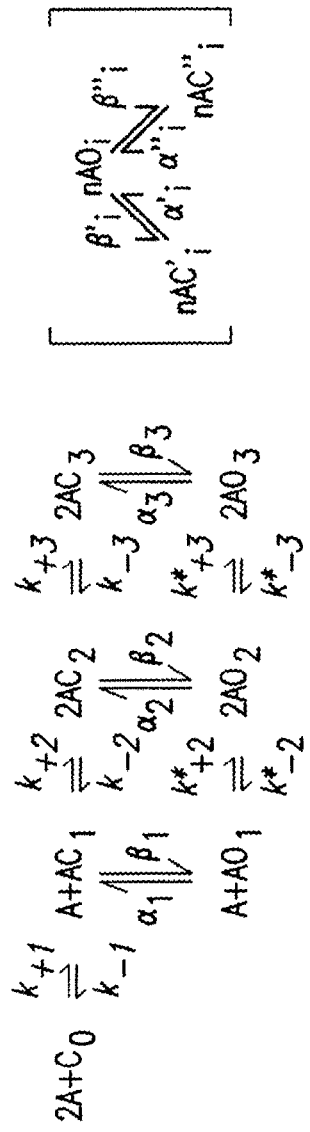
Figure 11B:
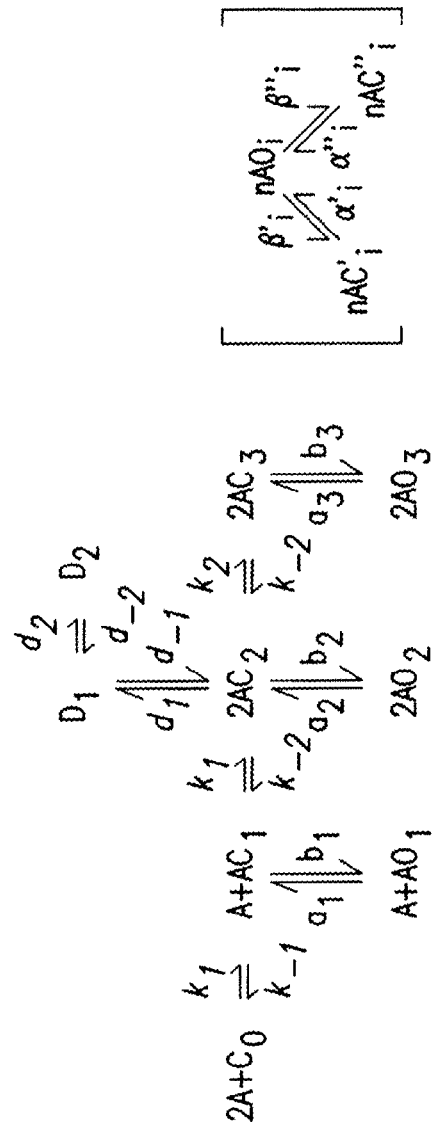

FIG. 11 shows kinetic models of neurosteroid function. A) Twyman and Macdonald (1990), native $GABA_A$ receptors from spinal cord. B) Gingrich et al., (1995), $\alpha_1$ or $\alpha_3$, $\beta_3$, $\gamma_{2S}$ receptors in HEK-293 cells (scheme for distal closed states for each open state, bracketed to right of model) C) Jones and Westbrook (1995), native $GABA_A$ receptors from hippocampus. D) Haas and Macdonald (1999), $\alpha_1\beta_3\delta$ (left), and $\alpha_1\beta_3\gamma_{2L}$ (right) $GABA_A$ receptors in L929 fibroblast cells.

Figure 12:
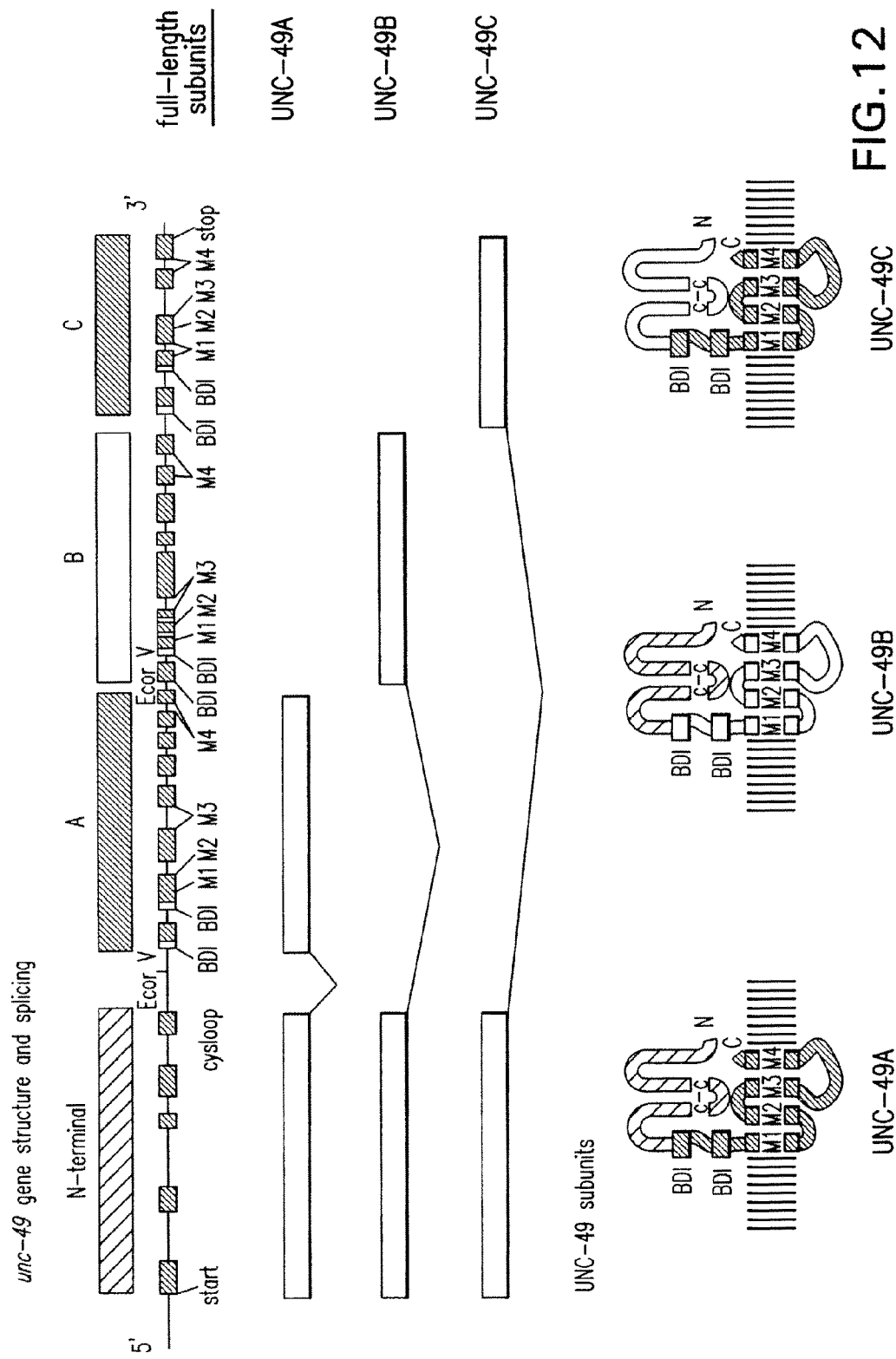

FIG. 12 shows structure and splicing of the *C. elegans* unc-49 gene. Top: structure of unc-49. 'N-terminal' region encodes the common amino terminus for each subunit, which is spliced to region 'A', 'B', or 'C' to produce three structurally-distinct GABAA receptor subunits (bottom).

Figures 13A, 13B:
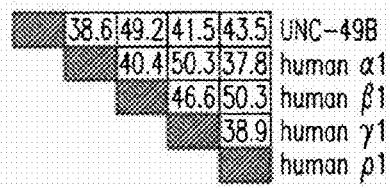

FIG. 13 shows conservation of UNC-49B (SEQ ID NO: 22) and mammalian $GABA_A$ receptor subunits α1 (SEQ ID NO: 23), β1 (SEQ ID NO: 24), and γ1 (SEQ ID NO: 25). A) Alignment of functionally important regions. Residues identical in 3 out of 4 subunits are boxed. Conserved disulfide loop (c-c loop), GABA binding domains (BDI, II), and transmembrane domains (M1-4) are indicated. The non-conserved M3-4 loop has been deleted (dashed vertical line). B) Matrix of % similarities.

FIG. 14 shows allosteric regulation of UNC-49. A) Picrotoxin strongly inhibits UNC-49B homomers (closed circles) but only weakly inhibits UNC-49B/C heteromers (open circles). B) Pentobarbital enhances UNC-49B homomers (closed circles) more strongly than UNC-49B/C heteromers (open circles). Differences in maximal activation are significant (p<0.05), differences in IC50 and Hill number are not significant.

Figure 15:
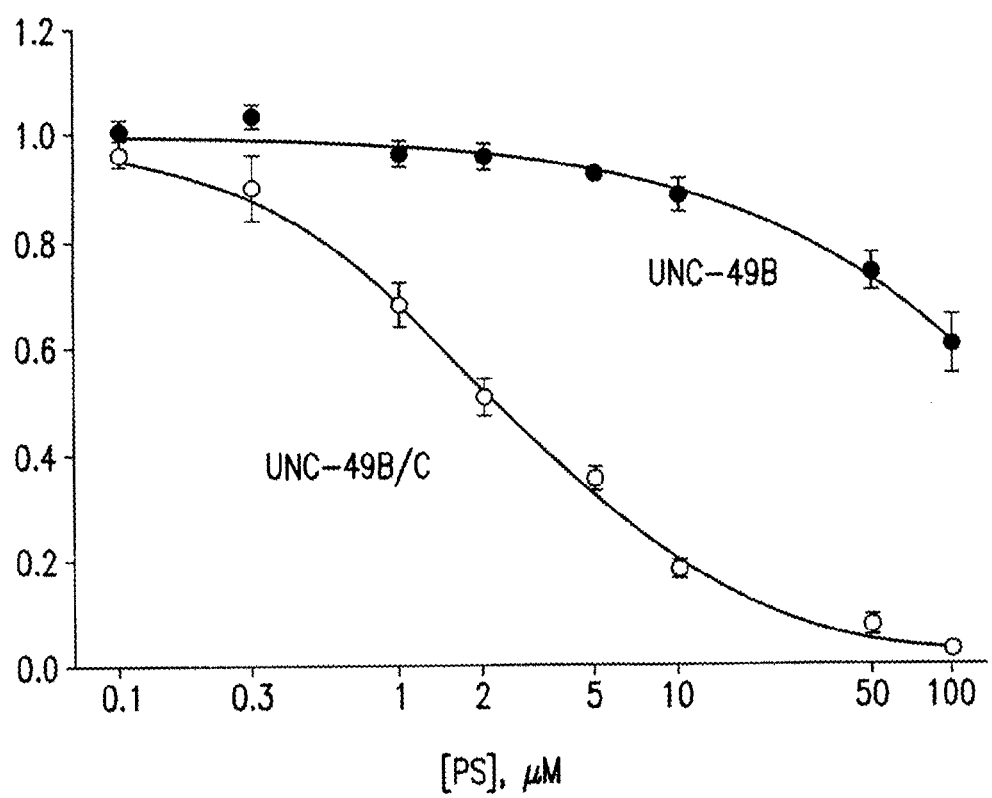

FIG. 15 shows differential PS sensitivity of UNC-49B homomers and UNC-49B/C heteromers.

Figure 16:
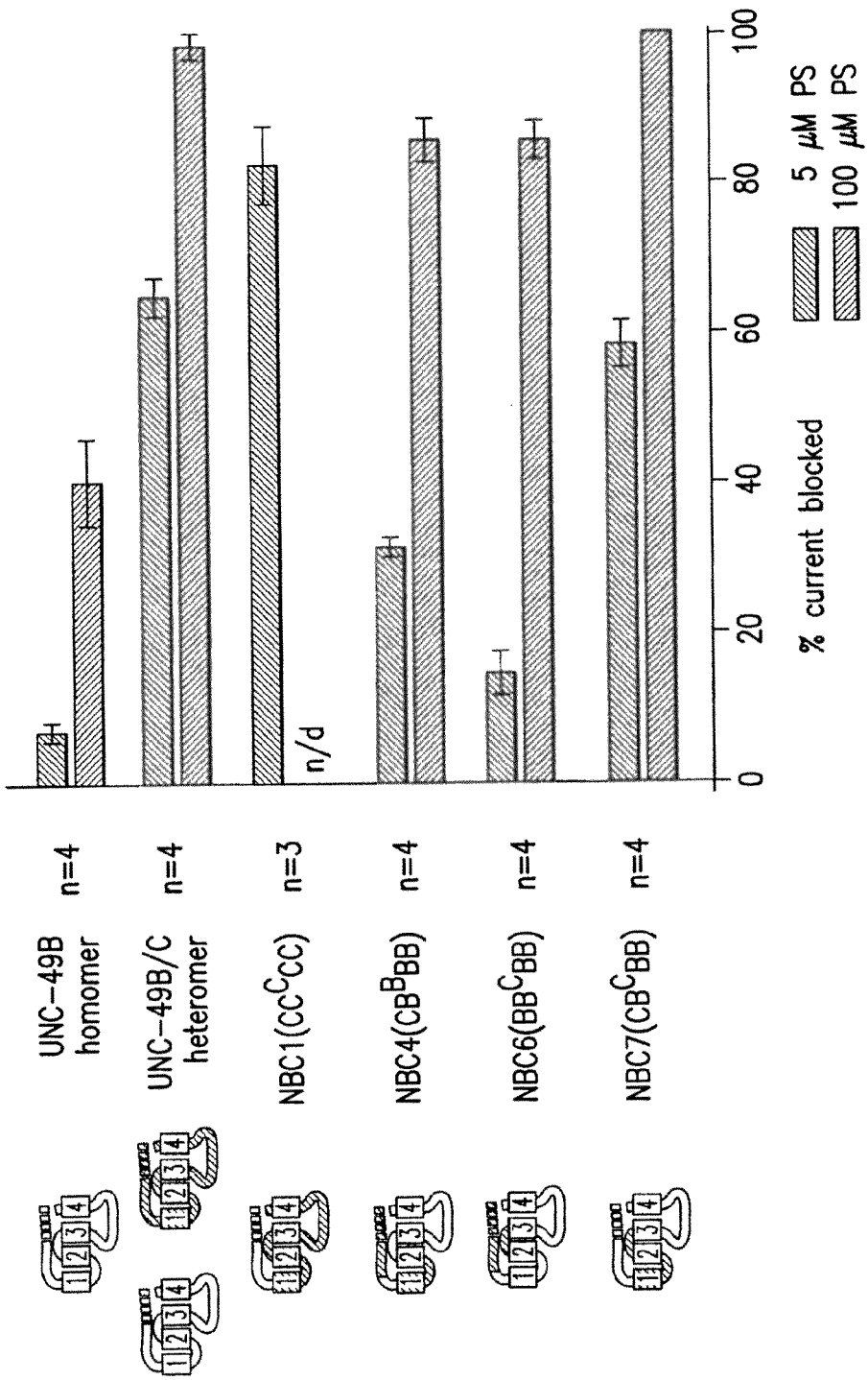

FIG. 16 shows structural determinants of PS sensitivity are located in the M1 and M2-3 loop domains of UNC-49 C. Common amino terminal sequences are shown in gray, UNC-49B sequences are shown in white, UNC-49C subunits are shown in black.

Figure 17C:
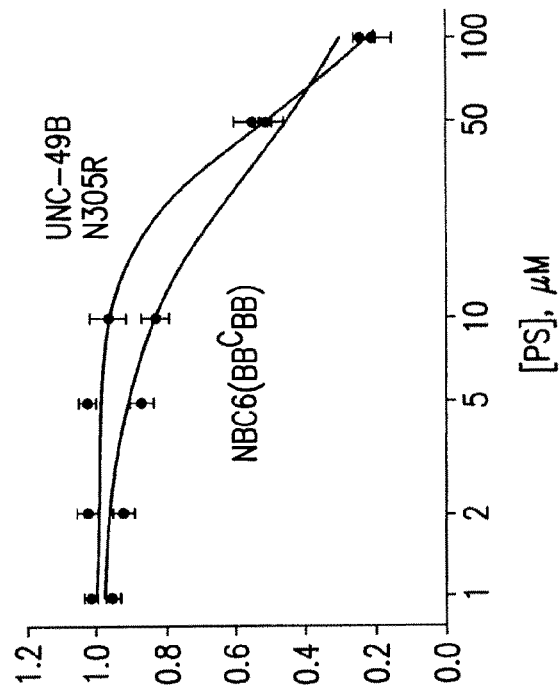
Figure 17B:
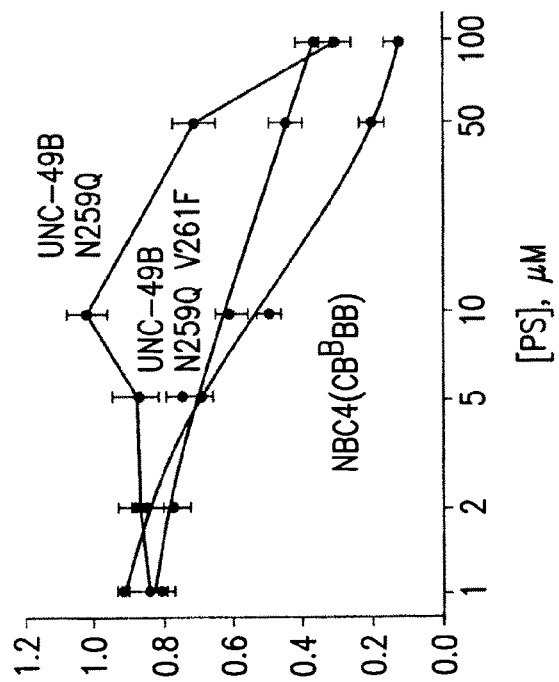

FIG. 17 shows residues required for PS sensitivity. A) Alignment of UNC-49B (SEQ ID NO: 26), UNC-49C (SEQ ID NO: 27), and representative mammalian $GABA_A$ receptors subunits α1 (SEQ ID NO: 28), β1 (SEQ ID NO: 29), and γ1 (SEQ ID NO: 30). Subunit domains are indicated by bars above sequence. Boxes indicate residues which are highly conserved among $GABA_A$ receptors (black boxes), but divergent in UNC-49B (open boxes). B, C) PS dose-response curves for the indicated mutant and chimeric subunits. All measurements were performed at the $EC_{50}$ for GABA.

Figure 18A:
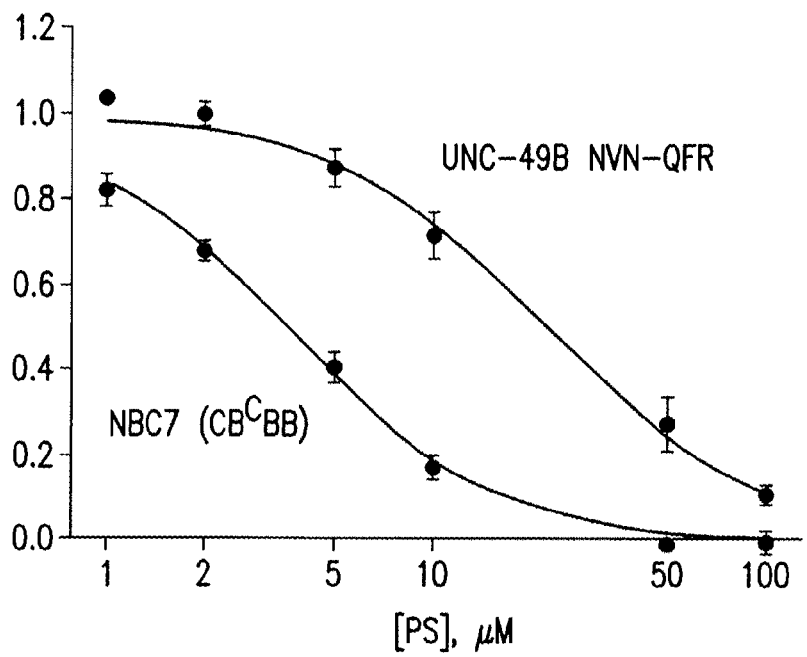
Figure 18B:
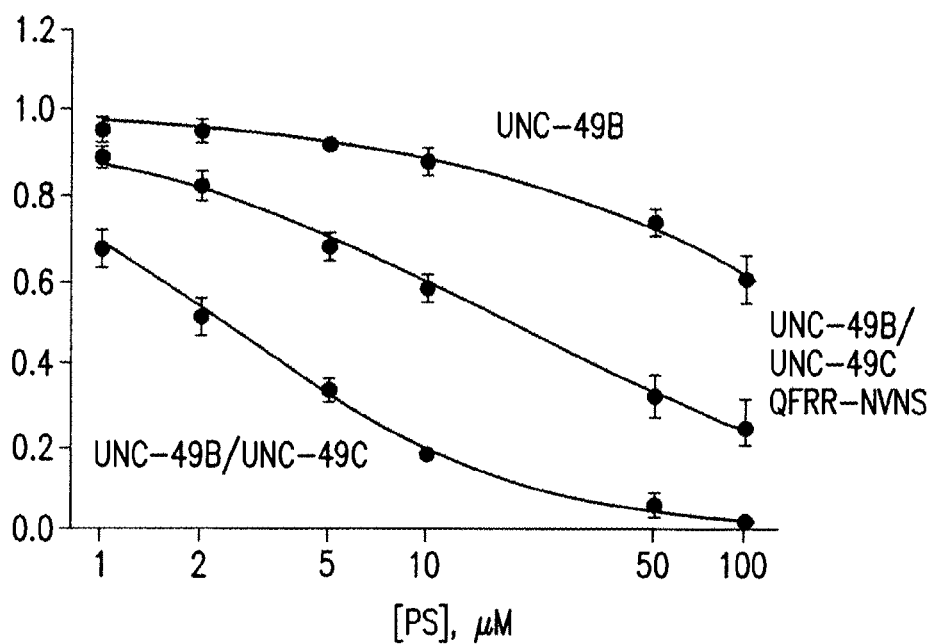

FIG. 18 shows additional residues are required for full PS sensitivity. A) PS dose-response curves for UNC-49B NVN-QFR triple mutant and the NBC7 chimera. B) PS dose-response curves for wild-type UNC-49B homomers and UNC-49B/C heteromers, and the UNC-49B/UNC-49C QFRR-NVNS heteromer.

Figure 19:
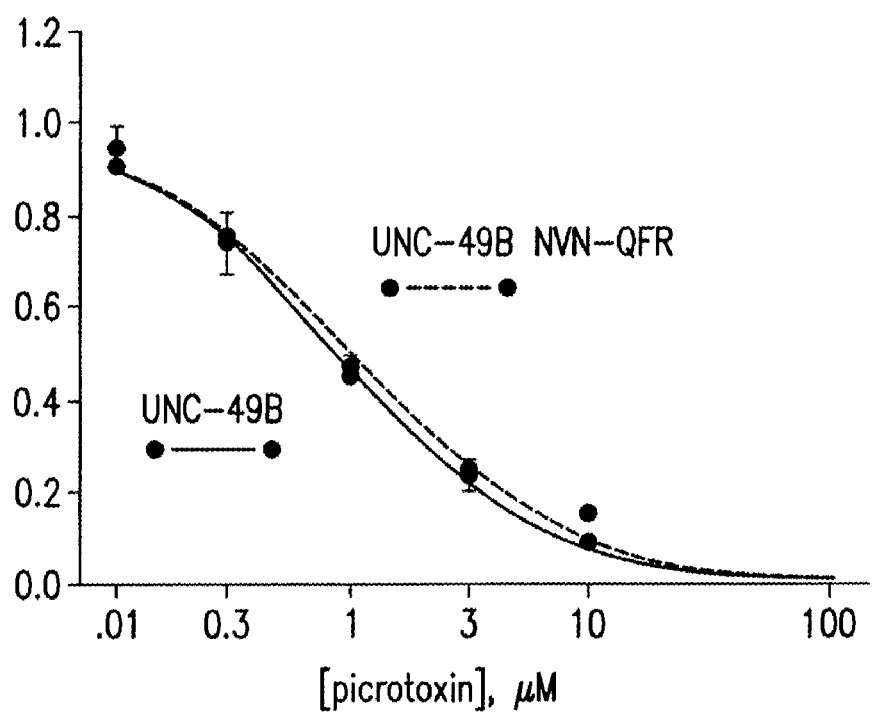

FIG. 19 shows picrotoxin dose-response curves for UNC-49B and UNC-49B NVN-QFR homomers.

Figure 20A:
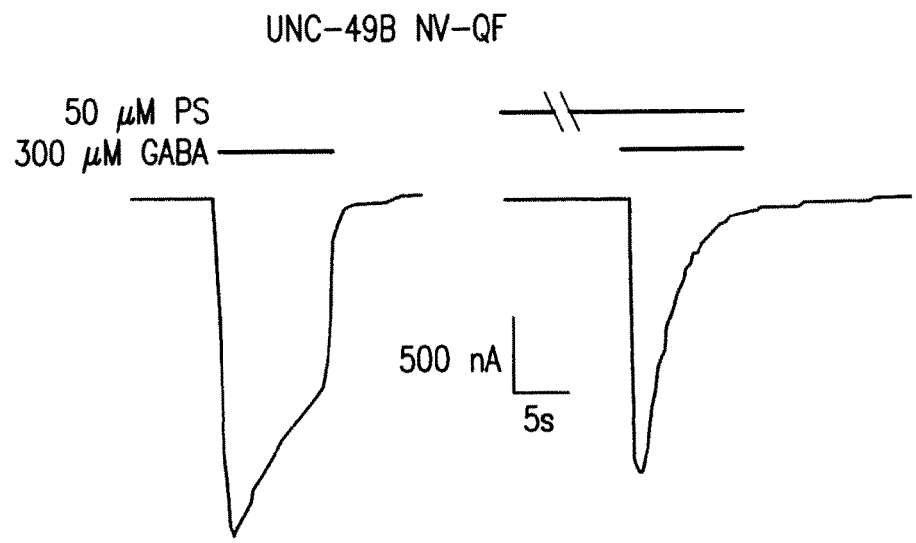
Figure 20B:
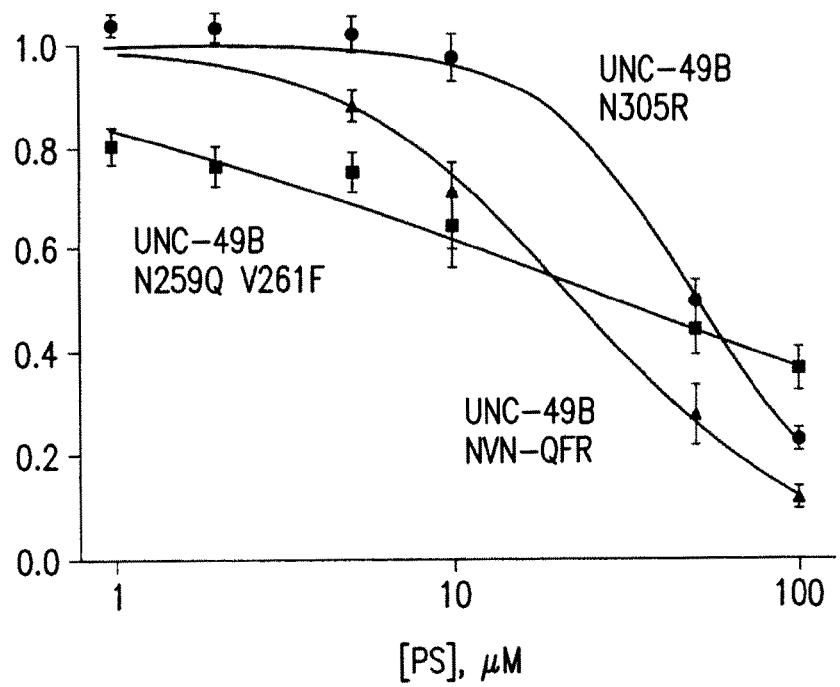

FIG. 20 shows evidence for multiple mechanisms of PS inhibition. A) PS causes accelerated desensitization in oocytes expressing UNC-49B homomers containing the M1 mutations. B) The M1 mutations and the M2-3 loop mutations do not produce additive effects when combined.

Figures 21A, 21B:
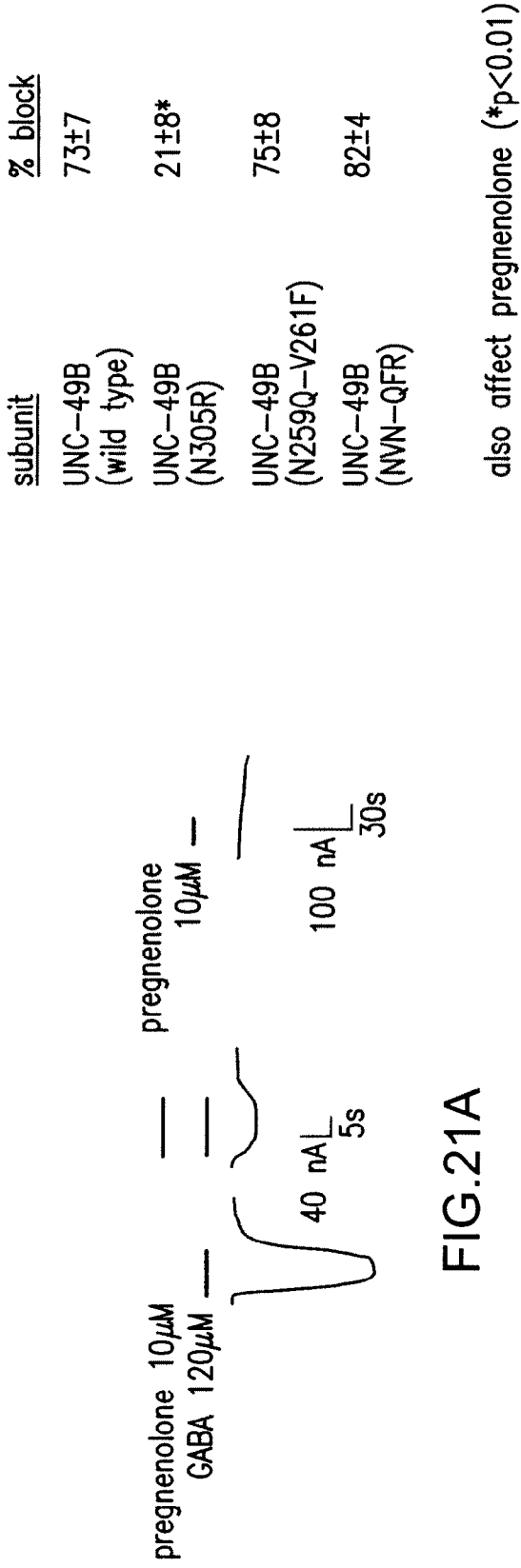

FIG. 21 shows pregnanolone response of UNC-49. A) Pregnanolone inhibits, rather than enhances, the UNC-49B homomer. B) Pregnanolone fails to directly activate the UNC-49B homomer.

Figure 22A:
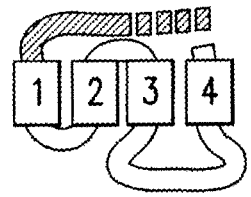
Figure 22B:
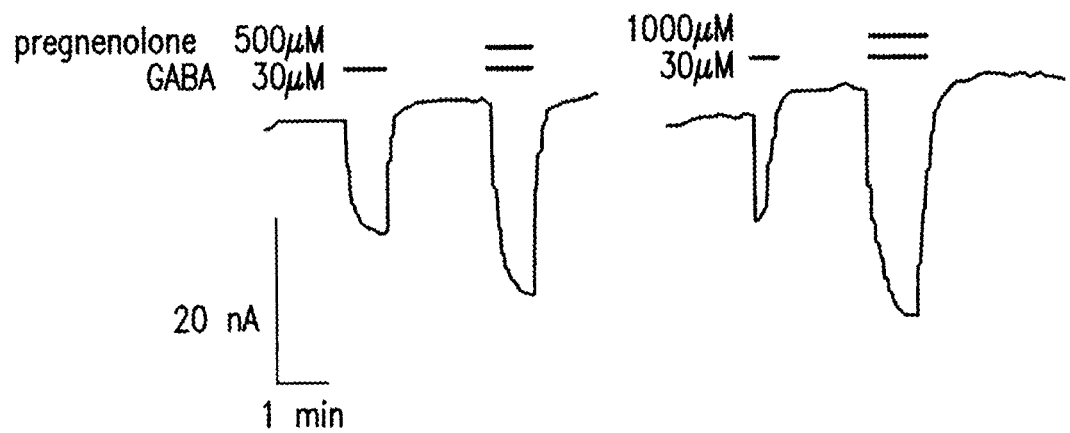
Figure 22C:
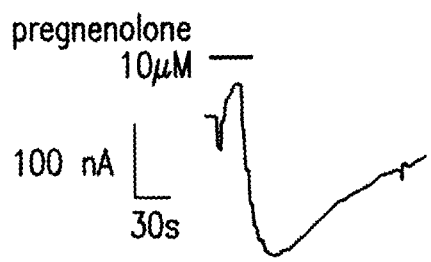

FIG. 22 shows the B-β3 chimera is sensitive to positive modulation by pregnanolone. A) Structure of the B-β3 chimera. B) The B-β3 chimera is enhanced by pregnanolone. C) The B-β3 chimera is directly activated by pregnanolone.

FIG. 23 shows desensitization kinetics of UNC-49B homomers and UNC-49B/C heteromers, and the effects of PS. A) Sample traces showing the response of UNC-49B homomers (top) and UNC-49B/C heteromers (bottom) to 500 ms pulses of GABA, in the presence and absence of 100 ☐M PS (in outside-out patches from transfected HEK cells). In all cases, desensitization was best fit by two exponentials, indicating one fast component and one slow component. B) Desensitization time-constants of UNC-49B homomers and UNC-49B/C heteromers, in the presence and absence of PS. The time constant is the amount of time required for the current to decay to a specific fraction (1/e) of the original, thus a smaller time constant reflects more rapid desensitization. $\tau_w$ is the weighted time constant. Pairs of values which are significantly different are marked with '*' (P<0.05).

Figure 24:
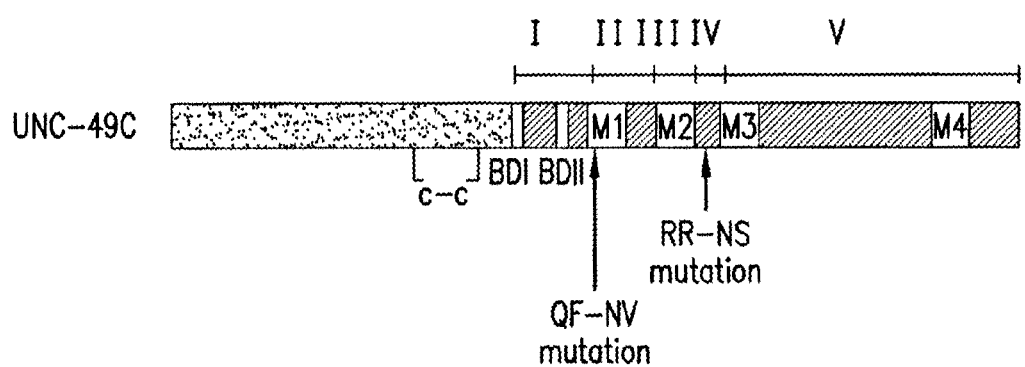

FIG. 24 shows regions of UNC-49C to be substituted with UNC-49B sequences. c-c: conserved cysteine loop; BDI, BDII: putative GABA binding domains.

Figure 25:
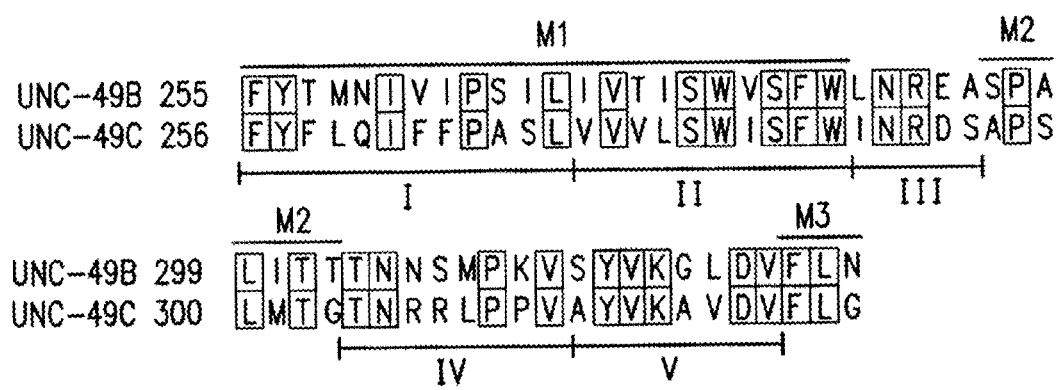

FIG. 25 shows UNC-49B sequence blocks to swap back into NBC7(CBCBB) (identities boxed). The sequence labeled UNC-49B corresponds to SEQ ID NO: 31 and the sequence labeled UNC-49C corresponds to SEQ ID NO: 32.

FIG. 26 shows alignment of UNC-49B (SEQ ID NO: 33) and the mammalian β3 subunit (SEQ ID NO: 34). β3 sequences top, UNC-49B sequences bottom. Conserved domains and sequence blocks shown. M3-M4 loop residues deleted at dashed line.

Figure 27:
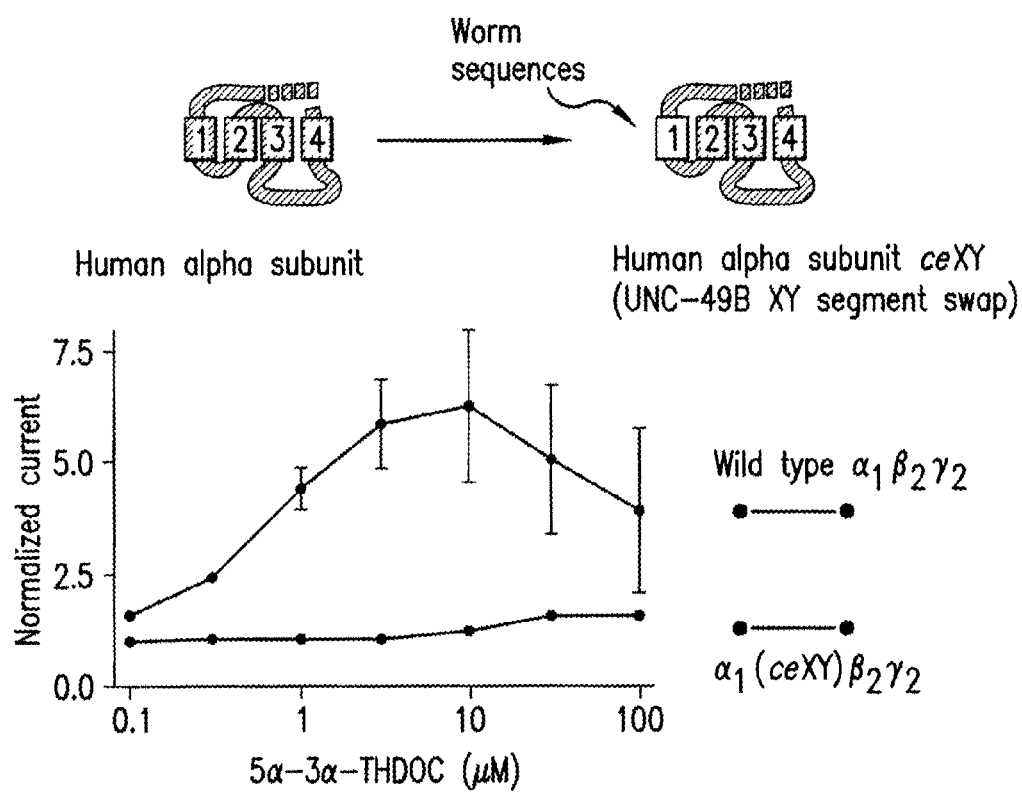

FIG. 27 shows that the same site controls neurosteroid enhancement of human $GABA_A$ receptors and in the nematode Caenorhabditis elegans.

Figure 28:
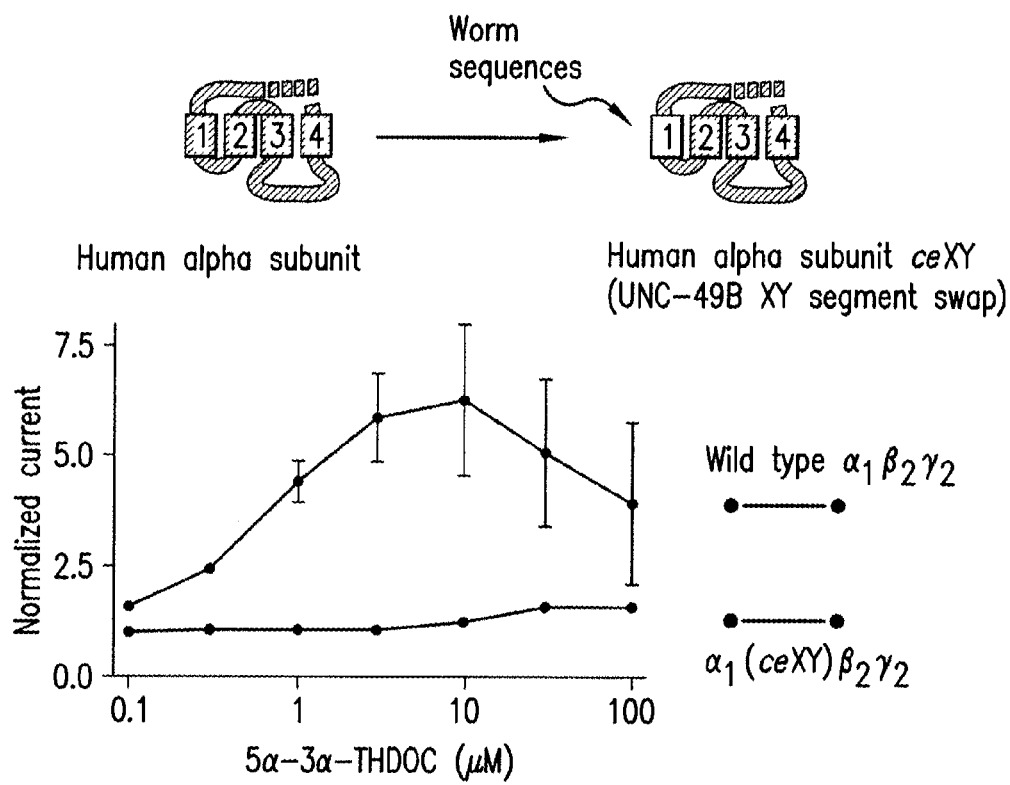

FIG. 28 shows the 'XY' segment of the altered mammalian GABAA receptor showed greatly-reduced positive modulation by the neurosteroid 5α-3α-THDOC (subunits expressed in Xenopus oocytes).

Figure 29A:
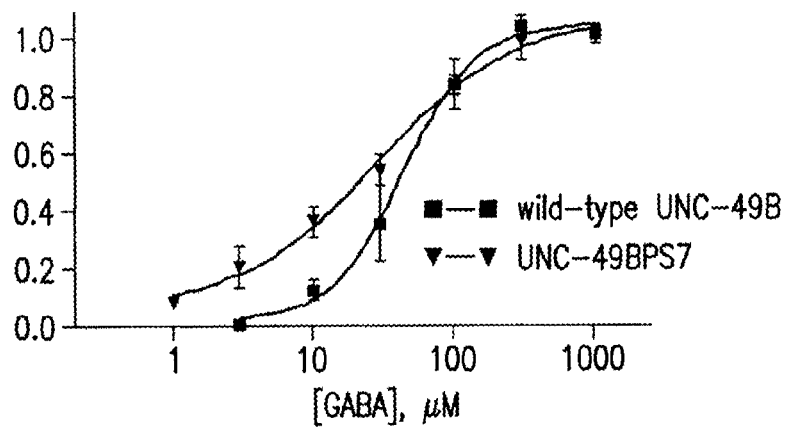
Figure 29B:
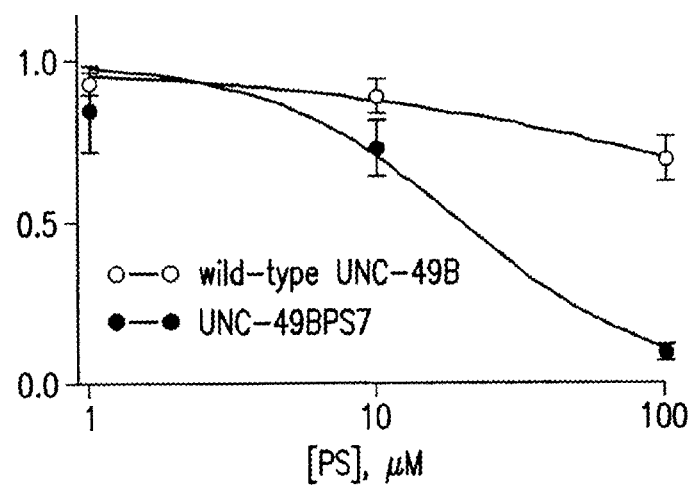

FIG. 29 shows GABA and neurosteroid sensitivities of wild-type and mutated $GABA_A$ receptors from C. elegans, expressed in mammalian HEK fibroblast cells.

VI. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a" "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein Typically a probe can be made from any combination of nucleotides or nucleotide derivatives or analogs available in the art.

The term "multiwell plate" refers to a two dimensional array of addressable wells located on a substantially flat surface. Multiwell plates can include any number of discrete addressable wells, and include addressable wells of any width or depth. Common examples of multiwell plates include 96 well plates, 384 well plates and 3456 well Nanoplates™. Such multiwell plates can be constructed of plastic, glass, or any essentially electrically nonconductive material The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination.

The term "hit" refers to a test compound that shows desired properties in an assay.

The term "repetitive" means to repeat at least twice.

The term "test compound" refers to a chemical to be tested by one or more screening method(s) of the invention as a putative modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.01 micromolar, 1 micromolar and 10 micromolar. Test compound controls can include the measurement of a signal in the absence of the test compound or comparison to a compound known to modulate the target.

The term "transgenic" is used to describe an organism that includes exogenous genetic material within all of its cells. The term includes any organism whose genome has been altered by in vitro manipulation of the early embryo or fertilized egg or by any transgenic technology to induce a specific gene knockout.

The term "transgene" refers to any piece of DNA which is inserted by artifice into a cell, and becomes part of the genome of the organism (i.e., either stably integrated or as a stable extrachromosomal element) which develops from that cell. Such a transgene can include a gene which is partly or entirely heterologous (i.e., foreign) to the transgenic organism, or may represent a gene homologous to an endogenous gene of the organism. Included within this definition is a transgene created by the providing of an RNA sequence that is transcribed into DNA and then incorporated into the genome. The transgenes of the invention include DNA sequences that encode the fluorescent or bioluminescent protein that may be expressed in a transgenic non-human animal.

The term "activity" as used herein refers to a measurable result of the interaction of molecules. Some exemplary methods of measuring these activity are provided herein.

The term "modulate" as used herein refers to the ability of a compound to change an activity in some measurable way as compared to an appropriate control. As a result of the presence of compounds in the assays, activities can increase (e.g. there could be increased levels of GABA receptor binding), or "decrease" (e.g. there could be decreased levels of GABA receptor binding) as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist". One that decreases, or prevents, a known activity is an "antagonist".

The term "monitoring" as used herein refers to any method in the art by which an activity can be measured.

The term "providing" as used herein refers to any means of adding a compound or molecule to something known in the art. Examples of providing can include the use of pipets, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition.

The term "treating" as used herein refers to administering a compound after the onset of clinical symptoms.

The term "in need of treatment" as used herein refers to a judgment made by a caregiver (e.g. physician, nurse, nurse practitioner, or individual in the case of humans; veterinarian in the case of animals, including non-human mammals) that an individual or animal requires or will benefit from treatment. This judgment is made based on a variety of factors that are in the realm of a care giver's expertise, but that include the knowledge that the individual or animal is ill, or will be ill, as the result of a condition that is treatable by the compounds of the invention.

The term "individual" as used herein refers to a mammal, including animals, preferably mice, rats, other rodents, rabbits, dogs, cats, swine, cattle, sheep, horses, or primates, most preferably humans.

The term "non-human animal" refers to any non-human vertebrate, birds and more usually mammals, preferably primates, animals such as swine, goats, sheep, donkeys, horses, cats, dogs, rabbits or rodents, more preferably rats or mice. Both the terms "animal" and "mammal" expressly embrace human subjects unless preceded with the term "non-human".

The terms "higher," "increases," "elevates," or "elevation" refer to increases above basal levels, e.g., as compared to a control. The terms "low," "lower," "reduces," or "reduction" refer to decreases below basal levels, e.g., as compared to a control.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. General

Residues important for the actions of other allosteric regulators of $GABA_A$ receptors affect neurosteroid modulation as well (Akk et al., 2001; Chang et al., 2003; Morris & Amin, 2004). Thus, neurosteroids can use some of the same general mechanisms to modulate $GABA_A$ receptor function as other allosteric regulators. However, other $GABA_A$ receptor residues can mediate neurosteroid action specifically, for example, by forming a neurosteroid binding pocket. Further, the mechanisms of neurosteroid enhancement and inhibition can be different (Park-Chung et al., 1999; Zaman et al., 1992), showing that some receptor residues can play roles specific to individual neurosteroids.

Differential drug sensitivities of $GABA_A$ receptor subunits in the nematode *Caenorhabditis elegans* have been found. The gene unc-49 encodes multiple GABA receptor subunits (Bamber et al., 1999, herein incorporated by reference in its entirety) that are closely related to mammalian $GABA_A$ receptors (Bamber et al., 2003, herein incorporated by reference in its entirety). Like their mammalian homologs, UNC-49 subunits contain a large extracellular amino terminal region, and four transmembrane domains labeled M1-M4. Five subunits assemble to form a pentameric chloride channel, with the M2 domain from each subunit contributing the pore-lining residues (reviewed in (Olsen & Tobin, 1990, herein incorporated by reference in its entirety). In vivo, UNC-49B co-assembles with UNC-49C to form a $GABA_A$ receptor that functions at the neuromuscular junction to permit coordinated locomotion (Bamber et al., 2005, herein incorporated by reference in its entirety). However, UNC-49B subunits (but not UNC-49C subunits) can also efficiently form homomeric receptors. The *C. elegans* GABA receptor is neurosteroid sensitive. Both UNC-49B homomers and UNC-49B/C heteromers are, atypically, inhibited by pregnanolone (Bamber et al., 2003). Interestingly, the two forms of this receptor show differential pregnenolone sulfate (PS) sensitivity: PS inhibits the UNC-49B/C heteromer much more strongly than the UNC-49B homomer. This finding shows that UNC-49C contains sequences important for pregnenolone sulfate modulation. By swapping residues from UNC-49C into UNC-49B this PS-insensitive receptor was converted into a PS-sensitive receptor. First, chimeras of these two subunits were created to demonstrate that the M1 and M2-M3 linker domains are important for PS sensitivity. Second, roles for residues within these domains that are conserved among neurosteroid-sensitive receptors but divergent in UNC-49B were demonstrated. Third, using systematic mutagenesis of the M1 domain, additional residues that control PS sensitivity were identified. Mutations in critical M1 residues have little or no effect on the sensitivity of the receptor to the allosteric inhibitor picrotoxin, showing that residues with a specific role in GABA receptor modulation by neurosteroids have been found.

It has been shown that one variant of the XY segment conferred high PS sensitivity (the UNC-49C sequence) (Example 1), while another variant of the XY segment conferred low PS sensitivity (the UNC-49B sequence). Subunits of mammalian $GABA_A$ receptors also contain an XY segment. It was tested whether neurosteroid sensitivity of mammalian receptors similarly depended on their XY segments. The mammalian XY segment (within the α1 subunit) was replaced with the low-sensitivity UNC-49B XY sequence variant. It was determined that the altered mammalian receptor showed greatly-reduced positive modulation by the neurosteroid 5α-3α-THDOC compared to the wild-type receptor (FIG. 28). This result is significant for two reasons: First, it demonstrates that neurosteroids act through the same site on *C. elegans* and mammalian $GABA_A$ receptors; second, it provides evidence that positive modulatory neurosteroids (such as 5α-3α-THDOC) act through the same part of the receptor as negative modulatory neurosteroids (such as PS). Both positive and negative modulation of $GABA_A$ receptors are therapeutically beneficial.

Disclosed herein is a $GABA_A$ receptor with a mutation in the transmembrane region, wherein the mutation confers altered drug specificity to the receptor. The mutation can be in the M1 domain, such as in the XY region, or in the M2-M3 extracellular region, or in both. The mutation in the M2-M3 domain can comprise an asparagine to arginine change at position 305. for example. The mutation in the M1 domain can also comprise a mutation in L258, Q259, F262 or S265. The drug can be a neurosteroid, such as pregnenolone sulfate. In one embodiment, the mutated receptor does not mediate the effect of a non-steroid drug, such as picrotoxin. The mutated receptor can retain the same ability to interact with picrotoxin as the wild-type receptor.

Disclosed herein is a method of modulating $GABA_A$ receptor function, comprising contacting the transmembrane domain with a ligand thereof. Also disclosed is a method of modulating $GABA_A$ receptor function, comprising contacting the M1 domain with a ligand thereof. Disclosed is a method of modulating $GABA_A$ receptor function, comprising contacting the M2-M3 linker domain with a ligand thereof.

Disclosed herein is a method of modulating $GABA_A$ receptor function, comprising contacting the M1 and M2-M3 linker domain with a ligand thereof. Modulation can comprise increasing or decreasing receptor activity. The ligand can be a neurosteroid, for example.

Disclosed herein is a method of modulating $GABA_A$ receptor function in a subject in need thereof, comprising: a) identifying a subject in need of neurosteroid treatment; b) administering to the subject an effective amount of a ligand that modulates $GABA_A$ receptor function, thereby modulating $GABA_A$ receptor function in a subject in need thereof. The modulation can occur in the M1 region of the $GABA_A$ receptor, such as in the XY region. The modulation can occur in the M2-M3 region of the $GABA_A$ receptor. The modulation can occur in both the M1 region of the $GABA_A$ receptor and the M2-M3 region.

Disclosed herein is a method of increasing neurosteroid sensitivity in $GABA_A$ receptors, comprising mutating the residue at position 305 of SEQ ID NO: 3 to a positively charged residue. The positively charged residue can comprise arginine.

Also disclosed is an assay comprising a $GABA_A$ receptor, wherein the $GABA_A$ receptor comprises a mutated residue at position 305 of SEQ ID NO: 3. The mutation can comprise a positively charged residue, such as arginine.

Disclosed is a polypeptide comprising SEQ ID NO: 3, wherein the asparagine residue has been mutated to arginine at position 305.

Also disclosed is a method for treating neurological disorders comprising administering to a subject in need thereof a composition that targets the transmembrane domain of the $GABA_A$ receptor.

Disclosed herein is a method of screening for compounds that modulate $GABA_A$ receptors at a location of interest on the receptor, comprising exposing a test compound to a modified $GABA_A$ receptor, wherein the modification is at the location of interest on the receptor; and detecting altered binding of the test compound to the modified $GABA_A$ receptor compared to a wild type $GABA_A$ receptor, wherein altered binding is indicative of a compound that modulates the $GABA_A$ receptor at the location of interest. The screening can be high throughput. The location of interest can be the transmembrane region, such as in the M1 region, specifically the XY region. The location of interest can also be in the M2-M3 region. The location of interest can comprise more than one location, such as the M1 and M2-M3 region. The mutation can comprise a mutated residue at position 305. The modulation can comprise an increase or a decrease in receptor interaction. The activity of the compound being screened can be compared to that found when the compound interacts with a wild type receptor Disclosed herein is a method of screening a test compound that modulates a $GABA_A$ receptor at a location of interest on the receptor comprising the following steps: a) measuring the response of the test compound to a cell expressing the wild-type $GABA_A$ receptor; b) measuring the response of the test compound to a cell expressing a mutated $GABA_A$ receptor, wherein the mutation is in the location of interest; c) comparing the response of the test compound in steps a) and b); d) determining if the test compound modulates the $GABA_A$ receptor at the location of interest based on the results of step c).

Also disclosed is a method of screening a test compound that modulates a $GABA_A$ receptor at a location of interest on the receptor comprising the following steps: a) measuring the response of cells expressing the wild-type $GABA_A$ receptor to GABA; b) measuring the response of cells expressing a mutant $GABA_A$ receptor to GABA, wherein the mutation is in the location of interest; c) measuring the response of cells expressing the wild-type $GABA_A$ receptor to GABA plus the test compound; d) measuring the response of cells expressing the mutant $GABA_A$ receptor, wherein the mutation is in the location of interest, to GABA plus the test compound; e) comparing the results of steps c) and d); wherein a difference in response of the test compound in the presence of wild-type versus mutated $GABA_A$ receptor indicates a compound that modulates a $GABA_A$ receptor at the location of interest.

In the screening methods disclosed above, the screening can be high throughput. The location of interest can be in the transmembrane region, such as the M1 region, specifically the XY region. The location of interest can also be in the M2-M3 region. The mutation can comprise a mutated residue at position 305.

The modulation can comprise an increase or a decrease in receptor interaction. The measuring steps can comprise measuring the response at various concentrations of test compound. The measuring steps can also comprise measuring the response at various concentrations of GABA.

Also disclosed herein is a method of increasing neurosteroid sensitivity in $GABA_A$ receptors, comprising mutating the residue at position 305 of SEQ ID NO: 1 to a positively charged residue, such as N305R.

Further disclosed are methods of treating neurological disorders comprising administering to a subject in need thereof a composition that targets the transmembrane domain of the $GABA_A$ receptor, such as the M1 and the M2-M3 linker domain.

Disclosed herein are methods of treating specific diseases and disorders involving the central nervous system. A variety of diseases and disorders can be treated with the methods and compositions disclosed herein, including stroke and related ischemic diseases, spinal cord injuries, peripheral nerve injuries, traumatic brain injuries, retinal degeneration, neurodegenerative disorders, cataracts, antibiotic-induced ototoxicity, Alzheimer's disease, Amyotrophic Lateral Sclerosis (ALS, Lou Gehrig's disease), epilepsy (such as generalized, partial, or refractory epilepsy), Huntington's disease, Parkinson's disease, and Multiple Sclerosis. Methods and routes of administration, dosages, and pharmaceutical compositions are discussed in more detail below.

Also disclosed are methods of treating pain and other neurological disorders comprising administering to a subject in need thereof an effective amount of the polypeptides disclosed herein.

The methods and compositions disclosed herein can also be used in the prevention, amelioration, or treatment of neurological disorders, such as those disclosed above and known to those of skill in the art.

The methods and compositions disclosed herein can be used with various compositions, such as the methods of screening disclosed herein, as well as treatment methods. For example, the following drugs and classes of drugs can be used for pain, epilepsy, neuroprotection, and depression, bipolar, other psychiatric disorders: opioids and opioid peptides, morphine, hydroxymorphine, fentanyl, oxycodone, codeine; capsaicin; as well as antiepileptic drugs as a class including but not limited to carbamazepine, primidone, gabapentin, pregabalin, diazepam, felbamate, fluorofelbamate, lamotrigine, lacosamide, levetiracetam, phenobarbital, phenytoin, fosphenytoin, topiramate, valproate, vigabatrin, zonisamide, oxcarbazepine, nonsteroidal anti-inflammatory drugs (NSAIDs), local anesthetics (such as lidocaine), glutamate receptor antagonists, NMDA antagonists, alpha-adrenoceptor agonists and antagonists, adenosine, cannabinoids, NK-1 antagonist (CI-1021), antidepressants (amitriptyline, desipramine, imipramine, for example), analogs and derivatives of galanin, somatostatin, delta-sleep inducing peptide, enkephalins, oxytocin. cholecystikinin, calcitonin, cortistatin, nociceptin and other neuropeptide-based therapeutics, and pluronic P85 block copolymer.

C. Compositions

Disclosed are the components to be used to prepare the disclosed compositions as well as the compositions themselves and to be used within the methods disclosed herein. These and other materials are disclosed herein, and it is understood that when combinations, subsets, interactions, groups, etc. of these materials are disclosed that while specific reference to each various individual and collective combinations and permutation of these compounds may not be explicitly disclosed, each is specifically contemplated and described herein. For example, if a particular $GABA_A$ receptor is disclosed and discussed and a number of modifications that can be made to a number of molecules including the variant are discussed, specifically contemplated is each and every combination and permutation of the $GABA_A$ receptors and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 40, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710,1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Regarding alignment, it should be noted that throughout this application, reference is given to various residues at various positions of an UNC-49 receptor. Although this specific position is referred to in order to have a reference point, it is noted that this reference includes corresponding residues in other receptors, even if the numbering is not the same. For example, one may refer to residue 305 of UNC-49B, but the corresponding residue on UNC-49C, or another receptor, is also included in that definition, even if the residue position number is different in another receptor. When the sequences for the receptors are aligned, one of skill in the art can determine a corresponding residue.

2. Nucleic Acids

There are a variety of molecules disclosed herein, such as various compositions and receptors. It is understood that these peptide based molecules can be encoded by a number of nucleic acids, including for example the nucleic acids that encode, for example, SEQ ID NOS 1 and 3, and it is understood that for example, when a vector is expressed in a cell, that the expressed mRNA will typically be made up of A, C, G, and U.

a) Sequences

There are a variety of sequences related to, for example, $GABA_A$ receptors, which can be found at, for example, Genbank database which can be accessed at www.pubmed.gov. These sequences and others are herein incorporated by reference in their entireties as well as for individual subsequences contained therein.

One particular sequence set forth in SEQ ID NO: 3 is used herein, as an example, to exemplify the disclosed compositions and methods. Those of skill in the art understand how to resolve sequence discrepancies and differences and to adjust the compositions and methods relating to a particular sequence to other related sequences. Primers and/or probes can be designed for any receptor-related nucleic acid sequence, for example, given the information disclosed herein and known in the art.

3. Delivery of the Compositions to Cells (Vectors)

There are a number of compositions and methods which can be used to deliver nucleic acids or peptides to cells, either in vitro or in vivo. The vectors disclosed herein can be used in multiple ways. In one example, the vectors disclosed herein can be used to deliver nucleic acids encoding the peptides disclosed herein to cells and subjects.

Methods and compositions relating to vectors can largely be broken down into two classes: viral based delivery systems and non-viral based delivery systems. For example, nucleic acids and peptides can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

As used herein, plasmid or viral vectors are agents that transport the disclosed nucleic acids or peptides into the cell without degradation. In some embodiments the delivery systems are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

4. Peptides a) Protein Variants

As discussed herein there are numerous variants of a peptide that are known and herein contemplated. In addition, to the disclosed functional variants and analogs related to the positions disclosed herein, there are known functional naturally occurring variants at positions other than those disclosed herein, which also function as desired. Protein variants and derivatives are well understood to those of skill in the art and can involve amino acid sequence modifications or functional fragments. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations | |
|---|---|---|
| alanine | Ala | A |
| allosoleucine | AIle | |
| arginine | Arg | R |
| asparagine | Asn | N |
| aspartic acid | Asp | D |
| cysteine | Cys | C |
| glutamic acid | Glu | E |
| glutamine | Gln | Q |
| glycine | Gly | G |
| histidine | His | H |
| isolelucine | Ile | I |
| leucine | Leu | L |
| lysine | Lys | K |
| phenylalanine | Phe | F |
| proline | Pro | P |
| pyroglutamic acid | pGlu | |
| serine | Ser | S |
| threonine | Thr | T |
| tyrosine | Tyr | Y |
| tryptophan | Trp | W |
| valine | Val | V |

TABLE 2

Amino Acid Substitutions
Original Residue Exemplary Conservative Substitutions,
others are known in the art.

| | |
|---|---|
| Ala | ser |
| Arg | lys, gln, his |
| Asn | gln; his |
| Asp | glu |
| Cys | ser |
| Gln | asn, lys |
| Glu | asp |
| Gly | Ala |
| His | asn; gln |
| Ile | leu; val |
| Leu | ile; val |
| Lys | arg; gln; his |
| Met | Leu; ile |
| Phe | met; leu; tyr |
| Ser | thr, asn |
| Thr | ser, gln |
| Trp | tyr |
| Tyr | trp; phe |
| Val | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert or disable sites for N-glycosylation (Asn-X-Thr/Ser) or O-glycosylation (Ser or Thr). Deletions or substitutions of cysteine or methionine (for example in "neutrophil-resistant" proteins due to generation of oxidants by neutrophils) or other labile residues also may be desirable. Deletions or substitutions of potential proteolysis sites, e.g. Arg, may be accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of amines in the epsilon-amino group of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

Disulfide bonds are covalent interactions between the thiol group of two cysteine molecules. Through an oxidative reaction, the hydrogen atoms are removed from the thiol groups allowing the formation of a disulfide bridge; the resulting bonded cysteines are termed cystine. Disulfide bonds fall into to categories class I and class II. It is a class II bond which serves to stabilize the three dimensional structure of a protein by linking cysteines within a chain. A class I disulfide bond results when these interactions occur between separate chains. The formation of class I disulfide bonds can aid in the formation of dimeric proteins, an important feature which is often necessary for receptors to provide proper receptor-ligand interactions. Amino acid substitutions may be made at sites where cysteine residues occur; typically, conservative substitutions do not alter cysteine residues involved in disulfide bonds. Such substitutions may have the effect of changing protein folding or altering multimer interactions if the substituted residue is involved in disulfide bonds. It can be determined which cysteines are involved in disulfide bonds.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein in the particular organism from which that protein arises is also known and herein disclosed and described.

Also disclosed are fragments of the disclosed proteins and variants. Typically these fragments will retain at least one of the functions described herein, such as increased interaction with a given $GABA_A$ receptor. However, it is understood that fragments that do not retain this activity, for example, can still be used to, for example, generate antibodies. These activities can be related but are not necessarily required. Those of skill understand how to manipulate functional domains of the disclosed analogs by, for example, altering a region contributing to a particular function.

5. Antibodies

Antibodies as disclosed herein can be useful in identifying analogs with a desired function. As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (1), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain increased permeability are included within the meaning of the term "antibody or fragment thereof." Such antibodies and fragments can be made by techniques known in the art and can be screened for specificity and activity according to the methods set forth in the general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

6. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, and topical intranasal administration or administration by inhalant can be used. The exact amount of the compositions required will vary from subject to subject, depending on the species, age, weight and general condition of the subject the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.,* 35:421-425, (1992); Pietersz and McKenzie, *Immunolog. Reviews,* 129: 57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including opthalmically, vaginally, rectally, intranasally), orally, by inhalation, or parenterally, for example by intravenous drip, subcutaneous, intraperitoneal or intramuscular injection. The disclosed compositions can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

The dosage ranges for the administration of the compositions are those large enough to produce the desired effect in which the symptom's of the disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any contraindications.

Dosage can vary, and can be administered in one or more dose administrations daily, for one or several days.

7. Chips and Microarrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

Also disclosed are chips where at least one address is the sequences or part of the sequences set forth in any of the nucleic acid sequences disclosed herein wherein the sequence includes at least one of the variant sequences disclosed herein. Also disclosed are chips where at least one address is the sequences or portion of sequences set forth in any of the peptide sequences disclosed herein, wherein the peptide sequence comprises at least one of the mutations disclosed herein.

Also disclosed are chips where at least one address is the sequences or part of the sequences set forth in any of the nucleic acid sequences disclosed herein wherein the sequence includes at least one of the variant sequences within the region defined herein. Also disclosed are chips where at least one address is the sequences or portion of sequences set forth in any of the peptide sequences disclosed herein, wherein the peptide sequence comprises at least one of the substitutions, additions, mutations, or deletions disclosed herein.

8. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums are. Thus, computer readable mediums on which the nucleic acids or protein sequences are recorded, stored, or saved are disclosed.

Disclosed are computer readable mediums comprising the sequences and information regarding the sequences set forth herein.

9. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include amino acids to perform the substitutions discussed in certain embodiments of the methods, as well as instructions.

10. Compositions with Similar Functions

It is understood that the compositions disclosed herein have certain functions, such as increased interaction with a $GABA_A$ receptor. Disclosed herein are certain structural requirements for performing the disclosed functions, and it is understood that there are a variety of structures which can perform the same function which are related to the disclosed structures, and that these structures will ultimately achieve the same result.

11. Knockout/Transgenic Models

For use as disease models and to test compounds identified herein, modified $GABA_A$ receptor subunits such as those described herein can be used in transgenic and knock-out animals may be produced and utilized. For use as disease models, to test compounds identified herein, and to identify modulators of $GABA_A$, transgenic and knock-out mice and animals comprising modified components of the desensitization pathway described herein may be produced and utilized. The animal may, for example, be a mouse or an animal as listed herein. Examples related to knock-out animals are described herein. Certain non-limiting embodiments refer specifically to a knock-out mouse, but are intended to encompass animals as described herein.

The cells of the animal can comprise at least one $GABA_A$ receptor subunit mutation. The mouse may be a complete knockout or homozygous for the inactive $GABA_A$ subunit receptor, or the mouse can be a partial knockout or heterozygous for the $GABA_A$ subunit receptor.

The knockout animal may be useful for verification that a compound is in fact a $GABA_A$ receptor modulator. For example, the knockout animal of the present invention can be used as a model for comparison with wild-type mice that have been treated with a $GABA_A$ receptor modulator. This comparison may be used to verify that the compound administered to the wild-type mice is a $GABA_A$ receptor modulator.

The knockout animal may also be useful for verification that a compound is in fact a $GABA_A$ receptor activator or inhibitor (such as an agonist or inverse agonist). For example, partial knockout mice that have been treated with a $GABA_A$ receptor activator or inhibitor may be used as a model for comparison with wild-type mice and complete knockout mice. This comparison may be used to verify that the compound administered is a $GABA_A$ receptor activator or inhibitor.

The production of $GABA_A$ receptor knockout mice can be carried out in view of the disclosure provided herein and in light of techniques known to those skilled in the art, such as described in U.S. Ser. No. 09/469,554, filed Dec. 22, 1999, U.S. Pat. No. 5,767,337 to Roses et al.; U.S. Pat. No. 5,569,827 to Kessous-Elbaz et al.; and U.S. Pat. No. 5,569,824 to Donehower et al. (the disclosures of which are hereby incorporated by reference in their entirety); and A. Harada et al., Nature 369, 488 (1994).

D. Methods of Using the Compositions

1. Methods of Screening for Compounds which Modulate $GABA_A$ Receptors

Disclosed herein is a method of screening for a compound that modulates a $GABA_A$ receptor at a location of interest on the receptor comprising the following steps: a) measuring the response of a cell expressing the wild-type GABAA receptor to the test compound; b) measuring the response of a cell expressing a mutated $GABA_A$ receptor to the test compound, wherein the mutation is in the location of interest; c) comparing the response of the cell to the test compound in steps a) and b); and d) determining if the test compound modulates the $GABA_A$ receptor at the location of interest based on the results of step c).

Also disclosed is a method of screening for a compound that modulates GABA comprising: a) measuring the response of cells expressing a $GABA_A$ receptor to GABA; b) measuring the response of cells expressing $GABA_A$ receptor to GABA plus the test compound; c) comparing the measurements of step a) and b); wherein a difference in response of a cell in the presence of a test compound versus not in the presence of a test compound indicates a compound that modulates GABA.

Also disclosed is a method of screening for a compound that modulates GABA comprising: a) measuring the response of cells expressing wild-type $GABA_A$ receptor to GABA; b) measuring the response of cells expressing a mutant $GABA_A$ receptor to GABA, wherein the mutation is in the location of interest; c) comparing the measurements of step a) and b); d) measuring the response of cells expressing the wild-type $GABA_A$ receptor to GABA plus the test compound; e) measuring the response of cells expressing the mutant $GABA_A$ receptor, wherein the mutation is in the location of interest, to GABA plus the test compound; f) comparing the measurements of d) and e); and g) comparing the results of steps c and f); wherein a difference in response of a cell in the presence of a test compound versus not in the presence of a test compound indicates a compound that modulates GABA. In this method, the $GABA_A$ receptor can be mutated or wild type.

In the above method, the activity of GABA is first compared to a wild type, and then a mutant $GABA_A$ receptor. This is done to determine the activity of GABA in the presence of the mutation. If GABA activity changes in the presence of the mutation, then it is clear that the mutation affects GABA activity. If GABA activity is not changed in the presence of the mutation, then the mutation does not affect GABA activity. The test compound can act at the site of the mutation, but does not have to.

The modulation can comprise an increase in receptor interaction or GABA activity. By an "increase" is meant that the receptor interaction or GABA activity is greater in the presence of the test compound than not in the presence of the test compound. The modulation can also comprise a decrease in receptor interaction or GABA activity. By a "decrease" is meant that the receptor interaction or GABA activity is less in the presence of the test compound than not in the presence of the test compound.

The response of GABA activity or receptor interaction can be measured in the presence of various concentrations of test compound. The measuring steps can also comprise measuring the response at various concentrations of GABA. For example, the concentration of GABA or the test compound can range from 1 nM to 1000 µM. In one example, there can be twelve concentrations at 1 nM, 3 nM, 10 nM, 30 nM, etc.

Assays contemplated by the invention include both binding assays and activity assays; these assays may be performed in conventional or high throughput formats. Modulator screens are designed to identify stimulatory and inhibitory agents. The sources for potential agents to be screened include natural sources, such as a cell extract (e.g., invertebrate cells including, but not limited to, bacterial, fungal, algal, and plant cells) and synthetic sources, such as chemical compound libraries or biological libraries such as antibody substance or peptide libraries. Agents are screened for the ability to either stimulate or inhibit the activity. Binding assays are used to detect receptor binding activity to ligands. Both functional and binding assays of receptor activity are readily adapted to screens for modulators such as agonist (stimulatory) and antagonist (inhibitory) compounds.

Contemplated herein are a multitude of assays to screen and identify modulators, such as agonists and antagonists, of ligand binding to receptors. In one example, the receptor is immobilized and interaction with a binding partner is assessed in the presence and absence of a candidate modulator. In another example, the binding partner is immobilized and the receptor is solubilized. In yet another example, interaction between the receptor and its binding partner is assessed in a solution assay, both in the presence and absence of a candidate modulator. An antagonist is identified as a compound that decreases binding between the receptor and its binding partner and/or decreases receptor signaling, while an agonist is identified as a compound that increases binding between the receptor and its binding partner and/or promotes receptor signaling. Another contemplated assay involves a variation of the di-hybrid assay wherein a modulator of protein/protein interactions is identified by detection of a positive signal in a transformed or transfected host cell.

Candidate modulators for screening according to contemplated by the invention include any chemical compounds, including libraries of chemical compounds. There are a number of different libraries used for the identification of small molecule modulators, including: (1) chemical libraries, (2) natural product libraries, and (3) combinatorial libraries comprised of random peptides, oligonucleotides or organic molecules. Chemical libraries consist of random chemical structures, or analogs of known compounds, or analogs of compounds that have been identified as "hits" or "leads" in prior drug discovery screens, some of which may be derived from natural products or from non-directed synthetic organic chemistry. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see Science 282:63-68 (1998). Combinatorial libraries are composed of large numbers of peptides, oligonucleotides, or organic compounds as a mixture. These libraries are relatively easy to prepare by traditional automated synthesis methods, PCR, cloning, or synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701-707 (1997). Identification of modulators through use of the various libraries described herein permits modification of the candidate "hit" (or "lead") to optimize the capacity of the "hit" to modulate activity.

Candidate modulators contemplated by the invention can be designed and include soluble forms of binding partners, as well as chimeric, or fusion, proteins thereof. A "binding partner" as used herein broadly encompasses non-peptide modulators, peptide modulators (e.g., neuropeptide variants), antibodies (including monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR and/or antigen-binding sequences, which specifically recognize a polypeptide of the invention), antibody fragments, and modified compounds comprising antibody domains that are immunospecific for the expression product of the identified GPCR-like gene.

A number of assays are known in the art that can identify chemical compounds that bind to or interact with a receptor. Such assays are useful, for example, in methods of identifying candidate modulators described herein, or in methods for identifying specific ligands of a receptor. Assays that measure binding or interaction of compounds with target proteins include assays that identify compounds that inhibit unfolding or denaturation of a target protein, assays that separate compounds that bind to target proteins through affinity ultrafiltration followed by ion spray mass spectroscopy/HPLC methods or other physical and analytical methods, capillary electrophoresis assays and two-hybrid assays.

One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method which distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al., Anal. Chem., 69:1683-1691 (1997), incorporated herein by reference. This technique screens combinatorial libraries of 20-30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Alternatively, such binding interactions are evaluated indirectly using the yeast two-hybrid system described in Fields et al., Nature, 340:245-246 (1989), and Fields et al., Trends in Genetics, 10:286-292 (1994), both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene.

a) Antibodies to Receptors as Modulators of Binding

Standard techniques are employed to generate polyclonal or monoclonal antibodies to receptors, and to generate useful antigen-binding fragments thereof or variants thereof. Such protocols can be found, for example, in Sambrook et al., Molecular Cloning: a Laboratory Manual. Second Edition, Cold Spring Harbor, N.Y.: Cold Spring Harbor Laboratory (1989); Harlow et al. (Eds), Antibodies A Laboratory Manual; Cold Spring Harbor Laboratory; Cold Spring Harbor, N.Y. (1988). In one embodiment, recombinant polypeptides (or cells or cell membranes containing such polypeptides) are used as antigens to generate the antibodies. In another embodiment, one or more peptides having amino acid sequences corresponding to an immunogenic portion of a receptor are used as antigen. Peptides corresponding to extracellular portions of receptors, especially hydrophilic extracellular portions, are preferred. The antigen may be mixed with an adjuvant or linked to a hapten to increase antibody production. Polyclonal and monoclonal antibodies, chimeric (e.g., humanized) antibodies, fragments of antibodies, and all other forms of antibody molecules disclosed herein are referred to collectively as antibody products.

(1) Polyclonal or Monoclonal Antibodies

As one exemplary protocol, a recombinant polypeptide or a synthetic fragment thereof is used to immunize a mouse for generation of monoclonal antibodies (or larger mammal, such as a rabbit, for polyclonal antibodies). To increase antigenicity, peptides are conjugated to Keyhole Lympet Hemocyanin (Pierce), according to the manufacturer's recommendations. For an initial injection, the antigen is emulsified with Freund's Complete Adjuvant and injected subcutaneously. At intervals of two to three weeks, additional aliquots of receptor antigen are emulsified with Freund's Incomplete Adjuvant and injected subcutaneously. Prior to the final booster injection, a serum sample is taken from the immunized mice and assayed by Western blot to confirm the presence of antibodies that immunoreact with a polypeptide. Serum from the immunized animals may be used as a polyclonal antisera or used to isolate polyclonal antibodies that recognize a receptor. Alternatively, the mice are sacrificed and their spleens are removed for generation of monoclonal antibodies.

One example of generating monoclonal antibodies follows: the spleens are placed in 10 ml serum-free RPMI 1640, and single-cell suspensions are formed by grinding the spleens in serum-free RPMI 1640, supplemented with 2 mM L-glutamine, 1 mM sodium pyruvate, 100 Units/ml penicillin, and 100 µg/ml streptomycin (RPMI) (Gibco, Canada). The cell suspensions are filtered and washed by centrifugation and resuspended in serum-free RPMI. Thymocytes taken from three naive Balb/c mice are prepared in a similar manner and used as a Feeder Layer. NS-1 myeloma cells, kept in log phase in RPMI with 10% (FBS (Hyclone Laboratories, Inc., Logan, Utah) for three days prior to fusion, are centrifuged and washed as well.

One example of producing hybridoma fusions follows: spleen cells from the immunized mice can be combined with NS-1 cells and centrifuged, and the supernatant is aspirated. The cell pellet is dislodged by tapping the tube, and 2 ml of 37° C. PEG 1500 (50% in 75 mM HEPES, pH 8.0) (Boehringer-Mannheim) is stirred into the pellet, followed by the addition of serum-free RPMI. Thereafter, the cells are centrifuged and resuspended in RPMI containing 15% FBS, 100 .mu.M sodium hypoxanthine, 0.4 µM aminopterin, 16 µM thymidine (HAT) (Gibco), 25 Units/ml IL-6 (Boehringer- Mannheim) and 1.5×106 thymocytes/ml and plated into 10 Corning flat-bottom 96-well tissue culture plates (Corning, Corning N.Y.).

On days 2, 4, and 6 after the fusion, 100 μl of medium is removed from the wells of the fusion plates and replaced with fresh medium. On day 8, the fusions are screened by ELISA, testing for the presence of mouse IgG that binds to a receptor polypeptide. Selected fusions are further cloned by dilution until monoclonal cultures producing anti-receptor antibodies are obtained.

(2) Receptor-Neutralizing Antibodies from Phage Display

Receptor-neutralizing antibodies are generated by phage display techniques such as those described in Aujame et al., Human Antibodies, 8(4):155-168 (1997); Hoogenboom, TIBTECH, 15:62-70 (1997); and Rader et al., Curr. Opin. Biotechnol., 8:503-508 (1997), all of which are incorporated by reference. For example, antibody variable regions in the form of Fab fragments or linked single chain Fv fragments are fused to the amino terminus of filamentous phage minor coat protein pIII. Expression of the fusion protein and incorporation thereof into the mature phage coat results in phage particles that present an antibody on their surface and contain the genetic material encoding the antibody. A phage library comprising such constructs is expressed in bacteria, and the library is screened for target-specific phage-antibodies using a labeled or immobilized target peptide or polypeptide as antigen-probe.

(3) Receptor-Neutralizing Antibodies from Transgenic Animals

Receptor-neutralizing antibodies are generated in transgenic animals, such as mice, essentially as described in Bruggemann et al., Immunol. Today 17(8):391-97 (1996) and Bruggemann et al., Curr. Opin. Biotechnol. 8:455-58 (1997). Transgenic mice carrying V-gene segments in germline configuration, and expressing the transgenes in their lymphoid tissue, are immunized with a polypeptide composition using conventional immunization protocols. Hybridomas are generated from B cells of the immunized mice using conventional protocols and screened to identify hybridomas secreting anti-receptor antibodies (e.g., as described above).

b) Assays to Identify Modulators of Receptor Activity

A number of approaches exist for the discovery of novel compounds that are binding partners for receptors. Each of the general approaches is compatible with high throughput screening (i.e., HTS) formats, which are preferred formats for identifying ligands and other binding partners of receptor polypeptides, such as modulators of receptor activity. The first approach involves measuring the binding of a known ligand, preferably labeled with a radiolabel, to a preparation that contains the receptor, either found in native tissue or based on expression of the gene encoding the receptor, typically in a heterologous system. The recombinant system involves the expression of a recombinant receptor. Another approach to the identification of receptor binding partners involves the measurement of the activity of the receptor, which may be influenced by either the binding of ligands that are agonists, and elevate receptor activity, or by the binding of antagonists, which interfere with agonist binding, thereby reducing the level of receptor activity. As for binding assays, recombinant systems are the presently preferred forms for function-based assays.

(1) Receptor Binding Assays (RBA) as High Throughput Screening (HTS) Systems for Drug Discovery The literature is replete with examples of the use of radiolabeled ligands in HTS binding assays for drug discovery (see Williams, Med. Res Rev. 11:147-184 (1991); Sweetnam et al., J. Nat. Prod. 56:441-455 (1993) herein incorporated by reference in their entirety for their teaching concerning high throughput screens). It is also possible to screen for novel neuroregeneration compounds with radiolabeled ligands in HTS binding screens. Other reasons that recombinant receptors are preferred for HTS binding assays include better specificity (higher relative purity) and ability to generate large amounts of receptor material (see Hodgson, Bio/Technology 10:973-980 (1992)).

A variety of heterologous systems are available for expression of recombinant receptors and are well known to those skilled in the art. Such systems include bacteria (Strosberg et al., Trends in Pharm. Sci. 13:95-98 (1992)), yeast (Pausch, Trends in Biotech. 15:487-494 (1997)), several kinds of insect cells (Vanden Broeck, Intl. Rev. Cytol. 164:189-268 (1996)), amphibian cells (Jayawickreme et al., Curr. Opin. Biotechnol. 8:629-634 (1997)) and several mammalian cell lines (CHO, HEK293, COS, etc.; see Gerhardt et al., Eur. J. Pharmacol. 334:1-23 (1997); Wilson et al., Brit. J. Pharmacol. 125:1387-1392 (1998)). These examples do not preclude the use of other possible cell expression systems, including cell lines obtained from nematodes (WO 98/37177).

A receptor expressed in one of the described recombinant systems can be used for HTS binding assays in conjunction with its defined ligand. The identified peptide is labeled with a suitable radioisotope, including, but not limited to $^{125}I$, $^{3}H$, $^{35}S$ or $^{32}P$, by methods that are well known to those skilled in the art. Alternatively, the peptides may be labeled by well-known methods with a suitable fluorescent label (Baindur et al., Drug Dev. Res. 33:373-398 (1994); Rogers, Drug Disc. Today 2:156-160 (1997)). Radioactive ligand specifically bound to the receptor in membrane preparations made from cells expressing the recombinant protein can be detected in HTS assays in one of several standard ways, including filtration of the receptor-ligand complex to separate bound ligand from unbound ligand (Williams, 1991; Sweetnam et al., 1993). Alternative methods include a scintillation proximity assay (SPA) or a FlashPlate format in which such separation is unnecessary (Nakayama et al., Drug Disc. & Dev. 1:85-91 (1998); Boss et al., J. Biomol. Screening 3:285-292 (1998)). Binding of fluorescent ligands can be detected in various ways, including fluorescence energy transfer (FRET), direct spectrophotofluorometric analysis of bound ligand, or fluorescence polarization (see Rogers, 1997; Hill, Curr. Opin. Drug Disc. & Dev. 1:92-97 (1998)).

(2) Response-Based Receptor HTS Systems

Activation of $GABA_A$ receptors or subunits thereof expressed in recombinant systems results in a variety of biological responses, which are typically mediated by proteins expressed in the host cells. The proteins required for functional expression of $GABA_A$ receptor subunits can be native constituents of the host cell or can be introduced through well-known recombinant technology. They can be mutants of native varieties as well. The proteins can be intact or chimeric.

Fluorescence changes can also be used to monitor ligand-induced changes in membrane potential or intracellular pH; an automated system suitable for HTS has been described for these purposes (Schroeder et al., J. Biomol. Screening 1:75-

80 (1996)). Among the modulators that can be identified by these assays are natural ligand compounds of the receptor; synthetic analogs and derivatives of natural ligands; antibodies, antibody fragments, and/or antibody-like compounds derived from natural antibodies or from antibody-like combinatorial libraries; and/or synthetic compounds identified by high throughput screening of libraries; and other libraries known in the art. All modulators that bind $GABA_A$ receptors are useful for identifying $GABA_A$-like polypeptides in tissue samples (e.g., for diagnostic purposes, pathological purposes, and other purposes known in the art). Agonist and antagonist modulators are useful for up-regulating and down-regulating $GABA_A$ receptor activity, respectively, for purposes described herein. $GABA_A$ receptor binding partners also may be used to deliver a therapeutic compound or a label to cells that express a $GABA_A$ receptor or a subunit thereof (e.g., by attaching the compound or label to the binding partner).

The assays may be performed using single putative modulators; they may also be performed using a known agonist in combination with candidate antagonists (or visa versa). Detectable molecules that may be used include, but are not limited to, molecules that are detectable by spectroscopic, photochemical, biochemical, immunochemical, electrical, radioactive, and optical means, including but not limited to bioluminescence, phosphorescence, and fluorescence. These detectable molecules should be a biologically compatible molecule and should not compromise the biological function of the molecule and must not compromise the ability of the detectable molecule to be detected. Preferred detectable molecules are optically detectable molecules, including optically detectable proteins, such that they may be excited chemically, mechanically, electrically, or radioactively to emit fluorescence, phosphorescence, or bioluminescence. More preferred detectable molecules are inherently fluorescent molecules, such as fluorescent proteins, including, for example, Green Fluorescent Protein (GFP). The detectable molecule may be conjugated to the GRK protein by methods as described in Barak et al. (U.S. Pat. Nos. 5,891,646 and 6,110,693). The detectable molecule may be conjugated at the front-end, at the back-end, or in the middle.

The cells of the present invention may express at least one $GABA_A$ receptor or a subunit thereof, wherein at least one of the molecules is detectably labeled. Cells useful in the present invention include eukaryotic and prokaryotic cells, including, but not limited to, bacterial cells, yeast cells, fungal cells, insect cells, nematode cells, plant cells, and animal cells. Suitable animal cells include, but are not limited to, HEK cells, HeLa cells, COS cells, and various primary mammalian cells. An animal model expressing a $GABA_A$ receptor and a detectable molecule throughout its tissues or within a particular organ or tissue type, may also be used.

(3) Luciferase Reporter Gene Assay

The photoprotein luciferase provides another useful tool for assaying for modulators of $GABA_A$ receptor activity. Cells (e.g., CHO cells or COS 7 cells) are transiently co-transfected with both a GABAA receptor expression construct (e.g., a GABAA receptor in pzeoSV2 (Invitrogen, San Diego, Calif.)) and a reporter construct which includes a luciferase coding region downstream from a transcription factor. Expression levels of luciferase reflect the activation status of the signaling events. [See generally George et al., Journal of Biomolecular Screening, 2(4): 235-40 (1997); and Stratowa et al., Curr. Opin. Biotechnology, 6: 574-81 (1995).] Luciferase activity may be quantitatively measured using, e.g., luciferase assay reagents that are commercially available from Promega (Madison, Wis.).

c) Nucleic Acid Detection

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2.mu. plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast a-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, plant cells, nematode cells, and animal cells, such as HEK-293, CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

E. Methods of Making the Compositions

The compositions disclosed herein and the compositions necessary to perform the disclosed methods can be made using any method known to those of skill in the art for that particular reagent or compound unless otherwise specifically noted. It is understood that general molecular biology techniques, such as those disclosed in Sambrook et al., *Molecular Cloning: A Laboratory Manual*, 2nd Edition (Cold Spring Harbor Laboratory Press, Cold Spring Harbor, N.Y., 1989) are available for making the disclosed molecules and practicing the disclosed methods unless otherwise noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al.,

*Molecular Cloning: A Laboratory Manual,* 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System IPlus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., Methods Enzymol., 65:610-620 (1980), (phosphotriester method). (Peptide nucleic acid molecules) can be made using known methods such as those described by Nielsen et al., *Bioconjug. Chem.* 5:3-7 (1994).

2. Peptide Synthesis

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxy-carbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a protein, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269: 16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

3. Combinatorial Chemistry

The disclosed $GABA_A$ receptors, and mutations thereof, can be used as targets for any combinatorial technique to identify molecules or macromolecular molecules that interact with the disclosed compositions in a desired way. Also disclosed are the compositions that are identified through combinatorial techniques or screening techniques in which the receptors disclosed in SEQ ID NOS: 1 and 3, as well as the other $GABA_A$ receptors disclosed herein, or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed $GABA_A$ receptors are also disclosed.

It is understood that the disclosed methods for identifying molecules that modulate $GABA_A$ receptors and agonists/antagonists thereof, can be performed using high through put means. For example, putative inhibitors can be identified using Fluorescence Resonance Energy Transfer (FRET) to quickly identify interactions. The underlying theory of the techniques is that when two molecules are close in space, ie, interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptdyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23) 12997-302 (1997)).

Another preferred method for combinatorial methods designed to isolate peptides is described in Cohen et al. (Cohen B. A.,et al., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain.

Using methodology well known to those of skill in the art, in combination with various combinatorial libraries, one can isolate and characterize those small molecules or macromolecules, which bind to or interact with the desired target, such as the $GABA_A$ receptors. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449, 754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916, 899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856, 107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in iterative processes.

a) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as drugs that interact with $GABA_A$ receptors, are also disclosed. Thus, the products produced using the molecular modeling approaches that involve the disclosed compositions are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 Acta Pharmaceutica Fennica 97, 159-166; Ripka, New Scientist 54-57 (Jun. 16, 1988); McKinaly and Rossmann, 1989 Annu. Rev. Pharmacol. Toxiciol. 29, 111-122; Perry and Davies, QSAR: Quantitative Structure-Activity Relationships in Drug Design pp. 189-193 (Alan R. Liss, Inc. 1989); Lewis and Dean, 1989 Proc. R. Soc. Lond. 236, 125-140 and 141-162; and, with respect to a model enzyme for nucleic acid components, Askew, et al., 1989 J. Am. Chem. Soc. 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Residues in the First Transmembrane Domain of the C. elegans $GABA_A$ Receptor Confer Sensitivity to the Neurosteroid Pregnenolone Sulfate a) Methods Sequence analysis and modeling: To identify conserved residues for mutagenesis, the following cysteine loop receptor subunits were aligned: Rat $GABA_A$ receptor subunits $\alpha 1$ (SwissProt: p18504), $\alpha 2$ (SwissProt: p23576), $\alpha 3$ (SwissProt: p20236), $\alpha 4$ (SwissProt: p28471), $\alpha 5$ (SwissProt: p19969), $\alpha 6$ (SwissProt: p30191), $\beta 1$ (SwissProt: p15431), $\beta 2$ (SwissProt: p15432), $\beta 3$ (SwissProt: p15433), $\gamma 1$ (SwissProt: p23574), $\gamma 2$ (SwissProt: p18508), $\gamma 3$ (SwissProt: p28473), $\delta$ (SwissProt: p18506); Rat $GABA_C$ receptor subunits $\rho 1$ (SwissProt: p50572), $\rho 2$ (SwissProt: p47742), $\rho 3$ (SwissProt: p50573); Rat glycine receptor subunits $\alpha 1$ (SwissProt: p07727), $\alpha 2$ (SwissProt: p22771), $\alpha 3$ (SwissProt: p24524), $\beta$ (SwissProt: p20781); Human $GABA_A$ receptor $\epsilon$ subunit (gb:U66661), Drosophila melanogaster rdl gene product (SwissProt: p25123), Drosophila GABA receptor $\beta$ subunit (SwissProt: q08832); lymnaea stagnalis GABA receptor $\beta$ subunit (SwissProt: p26714); and avermectin-sensitive glutamate-gated chloride channel $\alpha 1$ subunit (pir2: s50864), $\beta$ subunit (gb:u14525). Alignment was performed using the Pileup program in the GCG computer sequence analysis package.

Homology models were built using ModellerV6.2 (Sali & Blundell, 1993) based on the 4 Å structure of the nicotinic acetylcholine receptor transmembrane domains (Miyazawa et al., 2003). The following subunits were aligned to generate this model: Torpedo marmorata nicotinic acetylcholine receptor subunits $\alpha$ (1OEDA), $\beta$ (1OEDB), $\delta$ (1OEDC), $\gamma$ (1OEDE); mouse nicotinic acetylcholine receptor $\alpha 1$ subunit (P04756); UNC-49B (AAD42383), rat $GABA_A$ receptor subunits $\alpha 1$ (P18504), $\alpha 2$ (P23576), $\alpha 3$ (P20236), $\alpha 4$ (P28471), $\beta 1$ (P15431), $\beta 2$ (P15432), $\beta 3$ (P15433), $\gamma 1$ (P23574), $\gamma 2$ (P18508), $\gamma 3$ (P28473), rat $GABA_C$ receptor subunits $\rho 1$ (P50572), $\rho 2$ (P47742), $\rho 3$ (P50573); rat glycine receptor subunits $\alpha 1$ (P07727), $\alpha 2$ (P22771), $\alpha 3$ (P24524), $\beta$ (P20781); human $GABA_A$ receptors $\alpha 5$ (CAA01920), $\alpha 6$ (NP000802), Drosophila melanogaster Rdl gene product (P25123). Membrane-spanning residues were aligned, the large intracellular loop between M3 and M4 was omitted. Alignments were performed with ClustalW software (Thompson et al., 1994).

Site-directed mutagenesis: Chimeric and mutant receptors were constructed using standard molecular biology techniques. Construction of chimeras and site-directed mutagenesis were performed using a PCR-based method. Briefly, mutations were introduced into the sequences of oligonucleotide primers used for polymerase chain reaction (PCR). The resulting PCR products were then cloned into either a wild-type or mutagenized UNC-49B plasmid to generate the desired combination of mutations and chimeric segments. Silent restriction sites were often introduced at convenient locations, also using the PCR-based mutagenesis procedure, to facilitate plasmid construction. For each new molecule, the region corresponding to the mutagenized PCR fragment, and its junctions with the vector molecule, were sequenced prior to use.

Electrophysiology: Plasmids containing wild-type and mutagenized $GABA_A$ receptor subunits were linearized and transcribed in vitro using T3 RNA polymerase (mMessage mMachine T3 kit, Ambion, Austin Tex.). UNC-49B mRNA was injected into *Xenopus laevis* oocytes at 0.5 µg/µl either alone, or in a mixture with 0.5 µg/µl UNC-49C. All other *C. elegans* subunits were injected at 1.0 µg/µl except for the TM chimera, which produced very small currents and was injected at concentrations up to 6.0 µg/µl. The injection volume ranged between 27.6 nl to 50.6 nl. Oocytes were analyzed using two electrode voltage-clamp electrophysiology using a GeneClamp 500 Amplifier (Axon Instruments, Foster City Calif.), as previously described (Bamber et al., 2003). Cells were voltage clamped at −60 mV. All recordings were performed at room temperature.

$GABA$ $EC_{50}$ concentrations were determined by performing GABA dose-response curves, and fitting them with the equation:

$$I = I_{max} / \{1 + 10^{(\log EC_{50} - [agonist]) * n}\}$$

where I is current at a given GABA concentration, $I_{max}$ is current at saturation, $EC_{50}$ is the GABA concentration required to produce half-maximal current, and n is the slope coefficient. GABA dose-response curves were fit using GraphPad Prism software (San Diego). PS inhibition was measured at the GABA $EC_{50}$ concentration for all receptors, with the exception of the M1-M2 chimera and the M1-M2-linker chimera. These molecules expressed very inefficiently, producing no current in most cells, and only small currents in others. First, it was difficult to obtain enough expressing cells to accurately determine GABA $EC_{50}$ values. Second, it was necessary to use high GABA concentrations to obtain currents large enough to measure PS inhibition (1000 µM for the M1-M2 chimera and 100 µM for the M1-M2-linker chimera). For UNC-49B homomers and UNC-49B/C heteromers, GABA $EC_{50}$ values are highly variable (Barnber et al., 2003). $EC_{50}$ values presented in Table 1 for these two receptors reflect a single batch of oocytes that was used to measure the PS $IC_{50}$.

Figure 1A:
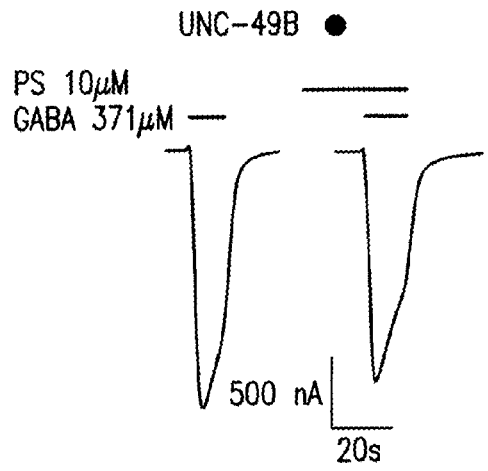
Figure 1B:
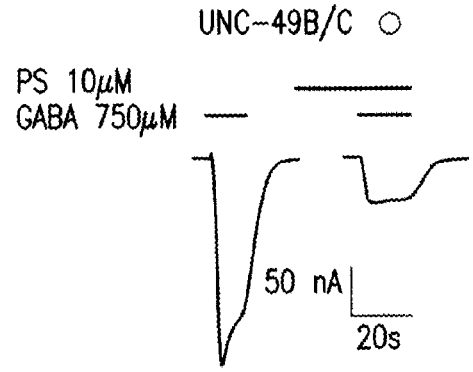
Figure 1C:
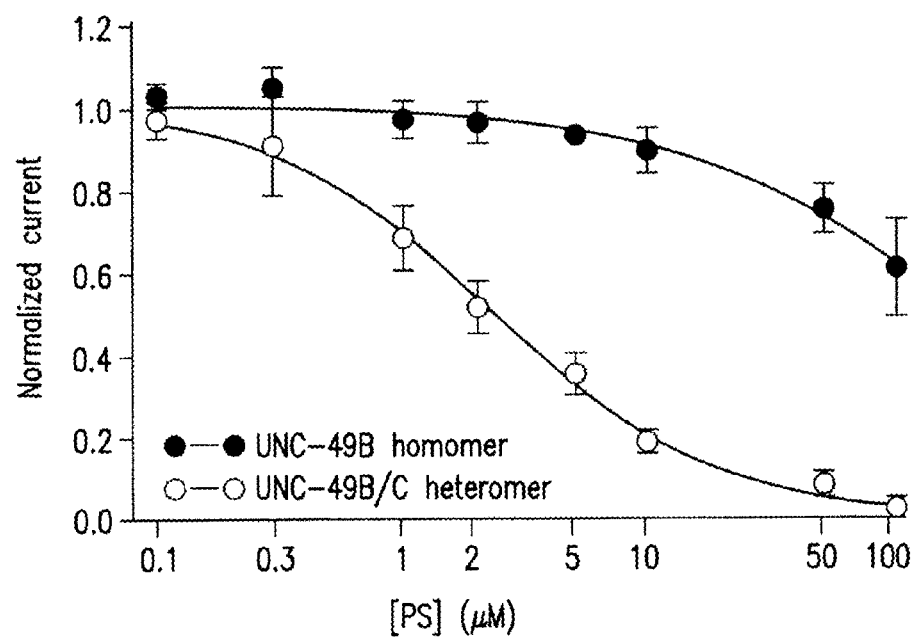

PS inhibition was measured by applying PS for 20 seconds, and then co-applying PS and GABA. Ten-second and 20-second PS pre-applications produced the same amount of inhibition, showing that the amount of PS bound to the receptor was no longer changing at the time that GABA was applied. Generally, PS evoked little or no direct response. For most constructs, PS pre-application resulted in changes in the holding current corresponding to less than 5% of $EC_{50}$ GABA-evoked currents (upward or downward deflection, depending on the molecule), and only at the highest PS concentrations (30 and 100 µM). The T257F and T257F/S264A point mutants and the XY chimera were exceptions: application of 100 µM PS caused a reduction of the holding current (opposite to the effect of GABA) that was 6-20% as large as the $EC_{50}$ GABA-evoked current for the T257F and T257F/S264A point mutants, and equal in amplitude to the $EC_{50}$ GABA-evoked current for the XY chimera. Interestingly, picrotoxin did not depress these holding currents, showing that PS and picrotoxin can modulate different classes of open states. Where PS direct effects were observed, GABA-evoked peak currents were measured from the baseline in the presence of PS rather than the baseline prior to PS application. This correction resulted in PS $IC_{50}$ values that were 44% higher for T257F, and 18% higher for T257F/S264A, but not significantly different for the XY chimera. Picrotoxin inhibition of GABA evoked currents was measured by co-application of GABA and picrotoxin. It was routinely verified that currents recovered to their original magnitudes once the inhibitors had been removed. Currents reported in this study are the peak currents observed upon GABA application. PS and picrotoxin dose-response curves were fitted using the equation:

$$I_{inh+}/I_{inh-} = 1/\{([inh]/IC_{50})^n + 1\}$$

where $I_{inh+}/I_{inh-}$ is the current in the presence of inhibitor (PS or picrotoxin) relative to GABA alone, $IC_{50}$ is the concentration of inhibitor required to block 50% of the current, and n is the slope coefficient. PS dose-response curves were fit using GraphPad Prism or NFIT (Island Products, Galveston Tex.; FIG. 1C UNC-49B/C curve only). Biphasic dose-response curves (FIG. 5) were fit with the equation:

$$I = [1 + A/(1 + (EC_{50}/[PS])^{nE})] * [1/(([PS]/IC_{50})^{nI} + 1)]$$

where I is normalized current, A is the amplitude of I above 1, $EC_{50}$ and $IC_{50}$ are respectively the half maximal enhancing and inhibitory concentrations of PS, nE and nI are respectively the slope coefficients for the enhancement and inhibition. Biphasic PS dose-response curves were fit with MATLAB (The MathWorks, Natick Mass.), using custom-written routines (M. Jones, University of Wisconsin, Madison Wis.). Confidence limits were estimated using a bootstrapping approach with 1000 trials (Jones et al., 2001). These trials generated the following median parameter values and interquartile ranges (IQR): For the M258L mutant, A=1.56 (IQR=1.0-5.4), $EC_{50}$=3.95 µM (IQR=2.0-16.8), nE=1.0 (IQR=0.7-1.1), $IC_{50}$=45.3 µM (IQR=25.0-57.0), and nI=1.8 (IQR=1.5-2.1). For the M258L/S264A mutant, A=1.0 (IQR=0.6-3.2), $EC_{50}$=2.4 µM (IQR=1.3-8.6), nE=1.3 (IQR=0.9-1.9), $IC_{50}$=52.6 µM (IQR=25.0-71.0), and nI=1.9 (IQR=1.4-2.6). Error bars in the figures are standard error of the mean. All drugs were obtained from Sigma (St. Louis). GABA was prepared as a 1M stock in water, and stored at −20° C. for up to one year. PS was prepared as 10 mM stocks in dimethyl sulfoxide (DMSO). The final DMSO concentration was 1% at the maximal PS concentrations tested, and we verified that this concentration of DMSO did not inhibit or enhance GABA-evoked currents. Picrotoxin was prepared as a 100 mM stock in DMSO.

b) Results

Figures 1, 23A:
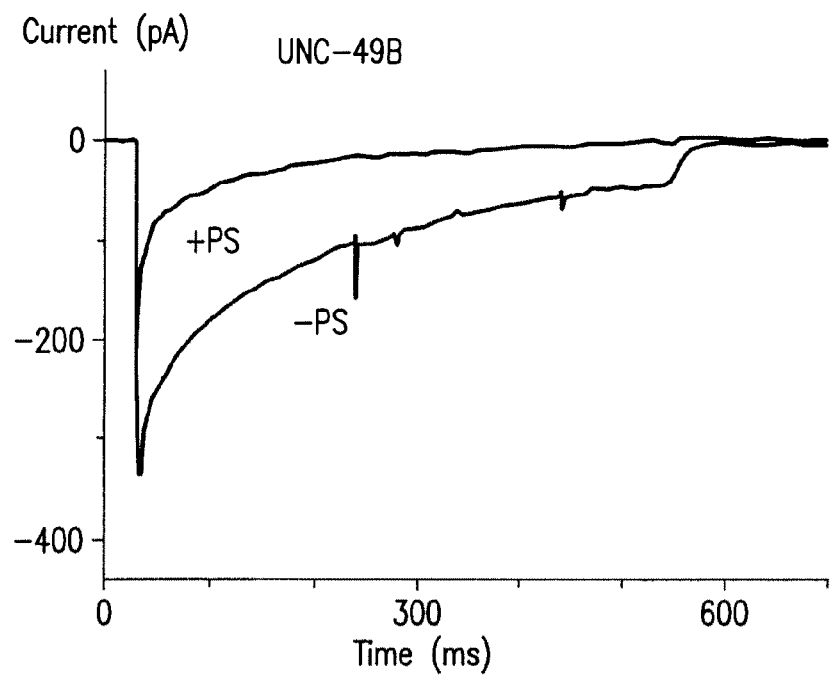
Figures 2, 23A:
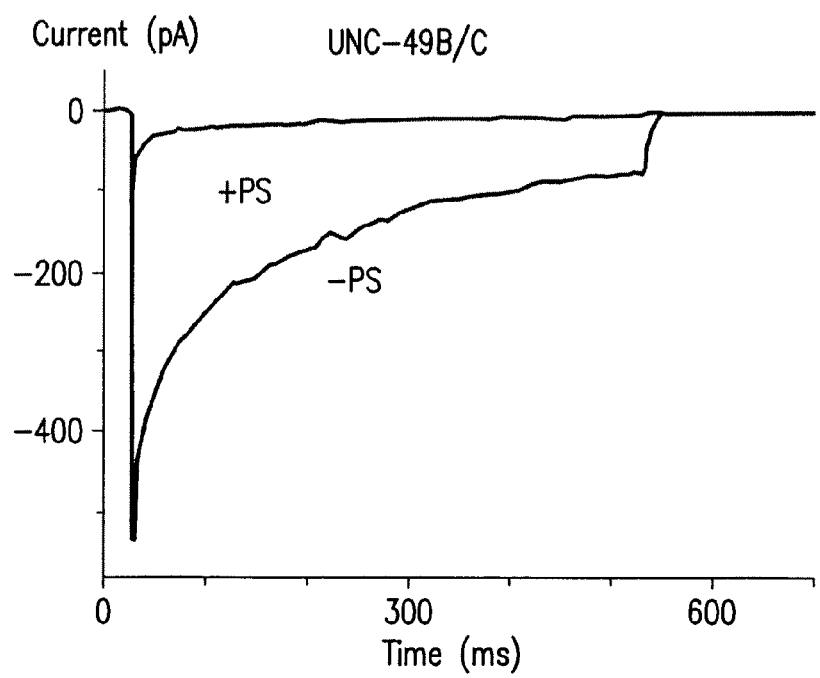
Figures 1, 23B:
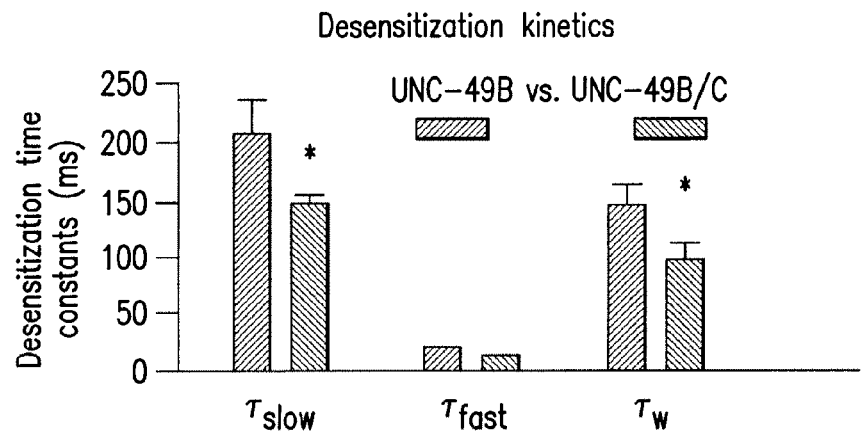
Figures 2, 23B:
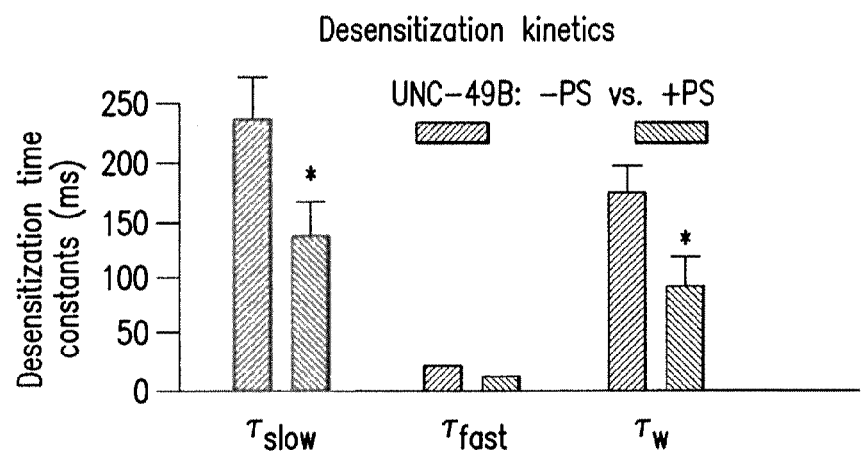
Figures 3, 23B:
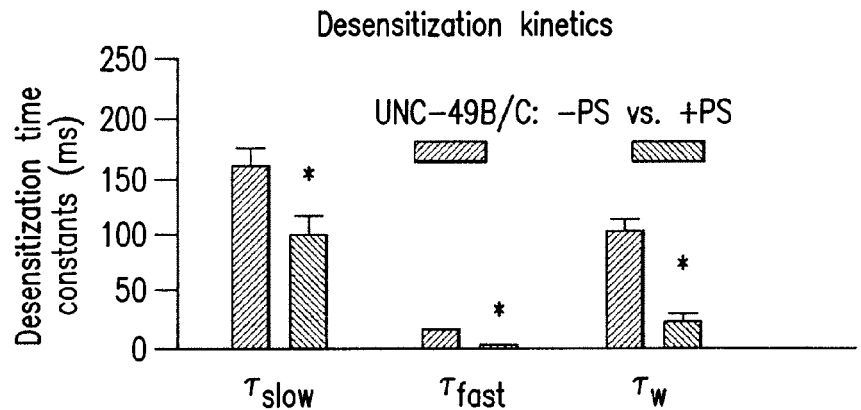

The UNC-49C subunit confers increased pregnenolone sulfate sensitivity. The UNC-49B/C heteromer is significantly more sensitive to PS inhibition than the UNC-49B homomer (FIG. 1, Table 1). UNC-49B/C heteromeric receptors were inhibited by 95% at 100 µM PS, and the PS concentration that produced half-maximal inhibition ($IC_{50}$) was 2.3 µM. This value is very similar to inhibition observed for mammalian $GABA_A$ receptors which is also in the low micromolar range (Majewska, 1992; Nilsson et al., 1998; Park-Chung et al., 1999; Shen et al., 1999). By contrast, the UNC-49B homomer displayed only modest inhibition (40%) at 100 µM PS. By extrapolating the PS dose-response curve, it is estimated that the PS $IC_{50}$ for UNC-49B homomers is 191 µM.

One interpretation of this differential PS sensitivity is that UNC-49C contributes residues which bind PS with higher affinity, or transduce PS binding into channel inhibition more efficiently than their UNC-49B counterparts. A three step approach was used to identify these UNC-49C residues: first, chimeric subunits were constructed to identify the regions of UNC-49C which contain the critical residues; second, residues were identified in these regions which were conserved with other neurosteroid-sensitive subunits that played a role in PS sensitivity; and third, systematic mutagenesis to identify the remaining contributors to PS sensitivity was performed.

Figure 2A:
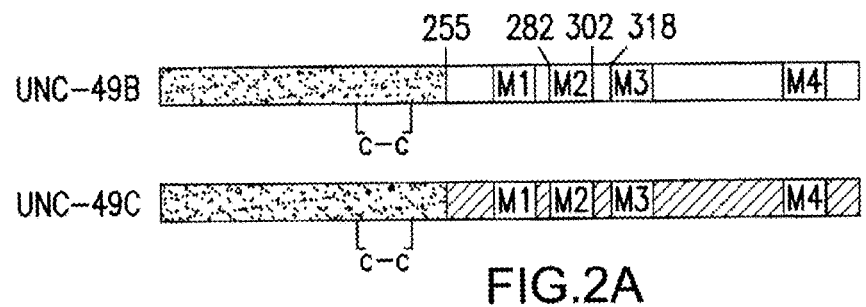

Domains required for PS inhibition: The increased PS sensitivity of the UNC-49C-containing receptor showed that domains important for PS inhibition can be identified using a chimera approach. A series of chimeric subunits containing UNC-49B and UNC-49C sequences were constructed. UNC-49B and UNC-49C were generated by alternative splicing of a single gene (unc-49) that contains a shared amino terminus and three alternative carboxy termini (Bamber et al., 1999). The common amino terminus is 188 amino acids long, and includes some of the residues which form the GABA binding site (binding segments A, D, and E; Lester et al., 2004). The divergent regions encompass the remaining residues of the GABA binding site (binding segments B, C, and F; Lester et al., 2004), and all four transmembrane domains (FIG. 2a). The following chimera experiments demonstrate that important determinants of PS inhibition are located in the M1 domain and in the linker joining M2 and M3.

Figure 2B:
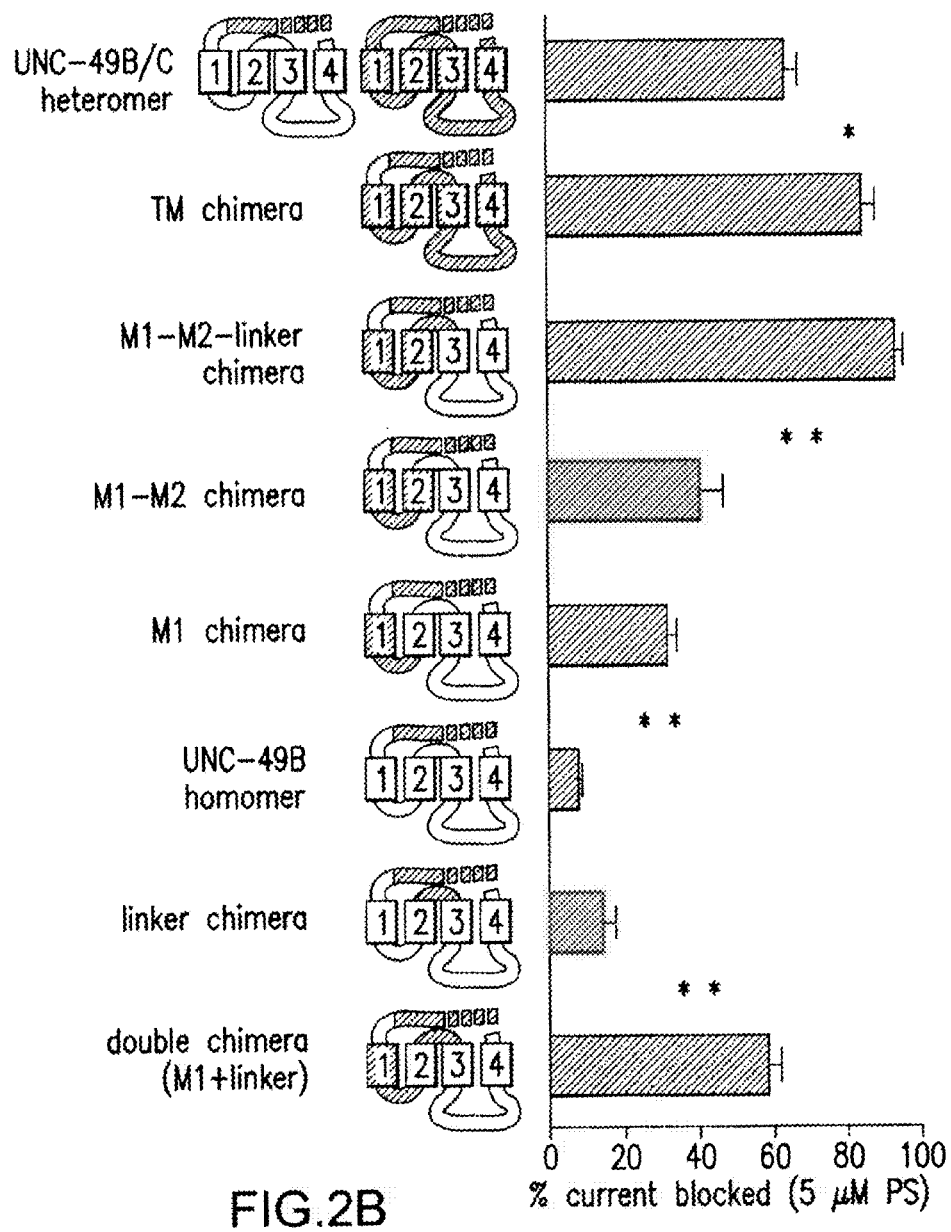
Figure 2C:
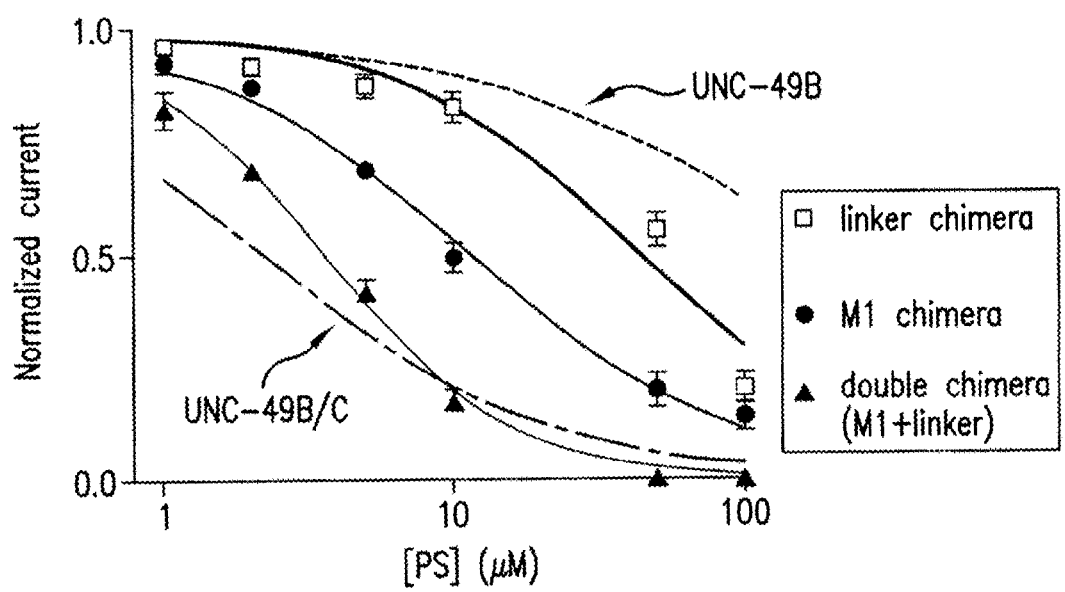
Figure 2D:
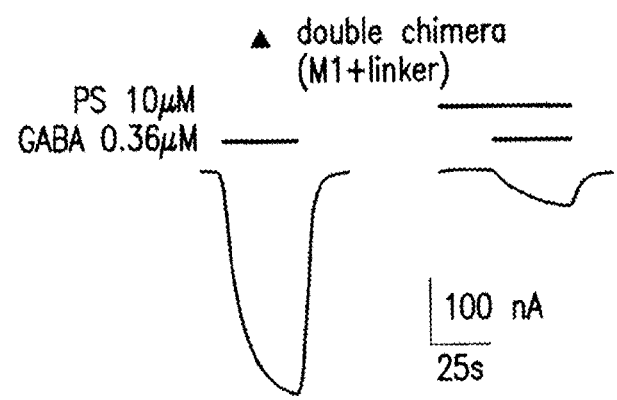

The entire transmembrane domain region of UNC-49C was first tested. A chimera that contained the entire extracellular domain derived from UNC-49B, and transmembrane domain sequences derived from UNC-49C (the 'TM' chimera) was constructed. The TM chimera formed a functional homomer that was strongly inhibited by 5 µM PS (FIG. 2b, Table 1). This result is significant for two reasons. First, it demonstrates that important residues for PS inhibition are located within the transmembrane domain region of UNC-49C. Second, it demonstrates that the UNC-49C PS site can function in a homomultimeric configuration. This property simplifies further analysis: mutational analysis in heteromultimers is complicated by the possibility that mutations can alter subunit stoichiometry, rather than simply PS interactions. From this point forward, all chimeric and mutant subunits were analyzed as homomultimers.

To narrow the UNC-49C residues that are necessary for increased PS sensitivity, progressively smaller stretches of the UNC-49C transmembrane domain region were tested. The strategy represents a deletion of UNC-49C material from the carboxy to amino terminal end of the transmembrane portion of the subunit, which is then replaced with UNC-49B sequences. First the M1 through the M2-M3 linker of UNC-49C were tested for PS sensitivity (FIG. 2b, 'M1-M2-linker' chimera). This chimera was equally sensitive to 5 µM PS as the TM chimera, indicating that UNC-49C residues from the beginning of M3 to the C terminus were dispensible for high PS sensitivity. By contrast, a chimera including only the first two transmembrane regions of UNC-49C ('M1-M2' chimera) was significantly less PS sensitive, indicating that the UNC-49C M2-M3 linker was necessary for high PS sensitivity. A chimera composed of the first transmembrane domain (the 'M1' chimera) did not have further reduced PS sensitivity, showing that UNC-49C M2 domain was not necessary for PS sensitivity. However, the M1 chimera was significantly more PS sensitive than the wild-type UNC-49B receptor, indicating a role for the UNC-49C M1 residues. These data show that two regions are required for PS sensitivity: the M2-M3 linker domain and the M1 transmembrane domain.

It was then demonstrated that the M1 and M2-M3 linker domains together are sufficient for full PS sensitivity. A construct containing both domains was compared to constructs containing just one of these domains (FIG. 2b, c). PS sensitivity was assessed in this and all subsequent experiments by generating PS dose-response curves and comparing $IC_{50}$ values. The UNC-49C M2-M3 linker alone (the 'linker' chimera) modestly increased PS sensitivity. The UNC-49C M1 domain alone increased PS sensitivity to a greater degree, but was still insufficient to increase PS sensitivity to the same level as the UNC-49B/C heteromer. However when substituted together (the 'double' chimera), these two domains conferred PS sensitivity that was only slightly less than the UNC-49B/C heteromer. Therefore, residues in the M1 domain and the M2-M3 extracellular linker are sufficient to account for nearly all of the PS sensitivity of UNC-49C.

Figure 3B:
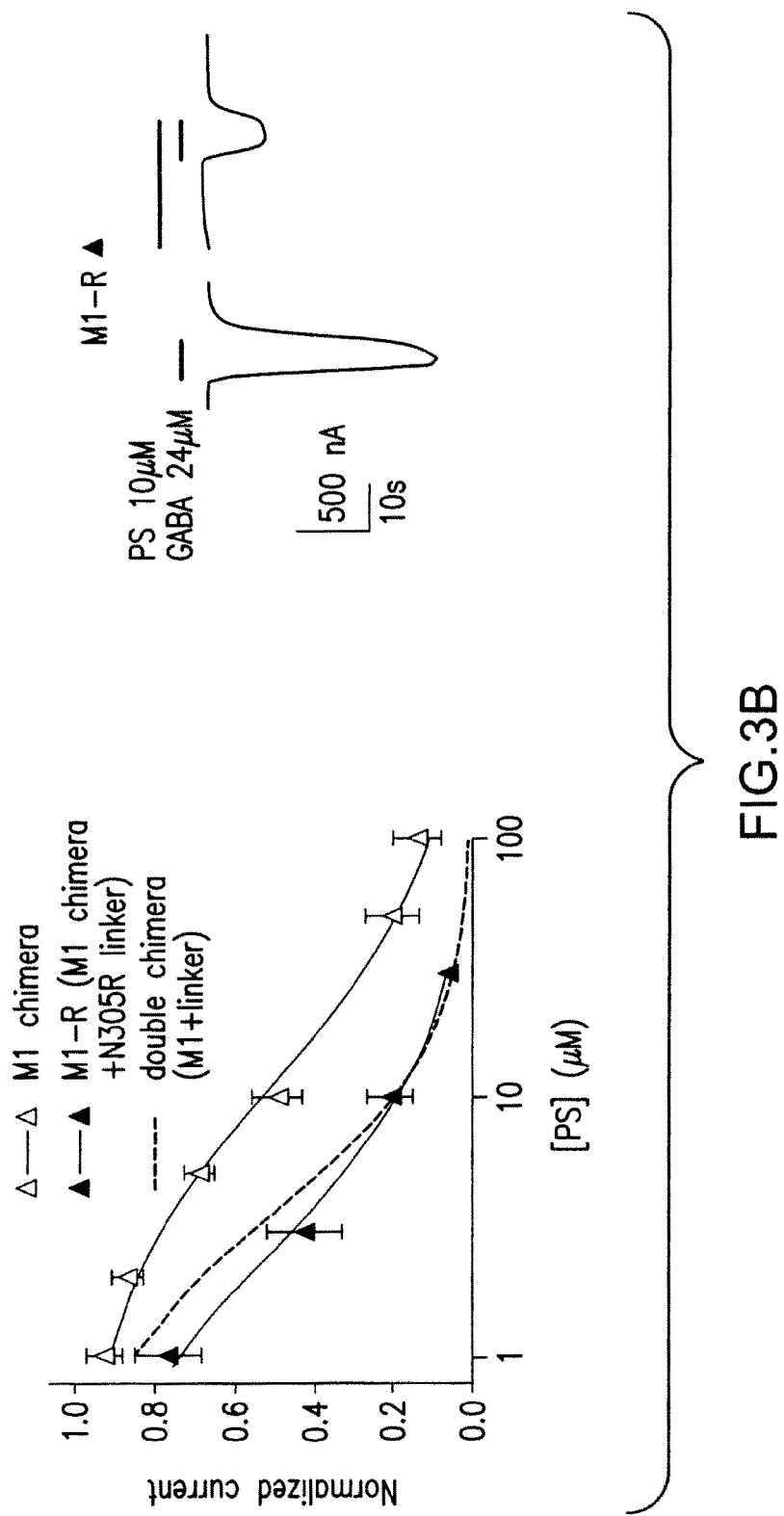

Conserved M1 and M2-3 linker residues contribute to PS sensitivity. Which residues in these regions are responsible for PS sensitivity? In the second step, amino acids were identified in these regions that were conserved among neurosteroid-sensitive $GABA_A$ receptors and UNC-49C but differed in UNC-49B (FIG. 3a). Within the M2-M3 linker, most residues are conserved among all GABA receptor subunits. However, mammalian $GABA_A$ receptor subunits and UNC-49C contain one or two positively-charged residues at the extracellular end of the pore-forming M2 helix (FIG. 3a). By contrast, UNC-49B contains only neutral residues in this region (N304, N305, S306). To test the function of residues in the M2-M3 linker, asparagine 305 was mutated to arginine in the M1 chimera to create the 'M1-R' subunit, and compared it to the double chimera containing both the M1 and linker regions (FIG. 3b). The N305R mutation increases the PS sensitivity to the same level as in the double chimera (FIG. 3b, Table 3). Therefore it was concluded that a single positively-charged residue is sufficient to account for the ability of the UNC-49C M2-3 linker to confer heightened PS sensitivity.

Figure 3C:
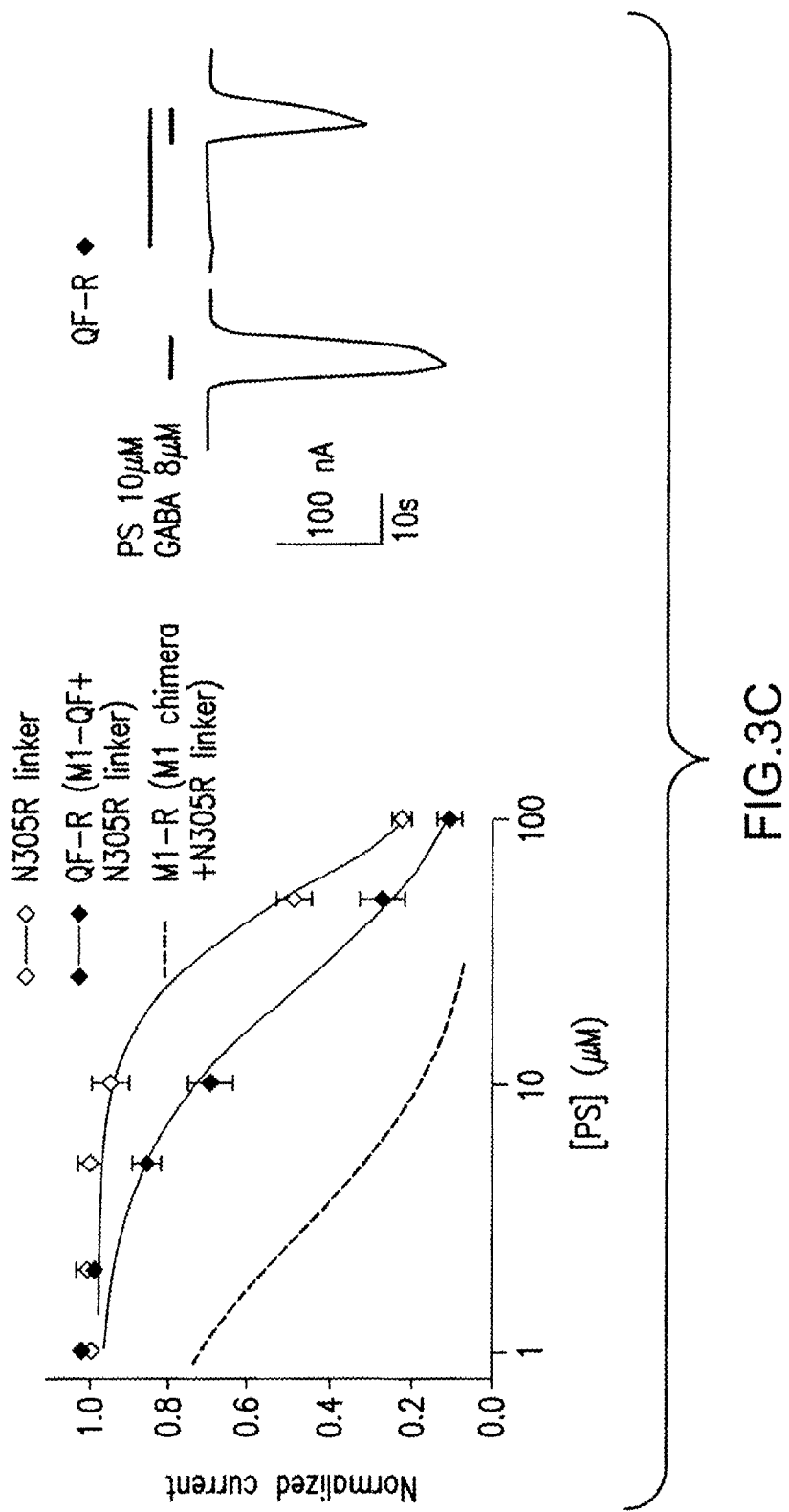

The conserved residues were tested in the UNC-49C M1 domain in a similar way. Two residues in the M1 domain are conserved among the mammalian GABA receptor subunits and UNC-49C but differ from UNC-49B. Specifically, residues 259 and 261 are glutamine and an aromatic residue, respectively, in the PS-sensitive subunits, but these residues are asparagine and valine in the UNC-49B M1 domain. To test the importance of these conserved residues, they were substituted into an UNC-49B subunit with the linker mutation N305R to create the 'QF-R' subunit (FIG. 3c). This receptor is 2.1-fold more sensitive to PS than N305R, but it is still 6.7-fold less sensitive than the double chimera (FIG. 3c, Table 2). It was concluded that residues 259 and 261 are important but that other residues in M1 also play a role.

TABLE 2

| | VII. Subunit PS GABA | | | |
|---|---|---|---|---|
| | $IC_{50}$ (µM) | Slope coefficient | $EC_{50}$ (µM) | Slope coefficient |
| UNC-49B | 191 | 0.7 | 371 ± 61 (n = 4) | 2.0 ± 0.1 (n = 4) |
| UNC-49B/C | 2.3 ± 0.2 (n = 4) | 0.9 ± 0.1 (n = 4) | 750 ± 31 (n = 4) | 1.3 ± 0.1 (n = 4) |
| TM chimera | n/d | n/d | 119.7 ± 17.8 (n = 5) | 1.1 ± 0.1 (n = 5) |
| M1-M2-linker chimera | n/d | n/d | 20.3 (n = 2) | 0.7 (n = 2) |
| M1-M2 chimera | n/d | n/d | >300 (n = 2) | n/d |

TABLE 2-continued

VII. Subunit PS GABA

| | $IC_{50}$ (μM) | Slope coefficient | $EC_{50}$ (μM) | Slope coefficient |
|---|---|---|---|---|
| M1 chimera | 11.9 ± 2.0 (n = 4)[1,2] | 0.9 ± 0.1 (n = 4) | 290 ± 48 (n = 5) | 1.7 ± 0.1 (n = 5) |
| linker chimera | 44.9 ± 7.0 (n = 5)[1,2] | 1.3 ± 0.2 (n = 5) | 9.7 ± 1.5 (n = 5) | 2.0 ± 0.2 (n = 5) |
| double chimera (M1 + linker) | 3.6 ± 0.3 (n = 4)[3] | 1.4 ± 0.1 (n = 4) | 0.36 ± 0.1 (n = 5) | 1.0 ± 0.1 (n = 5) |
| M1-R | 2.8 ± 0.4 (n = 8)[4] | 1.2 ± 0.1 (n = 8) | 24.2 ± 2.0 (n = 11) | 1.9 ± 0.2 (n = 11) |
| N305R | 51.0 ± 4.5 (n = 4)[5] | 1.9 ± 0.2 (n = 4) | 4.0 ± 0.5 (n = 7) | 2.0 ± 0.2 (n = 7) |
| QF-R | 24.7 ± 4.7 (n = 6)[2,6] | 1.5 ± 0.5 (n = 6) | 8.0 ± 1.8 (n = 10) | 1.8 ± 0.1 (n = 10) |

[1]Significantly different from UNC-49B/C (P < 0.05, Mann-Whitney U test)
[2]Significantly different from double chimera (P < 0.05, Mann-Whitney U test)
[3]Significantly different from UNC-49B/C (P < 0.05, Student's T test)
[4]Not different from double chimera (P > 0.05, Student's T test)
[5]Not different from linker chimera (P > 0.05, Student's T test)
[6]Significantly different from N305R mutant (P < 0.05, Student's T test)

Figure 4A:
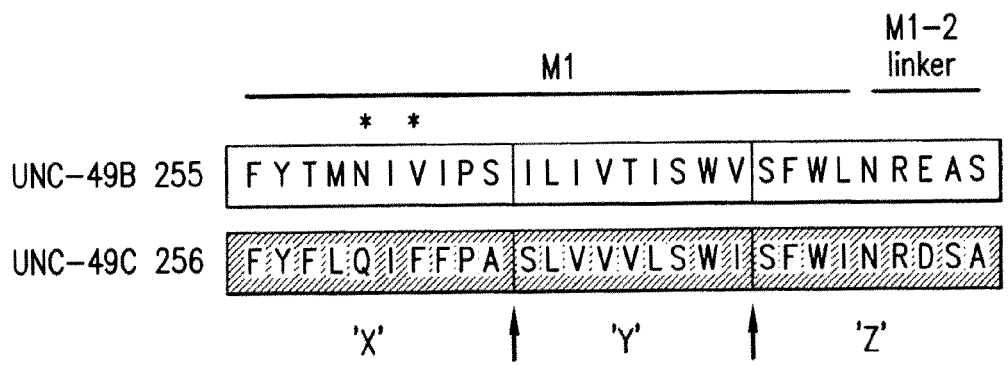
Figure 4B:
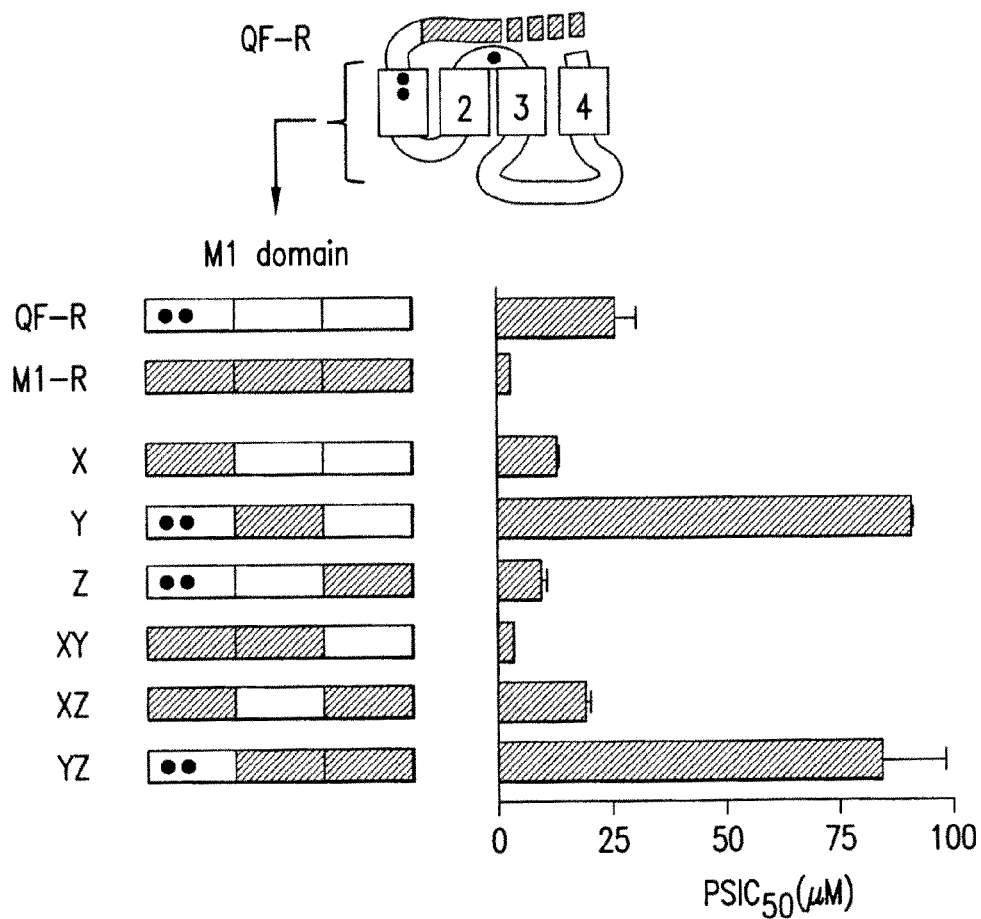

Additional M1 residues influence PS sensitivity. In the third step, other nonconserved residues in UNC-49C were identified that were providing full PS sensitivity to this subunit. The UNC-49C M1 domain was subdivided into three segments of roughly equal length, called X, Y and Z, and tested for the ability to increase PS sensitivity of the QF-R receptor (FIG. 4a). No domain alone was sufficient (top three chimeras, FIG. 4b). High PS sensitivity required both the X and Y segments, while Z was dispensable. Interestingly, there is an incompatibility between mixed X and Y segments. Specifically, the X domain from QF-R juxtaposed to the Y domain from UNC-49C eliminates PS sensitivity (Y and YZ chimeras). This observation shows that residues in the X and Y segments must work together to confer high sensitivity to PS inhibition.

UNC-49C 'QF' residues at 259 and 261, in order to cut down on the number of possible combinations that we needed to test (from 62 to 14). The remaining four residues (257, 258, 262, and 264) were substituted in all possible single, double, and triple mutant combinations. The results of this experiment revealed that maximal PS sensitivity required all four of these UNC-49C amino acids. The most important UNC-49C residues were at positions 257 and 262, while the substitutions at position 264 had little effect. Mutating residue 258 in certain combinations confers a biphasic response. At high PS levels (100 μM) GABA-gated currents are inhibited like the relatively-insensitive starting construct, the Y chimera. However, moderate levels of PS (10 μM) enhance GABA-induced currents, a response not observed in any other subunits. Biphasic curves can be accurately fit using the product of an enhancing

TABLE 3

VIII. Subunit PS GABA

| | $IC_{50}$ (μM) | Slope coefficient | $EC_{50}$ (μM) | Slope coefficient |
|---|---|---|---|---|
| X | 12.8 ± 0.3 (n = 4)[1] | 1.0 + 0.03 (n = 4) | 2.0 ± 0.4 (n = 3) | 1.7 ± 0.6 (n = 3) |
| Y | 90.8 ± 0.5 (n = 3)[1] | 10.4 ± 1.3 (n = 3) | 18.4 ± 1.3 (n = 4) | 1.4 ± 0.1 (n = 4) |
| Z | 9.3 ± 0.6 (n = 4)[1] | 1.05 ± 0.03 (n = 4) | 11.2 ± 3.9 (n = 6) | 1.5 ± 0.1 (n = 6) |
| XY | 3.7 ± 0.5 (n = 7)[2] | 1.6 ± 0.2 (n = 7) | 84.2 ± 9.0 (n = 3) | 6.0 ± 2.5 (n = 3) |
| XZ | 14.4 ± 1.7 (n = 8)[3] | 1.1 ± .06 (n = 8) | 3.1 ± 0.4 (n = 4) | 2.3 ± 0.3 (n = 4) |
| YZ | 84.4 ± 13.7 (n = 4)[3] | 3.5 ± 1.6 (n = 4) | 15.4 ± 4.7 (n = 3) | 1.4 ± 0.2 (n = 3) |

[1]Significantly different from XY chimera (P < 0.05, Students' T test)
[2]Not significantly different from M1-R (P > 0.05, Student's T test)
[3]Significantly different from XY chimera (P < 0.05, Mann-Whitney U test)

Figure 5A:
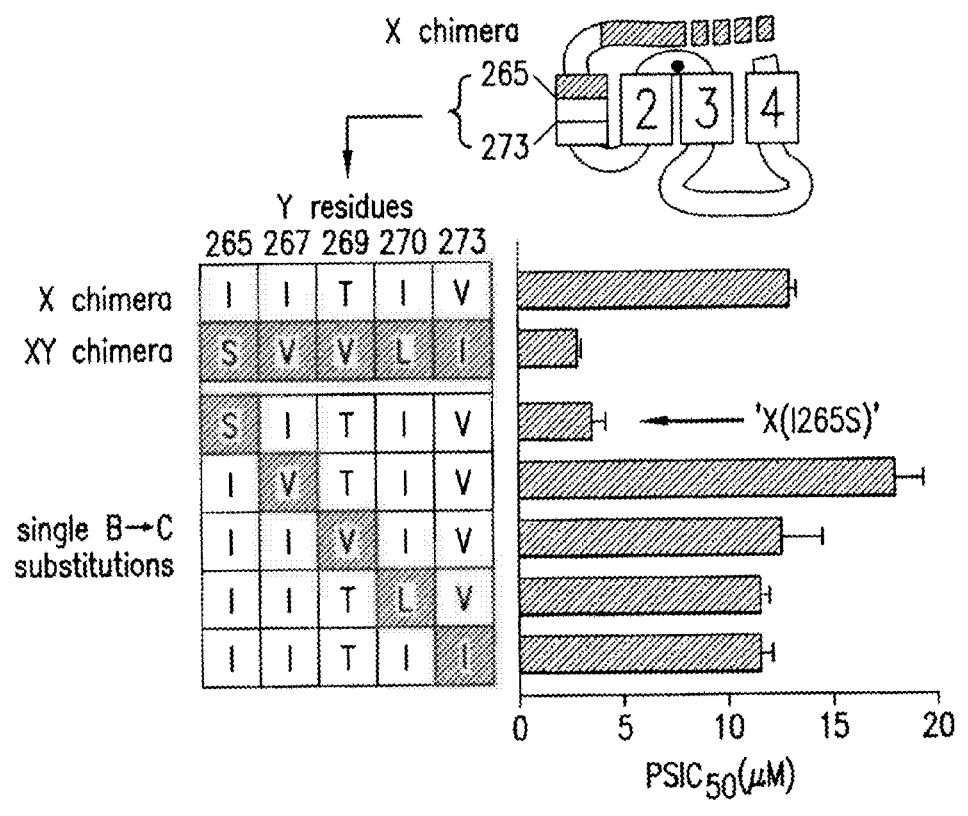

To identify the nonconserved residues within M1 required for maximal PS sensitivity, the specific residues in the X and Y segments that provided maximal PS sensitivity were determined (FIG. 5). First, the X chimera background was used to ascertain which Y segment residues caused the 3.7-fold increase in PS sensitivity seen in the XY chimera. Five residues differ between UNC-49B and UNC-49C within this segment and only these residues are shown in FIG. 5a. The serine at position 265 was sufficient to confer full PS sensitivity; no other residue in the Y segment increased PS sensitivity.

Figure 5B:
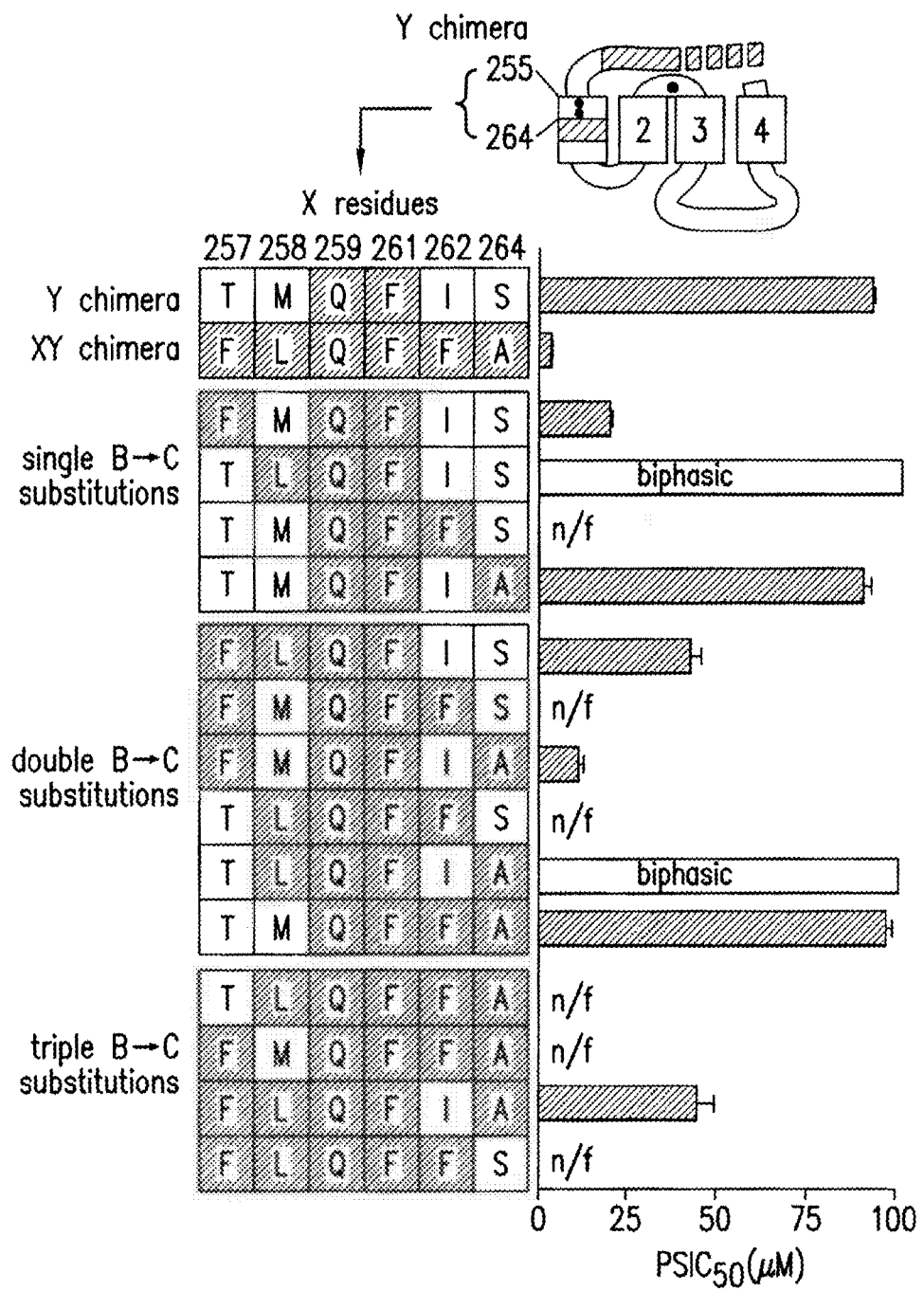
Figure 5C:
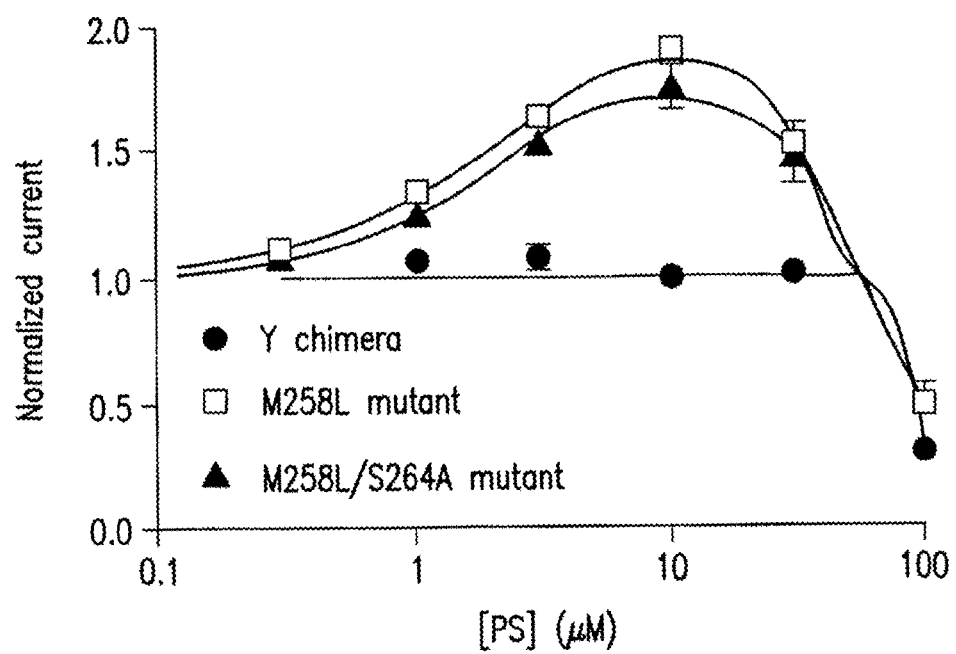

Important residues in the X segment were tested by substituting UNC-49C residues into the Y chimera. Six residues differ between UNC-49C and UNC-49B within the X segment, including the 'QF' conserved residues 259 and 261 (FIG. 5b). These divergent X segment residues were tested by mutating them from UNC-49B to UNC-49C amino acids in the Y chimera background. All mutants were constructed with and an inhibitory Hill equation (FIG. 5c), showing that in these mutant combinations, the M258L mutation can unmask an enhancing site that can function together with the inhibitory site.

Figure 6:
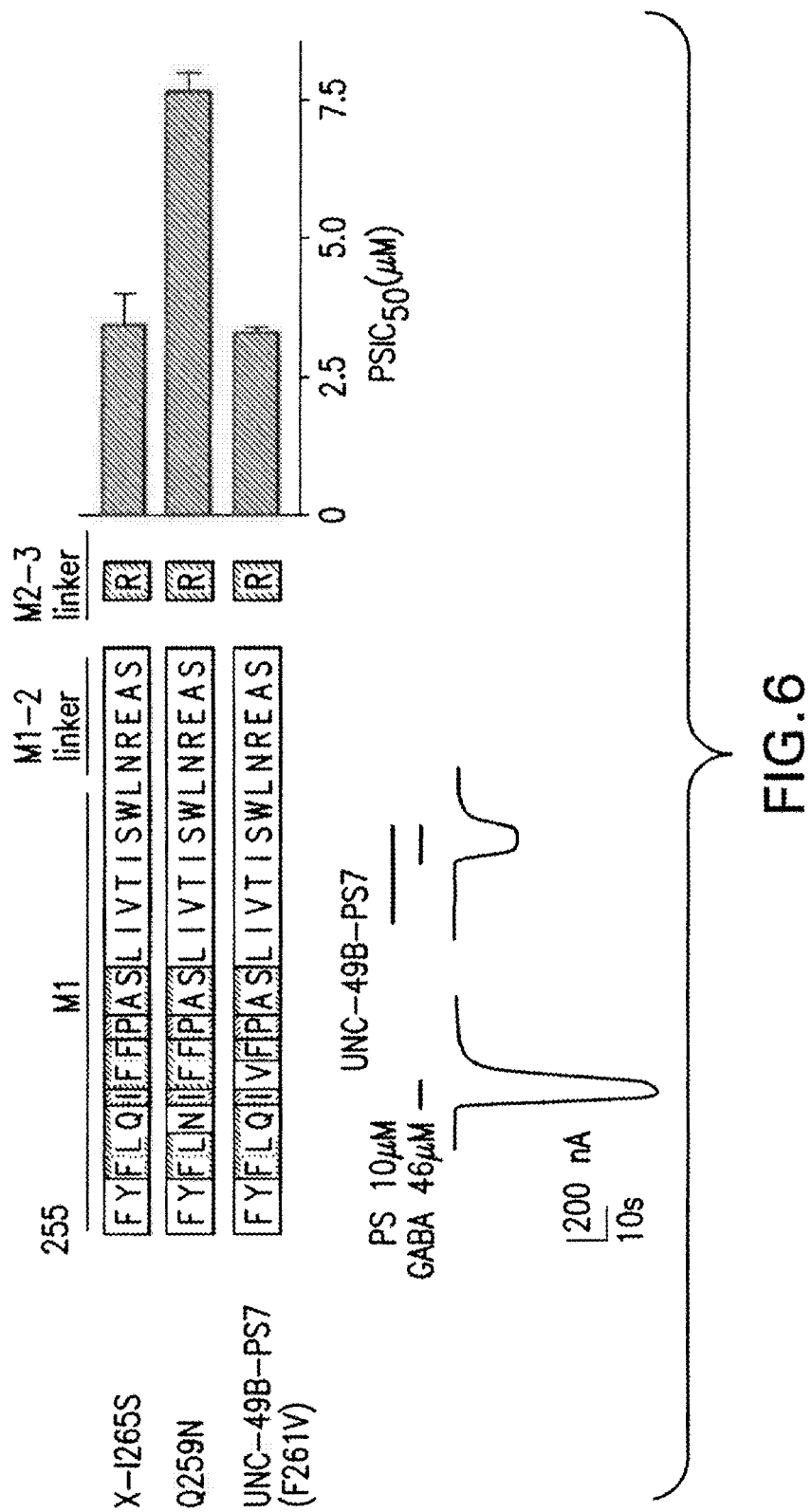

Finally, to determine the minimum number of residues required for PS sensitivity, the conserved 'QF' residues at positions 259 and 261 were reexamined in the context of the maximally responsive receptor 'X(I265S)' presented in FIG. 5a. Reverting residue 259 from glutamine (UNC-49C) to asparagine (UNC-49B) caused a 2.2-fold reduction in PS sensitivity, while reverting residue 261 from phenylalanine (UNC-49C) to valine (UNC-49B) had no effect (FIG. 6). This phenylalanine to valine revertant was named UNC-49B-PS7. It contains the minimum number of UNC-49C residues (seven) necessary to confer the maximum 58-fold increase in PS sensitivity to the UNC-49B subunit.

Figure 7:
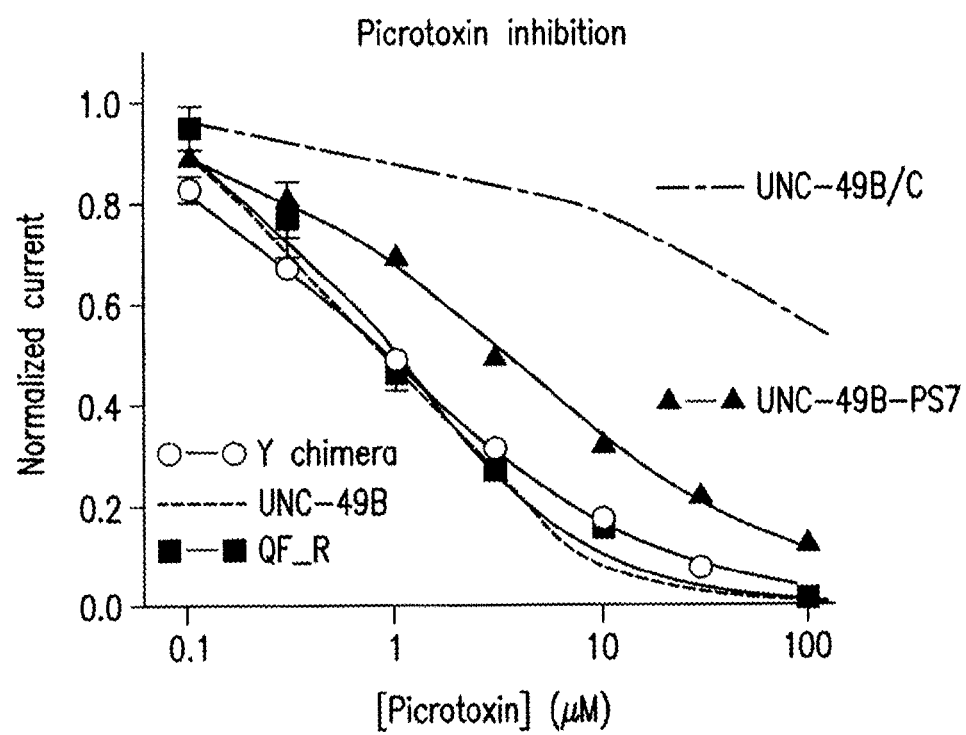

Other allosteric regulators: The allosteric inhibitor picrotoxin was used to determine whether the residues are specific for PS, or if they affect other allosteric regulators of the GABA receptor. Picrotoxin sensitivity did not vary consistently with PS sensitivity among the mutants. For example, the PS sensitivities of the wild-type UNC-49B, the QF-R subunit, and the Y chimera differ over an eight-fold range (Tables 1, 2), whereas their picrotoxin sensitivities are identical (FIG. 7, and (Bamber et al., 2003). Conversely, the PS sensitivities of UNC-49B-PS7 and the UNC-49B/C heteromer differ by 1.4-fold (Tables 1, 3), but their picrotoxin sensitivities differ by 50-fold (FIG. 7, Bamber et al., 2003). Clearly, other residues in these subunits confer picrotoxin effects. These results provide evidence that the PS-sensitive residues identified here play a specific role in neurosteroid action, and not a general role in allosteric inhibition.

The effect of the positively-charged residue in the M2-3 linker on PS responsiveness shows that PS inhibits the GABA receptor by affecting channel gating. Efficient gating of a related ligand-gated chloride channel, the glycine receptor, requires a positively-charged residue in the M2-3 linker (Rajendra et al., 1995). A similar dependence is observed with UNC-49B: wild-type UNC-49B lacks this positively-charged residue, and is relatively insensitive to GABA, while introducing this positive charge consistently increased GABA sensitivity.

The M1 domain appears to be the site at which the GABA activation and PS inhibition mechanisms converge. In addition to their importance for PS sensitivity, M1 residues also strongly affect GABA sensitivity. GABA $EC_{50}$ values ranged from 0.9 to 256 μM among receptors containing mutations in the M1 domain (Table 4). These mutations were not in a region that contributes residues to the GABA binding site, so these variations can reflect alterations in receptor transitions downstream of GABA binding (Colquhoun, 1998). Several other studies have demonstrated that mutations in M1 affect gating and desensitization in $GABA_A$ receptors and other cysteine-loop receptors (Bianchi et al., 2001; Dang et al., 2000; England et al., 1999). The dual role of M1 in GABA activation and PS inhibition shows that PS binding to the receptor can alter the position or constrain the motion of the identified M1 residues, with the result that GABA gating becomes impaired.

Figure 8A:
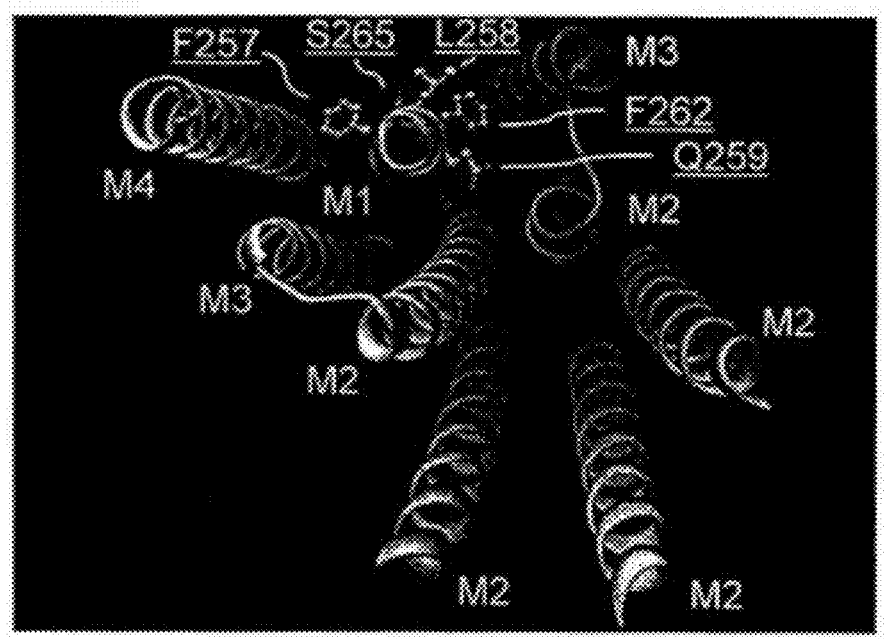
Figure 8B:
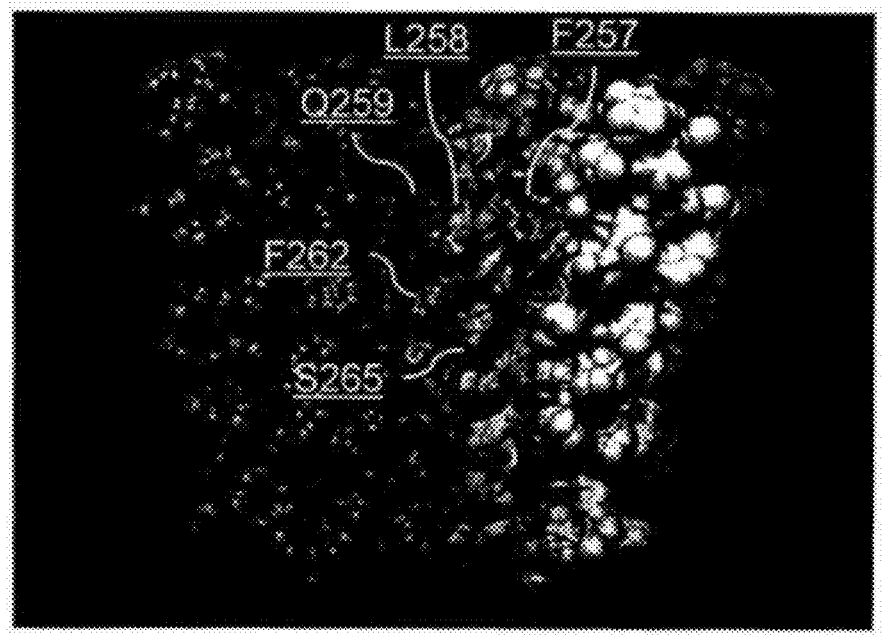
Figure 9:
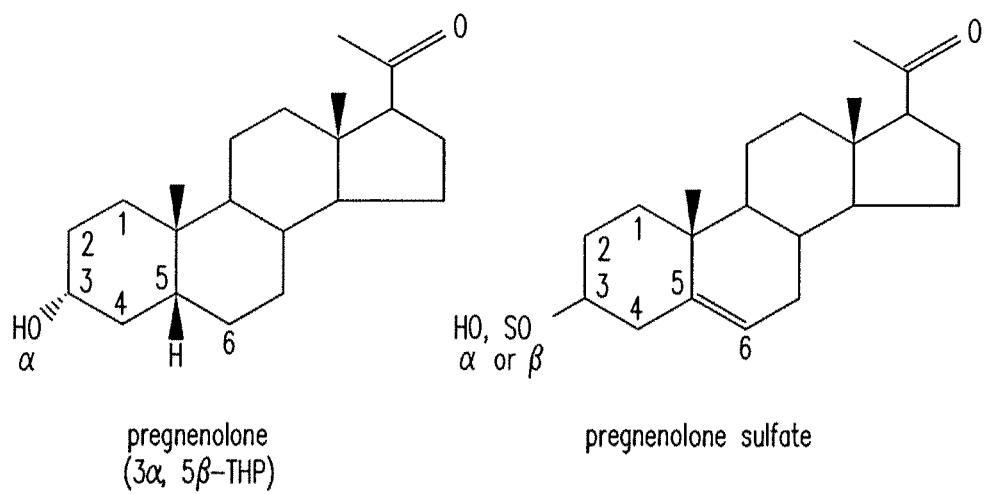
FIG. 9 shows structures of pregnanolone and PS. Carbons 1-6 of the steroid backbone are numbered; orientation of groups at carbon 3 is indicated.
Figure 10:
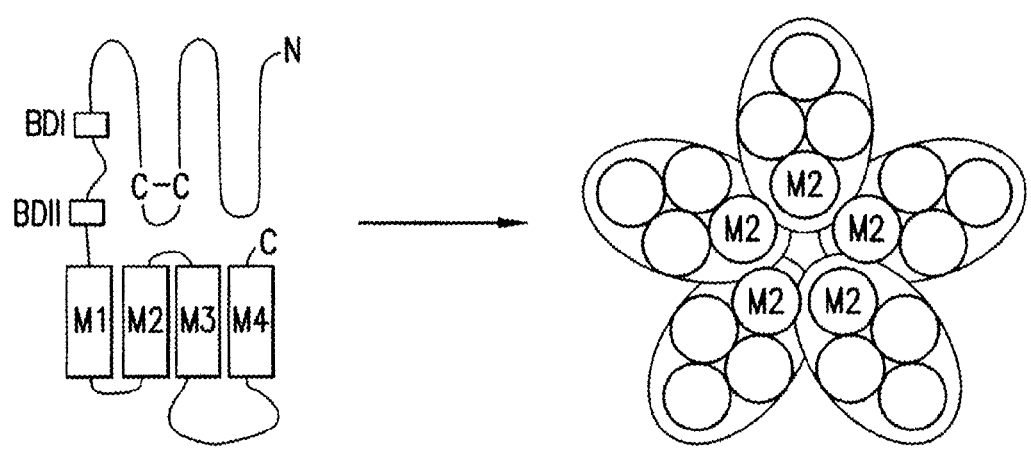
FIG. 10 shows the structure of a GABAA receptor. Structure of a single subunit is shown at left, structure of the pentameric complex is shown at right.

A homology model of the $GABA_A$ receptor has been constructed based on the nicotinic receptor (FIG. 8). The side chains along one face of M2 line the channel pore; the opposite side of M2 transmembrane domain is apposed to the M1 domain. Opening of the channel is believed to involve rotation of the M2 helices of the five subunits (Miyazawa et al., 2003). PS binding to the receptor can reposition M1, altering its interaction with M2 side chains to favor closed states. It has been shown that M1 residues L258, Q259, F262 and S265 are important for PS responsiveness. In fact, the side chain of residue Q259 can be oriented toward the M2 helix, and can mediate an interaction between M1 and M2. By contrast, the side chains of L258 and S265 are oriented away from the other transmembrane helices. S265 lies within the cell membrane and is exposed to membrane lipids. Therefore it can bind the hydrophobic moieties of PS that are stable within the cell membrane. L258 can lie at the extracellular boundary of the cell membrane. Therefore, this residue can interact with PS atoms nearer to the negatively-charged sulfate group, which is presumably forced to remain in contact with the hydrophilic extracellular environment.

Previous studies of $GABA_A$ and glycine receptors had identified important residues in the M1, M2 and M3 domains for allosteric regulation (Belelli et al., 1997; Carlson et al., 2000; ffrench-Constant et al., 1993; Mihic et al., 1997). Mutating these residues in certain GABA receptor subunits also affects neurosteroid modulation (Akk et al., 2001; Chang et al., 2003; Morris & Amin, 2004), indicating that neurosteroids and other drugs share some mechanisms of allosteric regulation in common. By contrast the residues identified in this study do not mediate the effects of picrotoxin, showing that the identified residues are specifically involved in neurosteroid modulation, and not in the actions of unrelated modulators.

TABLE 4

| | IX. Subunit PS GABA | | | |
|---|---|---|---|---|
| | $IC_{50}$ (μM) | Slope coefficient | $EC_{50}$ (μM) | Slope coefficient |
| X(I265S) | 3.43 ± 0.6 (n = 6)[1] | 1.1 ± 0.1 (n = 6) | 49.2 ± 5.8 (n = 3) | 0.8 ± 0.1 (n = 3) |
| X(I267V) | 17.9 ± 1.4 (n = 3)[2] | 1.1 ± 0.05 (n = 3) | 2.9 ± 0.1 (n = 3) | 1.4 ± 0.7 (n = 3) |
| X(T269V) | 12.4 ± 1.9 (n = 3)[3] | 1.2 ± 0.1 (n = 3) | 6.5 ± 0.8 (n = 3) | 2.9 ± 0.2 (n = 3) |
| X(I270L) | 11.5 ± 0.5 (n = 4)[2] | 1.5 ± 0.1 (n = 4) | 0.9 ± 0.2 (n = 3) | 1.4 ± 0.7 (n = 3) |
| X(V273I) | 11.6 ± 0.5 (n = 3)[2] | 1.0 ± 0.02 (n = 3) | 12.1 ± 0.5 (n = 3) | 3.0 ± 0.3 (n = 3) |
| Y(T257F) | 18.6 ± 0.9 (n = 4)[2] | 1.3 ± 0.06 (n = 4) | 1.4 ± 0.5 (n = 3) | 0.7 ± 0.07 (n = 3) |
| Y(M258L) | 100 (biphasic) | n/d | 249.3 ± 28.5 (n = 5) | 1.2 ± 0.03 (n = 5) |
| Y(S264A) | 88.7 ± 2.9 (n = 4)[3] | 5.3 ± 1.8 (n = 4) | 24.4 ± 3.3 (n = 3) | 0.8 ± 0.1 (n = 3) |
| Y(T257F/M258L) | 41.5 ± 3.0 (n = 4)[3] | 2.3 ± 0.2 (n = 4) | 33.4 ± 2.6 (n = 3) | 1.9 ± 0.2 (n = 3) |
| Y(T257F/S264A) | 10.6 ± 1.9 (n = 4)[2,4] | 0.9 ± 0.08 (n = 4) | 1.2 ± 0.1 (n = 3) | 2.6 ± 0.4 (n = 3) |
| Y(M258L/S264A) | 100 (biphasic) | n/d | 256.0 ± 37.6 (n = 4) | 1.22 ± 0.1 (n = 4) |
| Y(I262F/S264A) | 97.6 ± 1.9 (n = 4)[3] | 11.5 ± 0.3 (n = 3) | 6.3 ± 2.1 (n = 3) | 1.5 ± 0.6 (n = 3) |
| Y(T257F/M258L/S264A) | 44.4 ± 4.8 (n = 4)[3] | 1.44 ± 0.1 (n = 4) | 12.8 ± 1.3 (n = 3) | 2.3 ± 0.3 (n = 3) |
| X(I265S, Q259N) | 7.7 ± 0.3 (n = 4)[5] | 0.9 ± 0.0 (n = 4) | 80.4 ± 10.0 (n = 4) | 0.77 ± 0.05 (n = 4) |
| UNC-49B-PS7 | 3.3 ± 0.1 (n = 4)[6,7] | 1.0 ± 0.0 (n = 4) | 46.2 ± 11.1 (n = 4) | 1.06 ± 0.04 (n = 4) |

[1]Not significantly different from XY (P > 0.05, Student's T test)
[2]Significantly different from XY (P < 0.05, Student's T test)
[3]Significantly different from XY (P < 0.05, Mann-Whitney U test)
[4]Significantly different from T257 (P < 0.05, Student's T test)
[5]Significantly different from X(I265S) (P < 0.05, Mann-Whitney U test)
[6]Not significantly different from X(I265S) (P > 0.05, Mann-Whitney U test)
[7]Not significantly different from M1-R (P > 0.05, Mann-Whitney U test)

1. Example 5

Screening for GABA$_A$ Receptor Ligands

Many methods have been described for high-throughput screening that are suitable to identify compounds that modulate GABA$_A$ receptor function. These include high-throughput electrophysiology screening, fluorescence membrane probe assays such as FLIPR and VIPR assays, quenching of fluorescent protein constructs in the presence of high chloride ion concentrations, colorimetric assays for halide ion influx, and enhancement of GABA site radioligand binding. Literature containing examples of these methods includes, but is not limited to, Asmild, M. et al. (2003) Receptors and Channels 9:49-58 and Willumsen, N. et al. (2003) Receptors and Channels 9:3-12; Jensen, A. and Kristiansen, U. (2004) Biochem. Pharmacol. 67:1789-1799; Thompson, SA et al. (2004) Brit. J. Pharmacol. 142:97-106; Kruger, W. et al. (2005) Neuroscience Letters 380:340-345; Tang, W. and Wildey, M. (2004). J. Biomol. Screening 9:607; Mehta, A. and Ticku, M. (1998) Brain Research 805:88-94; Brodinsky et al. (1997) Neurochem Int. 31:313-317; and Chigr et al. (2002) Clinical and Experimental Pharmacology and Physiology 29:291-298, all of which are hereby incorporated by reference in their entirety for their teachings concerning screening assays.

Wild-type GABA$_A$ receptors expressed in mammalian cells are neurosteroid sensitive, but mutant GABA$_A$ receptors (containing mutations in the 'XY' region of the M1 transmembrane domain) are not. This differential neurosteroid sensitivity is demonstrated for mammalian GABA$_A$ receptors in mammalian cells in Hosie et al. 2005 (Nature 444:486). Similarly, differential PS sensitivity for wild-type and mutant C. elegans GABA$_A$ receptors is demonstrated in FIG. 29.

The following example shows a method for how a candidate compound (the 'test compound') can be evaluated for activity at the neurosteroid site of the α1β2γ2 GABA$_A$ receptor. The method is based on high-throughput electrophysiology. The same logic and experimental flow are applicable for any of the high-throughput methods disclosed herein.

Cell lines expressing two α1β2γ2 GABA$_A$ receptor subunits variants are derived. One variant cell line expresses the wild-type subunits. The other expresses a mutant α1 subunit along with the wild-type β2 and γ2 subunits. The mutation in the α1 subunit eliminates the neurosteroid site. The α1 ceXY subunit shown in FIG. 28 is an example of how the neurosteroid site can be eliminated. GABA sensitivity of the wild-type and mutant receptors is measured, as demonstrated in FIG. 29a. The concentration of GABA required to produce the half-maximal response (the EC$_{50}$) is determined.

A four-step protocol is employed to assess whether a test compound can modulate the GABA$_A$ receptors through its neurosteroid site: 1) Measure the response of cells expressing the wild-type GABA$_A$ receptor to EC$_{50}$ GABA; 2) Measure the response of cells expressing the mutant GABA$_A$ receptor (in which the neurosteroid site is eliminated) to EC$_{50}$ GABA; 3) Measure the response of cells expressing the wild-type GABA$_A$ receptor to EC$_{50}$ GABA plus the test compound in concentrations ranging from 1 nM to 1000 µM (twelve concentrations at 1 nM, 3 nM, 10 nM, 30 nM etc. for example); 4) Measure the response of cells expressing the mutant GABA$_A$ receptor (in which the neurosteroid site is eliminated) to EC$_{50}$ GABA plus the test compound at the same concentrations as in step 3.

The test compound is judged to be a ligand of the neurosteroid site if it modulates (i.e. increases or decreases) the GABA response of the wild-type receptor, but fails to modulate the GABA response of the mutant GABA receptor in which the neurosteroid site is eliminated. A similar judgment is made if the test compound modulates mutant receptors less potently compared to the wild-type. The test compound is also be judged to be a ligand of the neurosteroid site if it directly activates the wild-type receptor (i.e. in the absence of GABA), but fails to directly activate the mutant receptor at the same concentrations.

The above example shows how a library of test compounds can be evaluated for activity at the neurosteroid site on a single GABA$_A$ receptor subtype, namely the α1β2γ2 subtype. It is estimated that there are at least 12 major subtypes of GABA$_A$ receptors in the brain, and theoretically thousands of subtypes can be assembled from the subunits encoded in the human genomes (i.e. α1-6, β1-3, γ1-3, δ, ε, ρ1-3). The methods disclosed herein can be used to screen compounds against any of the proven or theoretically possible GABA$_A$ receptor subtypes.

B. REFERENCES

AKK, G., BRACAMONTES, J. & STEINBACH, J. H. (2001). Pregnenolone sulfate block of GABA(A) receptors: mechanism and involvement of a residue in the M2 region of the alpha subunit. J. Physiol., 532, 673-84.

AMIN, J. AND D. S. WEISS, GABA$_A$ receptor needs two homologous domains of the β-subunit for activation by GABA but not by pentobarbital. Nature, 1993. 366(6455): p. 565-569.

BAMBER, B. A., BEC, A. A., TWYMAN, R. E. & JORGENSEN, E. M. (1999). The Caenorhabditis elegans unc-49 Locus Encodes Multiple Subunits of a Heteromultimeric GABA Receptor. J. Neurosci., 19, 5348-5359.

BAMBER, B. A., RICHMOND, J. E., OTTO, J. F. & JORGENSEN, E. M. (2005). Composition of the GABA receptor at the Caenorhabditis elegans neuromuscular junction. Br. J. Pharmacol., 144, 502-509.

BAMBER, B. A., TWYMAN, R. E. & JORGENSEN, E. M. (2003). Pharmacological characterization of the homomeric and heteromeric UNC-49 GABA receptors in C. elegans. Br. J. Pharmacol., 138, 883-93.

BARNARD, E. A., et al., International Union of Pharmacology. XV. Subtypes of gamma-aminobutyric acidA receptors: classification on the basis of subunit structure and receptor function. Pharmacol Rev, 1998. 50(2): p. 291-313.

BAULAC, S., et al., First genetic evidence of GABA$_A$ receptor dysfunction in epilepsy: a mutation in the gamma2-subunit gene. Nat Genet, 2001. 28(1): p. 46-8.

BELELLI, D. & LAMBERT, J. J. (2005). Neurosteroids: endogenous regulators of the GABA(A) receptor. Nat. Rev. Neurosci., 6, 565-75.

BELELLI, D., LAMBERT, J. J., PETERS, J. A., WAFFORD, K. & WHITING, P. J. (1997). The interaction of the general anesthetic etomidate with the gamma-aminobutyric acid type A receptor is influenced by a single amino acid. Proc. Natl. Acad. Sci. U.S.A., 94, 11031-6.

BEYENBURG, S., et al., Neuroactive steroids and seizure susceptibility. Epilepsy Res, 2001. 44(2-3): p. 141-53.

BIANCHI, M. T., HAAS, K. F. & MACDONALD, R. L. (2001). Structural determinants of fast desensitization and desensitization-deactivation coupling in GABA$_A$ receptors. J. Neurosci., 21, 1127-36.

BLUM, D. E., New drugs for persons with epilepsy. Adv Neurol, 1998. 76: p. 57-87.

CARLSON, B. X., ENGBLOM, A. C., KRISTIANSEN, U., SCHOUSBOE, A. & OLSEN, R. W. (2000). A single glycine residue at the entrance to the first membrane-spanning domain of the gamma-aminobutyric acid type A receptor beta(2) subunit affects allosteric sensitivity to GABA and anesthetics. Mol. Pharmacol., 57, 474-84.

CHANG, C. S., OLCESE, R. & OLSEN, R. W. (2003). A single M1 residue in the beta2 subunit alters channel gating of GABA$_A$ receptor in anesthetic modulation and direct activation. *J. Biol. Chem.*, 278, 42821-8.

CHEN, C. AND H. OKAYAMA, High-efficiency transformation of mammalian cells by plasmid DNA. Mol Cell Biol, 1987. 7(8): p. 2745-52.

COLQUHOUN, D. (1998). Binding, gating, affinity and efficacy: the interpretation of structure-activity relationships for agonists and of the effects of mutating receptors. *Br. J. Pharmacol.*, 125, 924-47.

DANG, H., ENGLAND, P. M., FARIVAR, S. S., DOUGHERTY, D. A. & LESTER, H. A. (2000). Probing the role of a conserved M1 proline residue in 5-hydroxytryptamine(3) receptor gating. *Mol Pharmacol*, 57, 1114-22.

DOYLE, D. A., et al., The structure of the potassium channel: molecular basis of K+ conduction and selectivity. Science, 1998. 280(5360): p. 69-77.

ENGLAND, P. M., ZHANG, Y., DOUGHERTY, D. A. & LESTER, H. A. (1999). Backbone mutations in transmembrane domains of a ligand-gated ion channel: implications for the mechanism of gating. *Cell*, 96, 89-98.

ETTER, A., et al., Picrotoxin blockade of invertebrate glutamate-gated chloride channels: subunit dependence and evidence for binding within the pore. J Neurochem, 1999. 72(1): p. 318-26.

FRENCH-CONSTANT, R. H., ROCHELEAU, T. A., STEICHEN, J. C. & CHALMERS, A. E. (1993). A point mutation in a *Drosophila* GABA receptor confers insecticide resistance. *Nature*, 363, 449-451.

FRYE, C. A., The neurosteroid 3 alpha, 5 apha-THP has antiseizure and possible neuroprotective effects in an animal model of epilepsy. Brain Res, 1995. 696(1-2): p. 113-20.

GASIOR, M., CARTER, R. B. & WITKIN, J. M. (1999). Neuroactive steroids: potential therapeutic use in neurological and psychiatric disorders. *Trends Pharmacol. Sci.*, 20, 107-112.

GINGRICH, K. J., W. A. ROBERTS, AND KASS, R. S. Dependence of the GABAA receptor gating kinetics on the alpha-subunit isoform: implications for structure-function relations and synaptic transmission. J Physiol (Lond), 1995. 489(Pt 2): p. 529-43.

GINGRICH, K. J. AND P. M. BURKAT, Zn2+ inhibition of recombinant GABAA receptors: an allosteric, state-dependent mechanism determined by the gamma-subunit. J Physiol, 1998. 506(Pt 3): p. 609-25.

HAAS, K. F. AND R. L. MACDONALD, GABAA receptor subunit gamma2 and delta subtypes confer unique kinetic properties on recombinant GABAA receptor currents in mouse fibroblasts. J Physiol, 1999. 514(Pt 1): p. 27-45.

HANNER, M., et al., Binding of correolide to the K(v)1.3 potassium channel: characterization of the binding domain by site-directed mutagenesis. Biochemistry, 2001. 40(39): p. 11687-97.

HARRISON, N. L., S. VICINI, AND J. L. BARKER, A steroid anesthetic prolongs inhibitory postsynaptic currents in cultured rat hippocampal neurons. J Neurosci, 1987. 7(2): p. 604-9.

HERZOG, A. G., P. KLEIN, AND B. J. RANSIL, Three patterns of catamenial epilepsy. Epilepsia, 1997. 38(10): p. 1082-8.

JONES, M. V. AND G. L. WESTBROOK, Desensitized states prolong GABAA channel responses to brief agonist pulses. Neuron, 1995. 15(1): p. 181-91.

JONES, M. V., JONAS, P., SAHARA, Y. & WESTBROOK, G. L. (2001). Microscopic kinetics and energetics distinguish GABA(A) receptor agonists from antagonists. *Biophys. J.*, 81, 2660-70.

JONES, M. V. AND G. L. WESTBROOK, Shaping of IPSCs by endogenous calcineurin activity. J Neurosci, 1997. 17(20): p. 7626-33.

JONES, M. V., et al., Defining affinity with the GABAA receptor. J Neurosci, 1998. 18(21): p. 8590-604.

KERRIGAN, J. F., SHIELDS, W. D., NELSON, T. Y., BLUESTONE, D. L., DODSON, W. E., BOURGEOIS, B. F., PELLOCK, J. M., MORTON, L. D. & MONAGHAN, E. P. (2000). Ganaxolone for treating intractable infantile spasms: a multicenter, open-label, add-on trial. *Epilepsy Res.*, 42, 133-9.

KOKATE, T. G., et al., Convulsant actions of the neurosteroid pregnenolone sulfate in mice. Brain Res, 1999. 831(1-2): p. 119-24.

LAMBERT, J. J., et al., Neurosteroids and GABA$_A$ receptor function. Trends Pharmacol. Sci., 1995. 16(9): p. 295-303.

LAXER, K., BLUM, D., ABOU-KHALIL, B. W., MORRELL, M. J., LEE, D. A., DATA, J. L. & MONAGHAN, E. P. (2000). Assessment of ganaxolone's anticonvulsant activity using a randomized, double-blind, presurgical trial design. Ganaxolone Presurgical Study Group. *Epilepsia*, 41, 1187-94.

LESTER, H. A., DIBAS, M. I., DAHAN, D. S., LEITE, J. F. & DOUGHERTY, D. A. (2004). Cys-loop receptors: new twists and turns. *Trends Neurosci.*, 27, 329-36.

LYNCH, J. W., et al., Mutations affecting the glycine receptor agonist transduction mechanism convert the competitive antagonist, picrotoxin, into an allosteric potentiator. J Biol Chem, 1995. 270(23): p. 13799-806.

MACONOCHIE, D. J., J. M. ZEMPEL, AND J. H. STEINBACH, How quickly can GABAA receptors open? Neuron, 1994. 12(1): p. 61-71.

MACDONALD, R. L., C. J. ROGERS, AND R. E. TWYMAN, Kinetic properties of the GABAA receptor main conductance state of mouse spinal cord neurones in culture. J Physiol, 1989. 410: p. 479-99.

MACDONALD, R. L. & OLSEN, R. W. (1994). GABA$_A$ receptor channels. *Ann. Rev. Neurosci.*, 17, 569-602.

MAITRA, R. AND J. N. REYNOLDS, Modulation of GABA$_A$ receptor function by neuroactive steroids: evidence for heterogeneity of steroid sensitivity of recombinant GABA$_A$ receptor isoforms. Can J Physiol Pharmacol, 1998. 76(9): p. 909-20.

MAJEWSKA, M. D. (1992). Neurosteroids: Endogenous Bimodal Modulators of the GABA$_A$ Receptor. Mechanism of Action and Physiological Significance. *Progress in Neuorobiology*, 38, 379-395.

MCCLELLAN, A. M. AND R. E. TWYMAN, Receptor system response kinetics reveal functional subtypes of native murine and recombinant human GABA$_A$ receptors. J Physiol, 1999. 515(Pt 3): p. 711-27.

MCINTIRE, S. L., E. JORGENSEN, AND H. R. HORVITZ, Genes required for GABA function in *Caenorhabditis elegans*. Nature, 1993b. 364(6435): p. 334-337.

MELLON, S. H. & GRIFFIN, L. D. (2002). Neurosteroids: biochemistry and clinical significance. *Trends. Endocrinol. Metab.*, 13, 3543.

MIENVILLE, J. M. AND S. VICINI, Pregnenolone sulfate antagonizes GABAA receptor-mediated currents via a reduction of channel opening frequency. Brain Res, 1989. 489(1): p. 190-4.

MIHIC, S. J., YE, Q., WICK, M. J., KOLTCHINE, V. V., KRASOWSKI, M. D., FINN, S. E., MASCIA, M. P., VALENZUELA, C. F., HANSON, K. K., GREENBLATT, E. P., HARRIS, R. A. & HARRISON, N. L. (1997). Sites of alcohol and.volatile anaesthetic action on GABA$_A$ and glycine receptors. *Nature*, 389, 385-389.

MISTRY, D. K. AND G. A. COTTRELL, Actions of steroids and bemegride on the GABAA receptor of mouse spinal neurones in culture. Exp Physiol, 1990. 75(2): p. 199-209.

MITCHESON, J. S., et al., A structural basis for drug-induced long QT syndrome. Proc Natl Acad Sci USA, 2000. 97(22): p. 12329-33.

MIYAZAWA, A., FUJIYOSHI, Y. & UNWIN, N. (2003). Structure and gating mechanism of the acetylcholine receptor pore. *Nature*, 423, 949-55.

MORRIS, K. D. & AMIN, J. (2004). Insight into the mechanism of action of neuroactive steroids. *Mol. Pharmacol.*, 66, 56-69.

Morris, K. D., C. N. Moorefield, And J. Amin, Differential modulation of the gamma-aminobutyric acid type C receptor by neuroactive steroids. Mol Pharmacol, 1999. 56(4): p.752-9.

Morrow, A. L., Khisti, R., Tokunaga, S., McDaniel, J. R. & Matthews, D. B. (2004). GABAergic neuroactive steroids modulate selective ethanol actions: mechanisms and significance. In *Neurosteroid effects in the central nervous system.* ed Smith, S. S. pp. 219-245. Boca Raton, Fla.: CRC Press.

Mozrzymas, J. W., et al., Chlorpromazine inhibits miniature GABAergic currents by reducing the binding and by increasing the unbinding rate of $GABA_A$ receptors. J Neurosci, 1999. 19(7): p. 2474-88.

Milsson, K. R., Zorumski, C. F. & Covey, D. F. (1998). Neurosteroid analogues. 6. The synthesis and $GABA_A$ receptor pharmacology of enantiomers of dehydroepiandrosterone sulfate, pregnenolone sulfate, and (3a,5b)-3-hydroxypregnan-20-one sulfate. *J. Med. Chem.,* 41, 2604-2613.

Olsen, R. W. & Tobin, A. J. (1990). Molecular biology of $GABA_A$ receptors. *FASEB J.,* 4, 1469-1480.

Park-Chung, M., Malayev, A., Purdy, R. H., Gibbs, T. T. & Farb, D. H. (1999). Sulfated and unsulfated steroids modulate gamma-aminobutyric acidA receptor function through distinct sites. *Brain Res.,* 830, 72-87.

Paul, S. M. & Purdy, R. H. (1992). Neuroactive steroids. *FASEB J.,* 6, 2311-22.

Pistis, M., et al., Complementary regulation of anaesthetic activation of human ($\alpha_6\beta_3\gamma_{2L}$) and *Drosophila* (RDL) GABA receptors by a single amino acid residue. J Physiol (Lond), 1999. 515(Pt 1): p. 3-18.

Pribella, I., et al., The atypical M2 segment of the beta subunit confers picrotoxinin resistance to inhibitory glycine receptor channels [published erratum appears in EMBO J Mar. 15, 1994;13(6):1493]. Embo J, 1992. 11(12): p. 4305-11.

Puia, G., et al., Neurosteroids act on recombinant human $GABA_A$ receptors. Neuron, 1990. 4(5): p. 759-65.

Rajendra, S., Lynch, J. W., Pierce, K. D., French, C. R., Barry, P. H. & Schofield, P. R. (1995). Mutation of an arginine residue in the human glycine receptor transforms beta-alanine and taurine from agonists into competitive antagonists. *Neuron,* 14, 169-175.

Reddy, D. S. And M. A. Rogawski, Enhanced anticonvulsant activity of ganaxolone after neurosteroid withdrawal in a rat model of catamenial epilepsy. J Pharmacol Exp Ther, 2000. 294(3): p. 909-15.

Rick, C. E., et al., Neurosteroids act on the $GABA_A$ receptor at sites on the N-terminal side of the middle of TM2. Neuroreport, 1998. 9(3): p. 379-383.

Rupprecht, R. (2003). Neuroactive steroids: mechanisms of action and neuropsychopharmacological properties. *Psychoneuroendocrinology,* 28, 139-68.

Sali, A. & Blundell, T. L. (1993). Comparative protein modelling by satisfaction of spatial restraints. *J. Mol. Biol.,* 234, 779-815.

Shen, W., Mennerick, S., Zorumski, E. C., Covey, D. F. & Zorumski, C. F. (1999). Pregnenolone sulfate and dehydroepiandrosterone sulfate inhibit GABA-gated chloride currents in *Xenopus* oocytes expressing picrotoxin-insensitive $GABA_A$ receptors. *Neuropharmacology,* 38, 267-271.

Shen, W., et al., Pregnenolone sulfate modulates inhibitory synaptic transmission by enhancing $GABA_A$ receptor desensitization. J Neurosci, 2000. 20(10): p. 3571-9.

Thompson, J. D., Higgins, D. G. & Gibson, T. J. (1994). CLUSTAL W: improving the sensitivity of progressive multiple sequence alignment through sequence weighting, position-specific gap penalties and weight matrix choice. *Nucleic Acids Res.,* 22, 4673-4680.

Twyman, R. E., C. J. Rogers, And R. L. Macdonald, Intraburst kinetic properties of the GABAA receptor main conductance state of mouse spinal cord neurones in culture. J Physiol, 1990. 423: p. 193-220.

Twyman, R. E. And R. L. Macdonald, Neurosteroid regulation of $GABA_A$ receptor single-channel kinetic properties of mouse spinal cord neurons in culture. J Physiol, 1992. 456: p. 215-45.

Ueno, S., et al., Bicuculline and gabazine are allosteric inhibitors of channel opening of the $GABA_A$ receptor. J Neurosci, 1997. 17(2): p. 625-634.

Vallee, M., Mayo, W., Darnaudery, M., Corpechot, C., Young, J., Koehl, M., Le Moal, M., Baulieu, E. E., Robel, P. & Simon, H. (1997). Neurosteroids: deficient cognitive performance in aged rats depends on low pregnenolone sulfate levels in the hippocampus. *Proc. Natl. Acad. Sci. U.S.A.,* 94, 14865-14870.

Walker, M. C. And J. W. Sander, New anti-epileptic drugs. Expert Opin Investig Drugs, 1999. 8(10): p. 1497-1510.

Wallace, R. H., et al., Mutant GABAA receptor gamma2-subunit in childhood absence epilepsy and febrile seizures. Nat Genet, 2001. 28(1): p. 49-52.

Wooltorton, J. R., S. J. Moss, And T. G. Smart, Pharmacological and physiological characterization of murine homomeric $\beta$3 $GABA_A$ receptors. Eur J Neurosci, 1997. 9(11): p. 2225-2235.

Wu, F. S., Gibbs, T. T. & Farb, D. H. (1991). Pregnenolone sulfate: a positive allosteric modulator at the N-methyl-D-aspartate receptor. *Mol. Pharmacol.,* 40, 333-6.

Zaman, S. H., Shingai, R., Harvey, R. J., Darlison, M. G. & Barnard, E. A. (1992). Effects of subunit types of the recombinant $GABA_A$ receptor on the response to a neurosteroid. *Eur. J. Pharmacol.,* 225, 321-30.

Zhu, W. J. And S. Vicini, Neurosteroid prolongs $GABA_A$ channel deactivation by altering kinetics of desensitized states. J. Neurosci., 1997. 17: p. 4022-4031.

Zhu, W. J., et al., Delta subunit inhibits neurosteroid modulation of $GABA_A$ receptors. J Neurosci, 1996. 16(21); p. 6648-56.

C. SEQUENCES

```
                                            SEQ ID NO: 1
Caenorhabditis elegans ionotropic GABA receptor
subunit UNC-49B.3
LOCUS = AF151643 2601 bp INV 27-JUL-2001
mRNA translation Protein id = AAD42385.1
amino acid sequence
MARPFTLIVLLSAHLCLHVVVTQDEDSHINTQLLSSVLDRLTNR

TTYDKRLRPRYGEKPVDVGITIHVSSISAVSEVDMDFTLDFYMRQTWQDP
RLAFGSLD

LGLSKEIDSLTVGVDYLDRLWKPDTFFPNEKKSFFHLATTHNSFLRIEGD
GTVYTSQR

LTVTATCPMDLKLFPMDSQHCKLEIESYGYETKDIDYYWGKKRTDLEITA
VKFDTFQL

PQFQPTLYFVNTTKAETSSGKYVRLALEVILVRNMGFYTMNIVIPSILIV
TISWVSFW

LNREASPARVGLGVTTVLTMTTLITTTNNSMPKVSYVKGLDVFLNFCFVM
VFASLLEY

AIVSYMNKRLVLRREKRRKAAEQQQRNEMPMFNASPKAANNNSYEMTLMS
QNSTPAKS

YVQADLYFAGHNSSMNPLMEIPENCDCRTIPMNQHPRLVTDGAHTLWPAP
FARPKKAS

KTCCQRWTPAKIDKLSRYGFPLSFSIFNIVYWLYMKYLSLNSSDKIQEND
KWQQIH
```

SEQ ID NO: 2
*Caenorhabditis elegans* ionotropic GABA receptor subunit UNC-49B.3
LOCUS = AF151643 2601 bp INV 27-JUL-2001
Nucleotide Sequence

```
   1 aagtttgaga gtgatatagg agaaaaacct ccccaacatt ggctcacacc cggattatga
  61 tcttctgctg ctcctgctgc tccttctgct gtagttgaga cgaagaagaa gaagaagctc
 121 cattctcgag aaatggctcg tccattcaca cttatcgtac tcctctccgc acatctgtgt
 181 ctacatgtgg ttgtgacaca ggatgaggac tcacatatca acactcaact cctctcatca
 241 gttctcgata gactcacgaa tcgcactact tatgataaaa gattacggcc caggtatggt
 301 gaaaagccag tcgacgttgg aattacgata cacgtttctt caatctctgc agtttcagaa
 361 gttgatatgg acttcacatt agacttctac atgcgtcaaa cgtggcaaga ccctcgacta
 421 gccttcggaa gtcttgattt ggacttttcc aaagaaatcg actcacttac cgtcggagta
 481 gactacctgg atagactgtg gaaacccgac acgttcttcc caaatgaaaa gaaatcattc
 541 ttccacttgg caaccacaca taactcgttc cttcgtatcg agggtgatgg aacggtttat
 601 actagtcaaa gattaacagt cactgcaacg tgtccaatgg acctgaagct gttcccaatg
 661 gactctcaac actgtaaact ggaaattgaa agctacgggt acgagacgaa agatatcgac
 721 tactattggg ggaagaagcg gactgatttg gagataacgg ctgtcaagtt tgataccttc
 781 cagttgccgc agtttcagcc aacgctgtat tttgtgaata caactaaagc cgagacctca
 841 tcaggaaaat acgtacgcct ggcgctggaa gtaatattgg ttcgaaatat gggcttctac
 901 actatgaaca tcgtcatccc atccatcctg atcgtcacca tatcttgggt atcattttgg
 961 ttgaatcgag aagcttcgcc ggctcgagtt ggattgggtg tgactactgt gctcacaatg
1021 acaactctga tcactacaac aataattcg atgccaaaag tgtcttatgt caagggtctg
1081 gatgtgtttc ttaattttg tttcgtaatg gtattcgcct cgttgctcga gtacgccata
1141 gtatcctaca tgaataaacg actggtcctc cgacgggaaa acgaagaaa agccgccgaa
1201 caacagcagc gaaacgagat gccaatgttc aacgcgagcc cgaaggccgc caataataat
1261 tcatacgaaa tgacacttat gtcgcaaaat tcgacgcctg ccaaaagcta tgtacaggct
1321 gacttgtact ttgccggaca caattcctct atgaatccat tgatggagat cccagaaaat
1381 tgtgattgcc ggacgattcc aatgatgcaa catccacgtc ttgtcacaga cggcgcacat
1441 acgctatggc cggctccatt cgcgcggccg aaaaaggctt ccaagacatg ctgccaacga
1501 tggacgcctg caaaaatcga taagcttagc cgatacggtt tcccattgtc tttctctatc
1561 ttcaatatag tctactggtt gtatatgaaa tatctaagct aaactcgtc ggacaagatc
1621 caggagaacg acaagtggca gcagatccac tgatgcgtat tcgacggccg aaatcgagta
1681 caaatggtgt acgtcgaagg agccgaattg ttcgacagcg gtcaaggccg acgcgaacat
1741 cgaactgtcg agttataaat tcactaaaat ctgccaaaaa cggacacttg ccagcacttc
1801 atcggggacc tactctcgtc tacgggttag tttcatattt gatcgcgaca gcggcttcta
1861 ctttcttcaa atatttttcc ctgccagcct cgtcgtagtt ttatcatgga tctcattctg
1921 gatcaatcgt gactcggcgc cttcgcgaac cctaatcggt acgatgacgg tgctcactga
1981 gactcatctt atgaccggaa ccaatcgacg tcttccacca gttgcctatg taaaagccgt
2041 tgatgtattc ctcggtttct gctatcttct ggttatactg gcgttgatcg agtacgcctg
2101 tgttgcctac tcaaaaaaga agaacgagga tcgtcggaga agagagaaga agacggagca
2161 taaacctgct ccgccgacac ctgatattct tcacgacgtc cgccttgccg aatgcacatg
2221 caacgcggct ccaacctcga tcatcgccgt catcaagcag tcgaatcgat tctgtgtcag
2281 tcacagtcac attgacatcg tcagccgtgc cgcgtttcct cttgttttca tcttgttcaa
```

```
2341 cactctcttc tggctgattc tactgtacaa atccaagcgt ctgccgtata ttagtgaaca 2401 cgagggtgac cgttgcgatg ctccagacct tcattaatct caatccaact tcctcatcat 2461 tttccatttc gaatatctct ttttcttgca cagaagcctt ttttcgtttt tttttattga 2521 tttatttta cggattttta gataatgcac agatgcctca ttgctcaaat aaatttattt 2581 taattaaaaa aaaaaaaaaa a
```

SEQ ID NO: 3
Caenorhabditis elegans ionotropic GABA receptor subunit UNC-49C
Locus = AF151644 1652 bp INV 27-JUL-2001
protein_id = AAD42386.1 mRNA translation
amino acid sequence
"MARPFTLIVLLSAHLCLHVVVTQDEDSHINTQLLSSVLDRLTNR

TTYDKRLRPRYGEKPVDVGITIHVSSISAVSEVDMDFTLDFYMRQTWQDP
RLAFGSLD

LGLSKEIDSLTVGVDYLDRLWKPDTFFPNEKKSFFHLATTHNSFLRIEGD
GTVYTSQR

LTVTATCPMDLKLFPMDSQHCKLEIESYAYSTAEIEYKWCTSKEPNCSTA
VKADANIE

LSSYKFTKICQKRTLASTSSGTYSRLRVSFIFDRDSGFYPLQIFFPASLV
VVLSWISF

WINRDSAPSRTLIGTMTVLTETHLMTGTNRRLPPVAYVKAVDVFLGFCYL
LVILALIE

YACVAYSKKKNEDRRRREKKTEHKPAPPTPDILHDVRLAECTCNAAPTSI
IAVIKQSN

RFCVSHSHIDIVSRAAFPLVFILFNTLFWLILLYKSKRLPYISEHEGDRC
DAPDLH"

SEQ ID NO: 4
Caenorhabditis elegans ionotropic GABA receptor subunit UNC-49C
Locus = AF151644 1652 bp INV 27-JUL-2001
nucleotide sequence

```
   1 cggaaaaacc tccccaacat tggctcacac ccggattatg atcttctgct gctcctgctg 61 ctccttctgc tgtagttgag acgaagaaga agaagaagct ccattctcga gaaatggctc 121 gtccattcac acttatcgta ctcctctccg cacatctgtg tctacatgtg gttgtgacac 181 aggatgagga ctcacatatc aacactcaac tcctctcatc agttctcgat agactcacga 241 atcgcactac ttatgataaa agattacggc ccaggtatgg tgaaaagcca gtcgacgttg 301 gaattacgat acacgtttct tcaatctctg cagtttcaga agttgatatg gacttcacat 361 tagacttcta catgcgtcaa acgtggcaag accctcgact agccttcgga agtcttgatt 421 tgggactttc caaagaaatc gactcactta ccgtcggagt agactacctg atagactgt 481 ggaaacccga cacgttcttc ccaaatgaaa agaaatcatt cttccacttg caaccacac 541 ataactcgtt ccttcgtatc gagggtgatg gaacggttta tactagtcaa agattaacag 601 tcactgcaac gtgtccaatg gacctgaagc tgttcccaat ggactctcaa cactgtaaac 661 tggaaattga agctatgcg tattcgacgg ccgaaatcga gtacaaatgg tgtacgtcga 721 aggagccgaa ttgttcgaca gcggtcaagg ccgacgcgaa catcgaactg tcgagttata 781 aattcactaa aatctgccaa aaacggacac ttgccagcac ttcatcgggg acctactctc 841 gtctacgggt tagtttcata tttgatcgcg acagcggctt ctactttctt caaatatttt 901 tccctgccag cctcgtcgta gttttatcat ggatctcatt ctggatcaat cgtgactcgg 961 cgccttcgcg aaccctaatc ggtacgatga cggtgctcac tgagactcat cttatgaccg 1021 gaaccaatcg acgtcttcca ccagttgcct atgtaaaagc cgttgatgta ttcctcggtt 1081 tctgctatct tctggttata ctggcgttga tcgagtacgc ctgtgttgcc tactcaaaaa 1141 agaagaacga ggatcgtcgg agaagagaga agaagacgga gcataaacct gctccgccga 1201 cacctgatat tcttcacgac gtccgccttg ccgaatgcac atgcaacgcg gctccaacct 1261 cgatcatcgc cgtcatcaag cagtcgaatc gattctgtgt cagtcacagt cacattgaca 1321 tcgtcagccg tgccgcgttt cctcttgttt tcatcttgtt caacactctc ttctggctga 1381 ttctactgta caaatccaag cgtctgccgt atattagtga acacgagggt gaccgttgcg
```

-continued

```
1441 atgctccaga ccttcattaa tctcaatcca acttcctcat cattttccat ttcgaatatc 1501 tcttttttctt gcacagaagc cttttttcgt ttttttttat tgatttattt ttacggattt 1561 ttagataatg cacagatgcc tcattgctca aataaattta ttttaattgt cgaaaaaaaa 1621 aaaaaaaaaa aaaaaaaaa aaaaaaaaaa aa
```

---

What is claimed is:

1. A method of screening for compounds that modulate a $GABA_A$ receptor at a location of interest on the receptor, comprising
exposing a test compound to a modified $GABA_A$ receptor, wherein the modification is at the location of interest on the receptor, and wherein the location of interest is in the Y segment of the M1 domain of an alpha subunit of the modified $GABA_A$ receptor; and
detecting altered binding of the test compound to the modified $GABA_A$ receptor compared to a wild type $GABA_A$ receptor, wherein the altered binding is indicative of a compound that modulates the $GABA_A$ receptor in the Y segment of the M1 domain of the alpha subunit of the modified $GABA_A$ receptor.

2. The method of claim 1, wherein the screening is high throughput.

3. The method of claim 1, wherein the modulation comprises an increase in receptor interaction between the test compound and the modified $GABA_A$ receptor.

4. The method of claim 1, wherein the modulation comprises a decrease in receptor interaction between the test compound and the modified $GABA_A$ receptor.

5. The method of claim 1, wherein the altered binding of the compound being screened is compared to that found when the compound interacts with a wild type receptor.

6. The method of claim 1, wherein the location of interest is residue 272 of SEQ ID NO: 1.

7. The method of claim 1, wherein the Y segment of the M1 domain comprises residues 265 to 273 of SEQ ID NO: 1.

8. The method of claim 7, wherein the Y segment of the M1 domain is homologous to residues 265 to 273 of SEQ ID NO: 1.

9. The method of claim 1, wherein the Y segment of the M1 domain comprises residues 266 to 274 of SEQ ID NO: 3.

10. The method of claim 7, wherein the Y segment of the M1 domain is homologous to residues 266 to 274 of SEQ ID NO: 3.

11. A method of screening for a compound that modulates a $GABA_A$ receptor at a location of interest on the receptor comprising the following steps:
   a) measuring the response of a cell expressing a wild-type $GABA_A$ receptor to a test compound;
   b) measuring the response of a cell expressing a mutated $GABA_A$ receptor to the test compound, wherein the mutation is in the location of interest, and wherein the location of interest is in the Y segment of the M1 domain of an alpha subunit of the mutated $GABA_A$ receptor;
   c) comparing the response of the cell to the test compound in steps a) and b); and
   d) determining if the test compound modulates the mutated $GABA_A$ receptor at the location of interest based on the results of step c).

12. A method of screening for a compound that modulates a GABA receptor comprising:
   a) measuring the response of cells expressing a wild-type $GABA_A$ receptor to GABA;
   b) measuring the response of cells expressing a mutant $GABA_A$ receptor to GABA, wherein the mutation is in the location of interest, and wherein the location of interest is in the Y segment of the M1 domain of an alpha subunit of the mutated $GABA_A$ receptor;
   c) comparing the measurements of step a) and b);
   d) measuring the response of cells expressing the wild-type $GABA_A$ receptor to GABA plus a test compound;
   e) measuring the response of cells expressing the mutant $GABA_A$ receptor, wherein the mutation is in the location of interest, and wherein the location of interest is in the Y segment of the M1 domain of an alpha subunit of the mutated $GABA_A$ receptor to GABA plus the test compound;
   f) comparing the measurements of d) and e); and
   g) comparing the results of steps c and f); wherein a difference in response of the cells in the presence of a test compound and the response of the cells in the absence of a test compound indicates a compound that modulates the response of a $GABA_A$ receptor to GABA.

13. The method of claim 11 or 12, wherein the screening is high throughput.

14. The method of claim 11 or 12, wherein the modulation comprises an increase in receptor interaction between the test compound and the modified $GABA_A$ receptor.

15. The method of claim 11 or 12, wherein the modulation comprises a decrease in receptor interaction between the test compound and the modified $GABA_A$ receptor.

16. The method of claim 11 or 12, wherein the measuring steps comprise measuring the response at various concentrations of test compound.

17. The method of claim 11, wherein the location of interest is residue 272 of SEQ ID NO: 1.

18. The method of claim 12, wherein the measuring steps comprise measuring the response at various concentrations of GABA.

19. The method of claim 12, wherein the location of interest is residue 272 of SEQ ID NO: 1.

* * * * *